(12) United States Patent
Obendorf et al.

(10) Patent No.: US 7,807,406 B2
(45) Date of Patent: Oct. 5, 2010

(54) FAGOPYRITOL SYNTHASE GENES AND USES THEREOF

(75) Inventors: Ralph L. Obendorf, Ithaca, NY (US); Takashi Ueda, Fort Myers, FL (US)

(73) Assignee: Cornell Research Foundation, Inc., Ithaca, NY (US)

(*) Notice: Subject to any disclaimer, the term of this patent is extended or adjusted under 35 U.S.C. 154(b) by 958 days.

(21) Appl. No.: 10/435,226

(22) Filed: May 9, 2003

(65) Prior Publication Data

US 2004/0038357 A1 Feb. 26, 2004

Related U.S. Application Data

(60) Provisional application No. 60/379,373, filed on May 9, 2002.

(51) Int. Cl.
*C12P 21/06* (2006.01)
*A61K 31/70* (2006.01)
(52) U.S. Cl. .................. 435/69.1; 514/35; 514/25; 514/53; 536/123.1
(58) Field of Classification Search ............... 435/69.1, 435/123; 536/23.2
See application file for complete search history.

(56) References Cited

U.S. PATENT DOCUMENTS

| | | | |
|---|---|---|---|
| 2,112,553 A | 3/1938 | Bartow et al. | |
| 2,456,470 A | 12/1948 | Thomas | |
| 3,270,064 A | 8/1966 | Inaba et al. | |
| 4,010,258 A | 3/1977 | Murao | |
| 4,482,761 A | 11/1984 | Chao et al. | |
| 4,933,281 A | 6/1990 | Daniels et al. | |
| 5,064,762 A | 11/1991 | Rabinowitz | |
| 5,091,596 A | 2/1992 | Kennington et al. | |
| 5,096,594 A | 3/1992 | Rabinowitz | |
| 5,122,603 A | 6/1992 | Larner et al. | |
| 5,124,360 A | 6/1992 | Larner et al. | |
| 5,296,364 A | 3/1994 | Agawal | |
| 5,317,095 A | 5/1994 | Suzuki et al. | |
| 5,406,005 A | 4/1995 | Piccariello | |
| 5,463,142 A | 10/1995 | Riley et al. | |
| 5,516,950 A | 5/1996 | Piccariello et al. | |
| 5,648,210 A | 7/1997 | Kerr et al. | |
| 5,710,365 A | 1/1998 | Kerr et al. | |
| 5,827,896 A | 10/1998 | Ostlund et al. | |
| 6,093,697 A | 7/2000 | Larner et al. | |
| 6,162,795 A * | 12/2000 | Obendorf et al. | 514/35 |
| 6,486,127 B1 | 11/2002 | Gunn et al. | |
| 6,492,341 B1 | 12/2002 | Obendorf et al. | |
| 6,753,461 B2 * | 6/2004 | Taji et al. | 800/289 |

FOREIGN PATENT DOCUMENTS

| | | |
|---|---|---|
| JP | 3-11026(A) | 1/1991 |
| WO | WO 93/02196 | 2/1993 |
| WO | WO 98/50049 | 11/1998 |
| WO | WO 01/89352 A1 | 11/2001 |

OTHER PUBLICATIONS

Nestler et al., "Ovulatory and Metabolic Effects of D-Chiro-inositol in the Polycystic Ovary Syndrome," *New England Journal of Medicine*, 340(17):1314-1320 (1999).
Ogawa et al., "A New Glycoside, 1D-2-O-α-D-Galactopyranosyl-Chiro-Inositol from Jojoba Beans," *Carbohydrate Res.*, 302:219-221 (1997).
Kornienko et al., "Synthesis of a Jojoba Bean Disaccharide," *Carbohydrate Res.*, 310:141-144 (1998).
Berlin et al., "Glycosyl-Inositol Derivatives II. Synthesis of 2-Amino-2-Deoxy-*D*-Galactosyl-α-1,3-*D-Chiro*-Inositol," *Tetrahedron Lett.*, 31(8):1109-1112 (1990).
Richter et al., "Structure of Galactosylononitol," *J. Nat. Prod.*, 60(8):749-751 (1997).
Petek et al., "Isolation of Two Galactosidases of Myo-inositol from Vetch seeds," *C.R. Acad. Sc. Paris Sciences Série D*, 263:195-197 (1966).
Petek et al., "Purification and Properties of the α-Galactosidase of the Germinating Seed of *Vicia sativa*," *European J. Biochemistry*, 8:395-402 (1969) (Abstract).
Gao et al., "A Novel Alkaline α-Galactosidase from Melon Fruit with a Substrate Preference for Raffinose," *Plant Physiology*, 119:979-987 (1999).
Larner et al., "Rat Liver Insulin Mediator Which Stimulates Pyruvate Dehydrogenase Phosphatase Contains Galactosamine and D-Chiroinositol," *Biochemical and Biophysical Research Communications*, 151(3):1416-1426 (1988).
Schweizer et al., "Low Molecular Weight Carbohydrates From Leguminous Seeds; A New Disaccharide: Galactopinitol," *J. Sci. Fd Agric.*, 29:148-154 (1978).
Schweizer et al., "Purification and Structure Determination of Three α-D-galactopyranosylcyclitols From Soya Bean," *Carbo. Res.*, 95:61-71 (1981).
Shiomi et al., "A New Digalactosyl Cyclitol From Seed Balls of Sugar Beet," *Agric. Biol. Chem.*, 52:1587-1588 (1988).
Ortmeyer et al., "In vivo D-chiroinositol Activates Skeletal Muscle Glycogen Synthase and Inactivates Glycogen Phosphorylase in Rhesus Monkeys," *Nutritional Biochemistry*, 6:499-503 (1995).
Ortmeyer et al., "Effects of D-Chiroinositol Added to a Meal on Plasma Glucose and Insulin In Hyperinsulinemic Rhesus Monkeys," *Obesity Res.*, 3 (Supp 4):605S-608S (1995).
Horbowicz et al., "Maturing Buckwheat Seeds Accumulate Galactochiro-inositol Instead of Stachyose," Abstract 908, *Plant Physiology*, 105:S-164 (1994).

(Continued)

*Primary Examiner*—Richard G Hutson
(74) *Attorney, Agent, or Firm*—Nixon Peabody LLP

(57) ABSTRACT

The present invention relates to an isolated DNA molecule encoding a fagopyritol synthase. A method for producing a fagopyritol, an insulin mediator, an insulin mediator analogue, an insulin mediator homologue, or an insulin mediator inhibitor is also described. The method includes providing a fagopyritol synthase, providing a substrate comprising a galactosyl donor and a galactosyl acceptor, and combining the fagopyritol synthase with the substrate under conditions effective produce a fagopyritol, an insulin mediator, an insulin mediator analogue, an insulin mediator homologue, or an insulin mediator inhibitor.

6 Claims, 27 Drawing Sheets

OTHER PUBLICATIONS

Horbowicz et al., "Galactosyl-chiro-inositol in Buckwheat Seeds Correlates with Desiccation Tolerance During Maturation and Germination," *Agronomy Abst.*, 178 (1994).

Horbowicz et al., "Fagopyritol B1, O-α-D-galactopyranosyl-(1→2)-D-chiro-inositol, a Galactosyl Cyclitol in Maturing Buckwheat Seeds Associated with Desiccation Tolerance," *Planta*, 205:1-11 (1998).

Szczecinski et al., "NMR Investigation of the Structure of Fagopyritol B1 from Buckwheat Seeds," *Bulletin of the Polish Academy of Sciences Chemistry*, 46(1):9-13 (1998).

Yasui, "Dissimilarity in Low Molecular Weight Carbohydrate Composition of the Seeds of Cultivated Soybean [Glycine max (L.) Merrill subsp. max] and Wild Soybean [G. max subsp. soja (Sieb. et Zucc.) Ohashi]," *Agric. Biol. Chem.*, 49:933-937 (1985).

Quemener et al., "Ciceritol, a Pinitol Digalactoside from Seeds of Chickpea, Lentil and White Lupin," *Phytochemistry*, 22:1745-1751 (1983).

Obendorf et al., "Seed Desiccation Tolerance and Storability: Dependence on the Flatulence-Producing Sugars," International Workshop: Desiccation Tolerance and Sensitivity of Seeds and Vegetative Plant Tissues, South Africa, Jan. 19, 1994 (Abstract of Oral Presentation).

Obendorf et al., "Seed Set and Cessation of Seed Growth in Buckwheat," Developing a Strategic Plan for Integrated Buckwheat Research, North Dakota State University Research and Extension Center, Jul. 21, 1994, (Abstract of Oral Presentation).

Obendorf et al., "Seed Set and Cessation of Seed Growth in Buckwheat," Quarterly Report to Sponsors, Apr. 1-Jun. 30, 1994.

Obendorf, "Buckwheat Pharmaceuticals: 1. Characterization," "Buckwheat Pharmaceuticals: 2. Model for Industrial Isolation," "Buckwheat Pharmaceuticals: 3. Equipment," Research Proposals to MINN-DAK Growers Ltd. (Nov. 27, 1995).

Obendorf et al., "Buckwheat Pharmaceuticals: Buckwheat Project 1999 Annual Report," (1999).

Steadman et al., "Minerals, Phytic Acid, Tannin and Rutin in Buckwheat Seed Milling Fractions," *J. Sci. Food Agric.*, 81:1094-1100 (2001).

Steadman et al., "Fagopyritols, D-*chiro*-Inositol, and Other Soluble Carbohydrates in Buckwheat Seed Milling Fractions," *J. Agric. Food Chem.*, 48:2843-2847 (2000).

Steadman et al., "Buckwheat Seed Milling Fractions: Description, Macronutrient Composition and Dietary Fibre," *J. Cereal Sci.*, 33:271-278 (2001).

Brenac et al., "Fagopyritol and Raffinose Oligosaccharides Related to Dessication Tolerance of Buckwheat Hypocotyes," *Plant Physiology*, 108:S-19 (1995).

Chien et al., "Occurrence of a Novel Galactopinitol and its Changes with Other Non-Reducing Sugars During Development of *Leucaena leucocephala* Seeds," *Plant and Cell Physiology* 37:539-544 (1996) (Abstract).

Obendorf et al., "Soluble Oligosaccharides and Galactosyl Cyclitols in Maturing Soybean Seeds in planta and in vitro," *Crop Sci.* 38:78-84 (1998) (Abstract).

Horbowicz et al., "Seed Dessication Tolerance and Storability: Dependence on Flatulence-Producing Oligosaccharides and Cyclitols—Review and Survey," *Seed Sci. Res.* 4:385-405 (1994) (Abstract).

Larner et al., "Identification of a Novel Inositol Glycan Signaling Pathway with Significant Therapeutic Relevance to Insulin Resistance: An Insulin Signaling Model Using both Tyrosine Kinase and G-Proteins," *Diabetes Reviews*, 7:217-231 (1999).

ICMR Central Technical Co-ordinating Unit, "Multicentric Study of Efficacy of Periconceptional Folic Acid Containing Vitamin Supplementation in Prevention of Open Neural Tube Defects from India," *Indian J. Med. Res.* 112:206-211 (2000) (Abstract).

Harmon et al., "Prenatal Ultrasound Detection of Isolated Neural Tube Defects: Is Cyctogenetic Evaluation Warranted?" *Obstet. Gynecol.*, 86(4) Pt. 1:595-599 (1995) (Abstract).

Chengappa et al., "Inositol as an Add-On Treatment for Bipolar Depression," *Bipolar Disord.* 2(1):47-55 (2000) (Abstract).

Steadman et al., "Purification and Molecular Structure of Two Digalactosyl D-chiro-inositols and Two Trigalactosyl D-chiro-inositols from Buckwheat Seeds," *Carbohydrate Research* 331:19-25 (2001).

Obendorf et al., "Molecular Structure of Fagopyritol A1 (*O*-α-D-galactopyranosyl-(13)-D-*chiro*-inositol) by NMR," *Carbohydrate Research*, 328:623-627 (2000).

Odorcic et al., "Galactosyl Cyclitol Accumulation Enhanced by Substrate Feeding of Soybean Embryos," In: The Biology of Seeds: Recent Research Advances, Nicolas et al., Eds., Wallingford, UK, CAB International, pp. 51-60 (2003).

Obendorf et al., "Recent Accomplishments and New Opportunities in Seed Research," In: The Biology of Seeds: Recent Research Advances, Nicolas et al., Eds., Wallingford, UK, CAB International, pp. 447-452 (2003).

Odorcic et al., "Substrate Feeding Stimulates Galactosyl Cyclitol Accumulation in Soybean Embryos," Seventh International Workshop on Seeds, Salamanca, Spain (May 12-16, 2002).

Frydman & Neufeld, "Synthesis of Galactosylinositol by Extracts from Peas," *Biochem. Biophys. Res. Commun.* 12(2):121-125 (1963).

Hoch et al., "Purification and Characterization of Stachyose Synthase from Lentil (*Lens culinaris*) Seeds: Galactopinitol and Stachyose Synthesis," *Arch. Biochem. Biophys.* 366(1):75-81 (1999).

Ueda et al., "A Multifunctional Galactinol Synthase Catalyzes the Synthesis of Fagopyritol A1 and Fagopyritol B1 in Buckwheat Seed," *Plant Sci.* 168:681-690 (2005).

Japanese Office Action dated Dec. 17, 2008.

\* cited by examiner

```
  1  gagcacccaaagctctgctagcaccatattcaaatcctcaagaatcatcaaatcttccaa   60
 61  ccaatcctcaagttccaaccaaatggcaccagaactcatcacaatcggagccgatcactc  120
                        M  A  P  E  L  I  T  I  G  A  D  H  S
121  gattttgccagcggaatcgttgattccggttgaccgagcttacgtgacgtttctcgccgg  180
      I  L  P  A  E  S  L  I  P  V  D  R  A  Y  V  T  F  L  A  G
181  gaacggagactatgtcaaggagttgtcggattagcaaagggactgaggaaagtgaaggc   240
      N  G  D  Y  V  K  G  V  V  G  L  A  K  G  L  R  K  V  K  A
241  tgcttatcctcttgttgtagcggtttttacccgacgttccgctagagcatcgccgactcct 300
      A  Y  P  L  V  V  A  V  L  P  D  V  P  L  E  H  R  R  L  L
301  ggaggcgcagggttgtatcgtaagggaaatcgagccgatatacccgccggaaaacaattg  360
      E  A  Q  G  C  I  V  R  E  I  E  P  I  Y  P  P  E  N  N  C
361  cgagttcgctcacgcatactatgtcatcaactactccaagcttcgcatctgggagtttgt  420
      E  F  A  H  A  Y  Y  V  I  N  Y  S  K  L  R  I  W  E  F  V
421  ggagtacagtaagatgatatacttggacggggacatacaggtgtaccagaacattgacca  480
      E  Y  S  K  M  I  Y  L  D  G  D  I  Q  V  Y  Q  N  I  D  H
481  cctgtttgaccagccggacggctactttacgcggtgatggactgttttgtgagccatc   540
      L  F  D  Q  P  D  G  Y  F  Y  A  V  M  D  C  F  C  E  P  S
541  atggagcaagacgattcagtacaagatcggatactgccaacagtgccggagaaggtagc  600
      W  S  K  T  I  Q  Y  K  I  G  Y  C  Q  Q  C  P  E  K  V  A
601  gtggccgttcgaggctggccccaagccttctctgtacttcaatgccggattctttgttta  660
      V  P  L  E  A  G  P  K  P  S  L  Y  F  N  A  G  F  F  V  Y
661  cgagccgagccttgagacttacaaggatctcattgacactctcaaagtcacgactcctac  720
      E  P  S  L  E  T  Y  K  D  L  I  D  T  L  K  V  T  T  P  T
721  ctcctttgccgaccaggacttcttgaacatgtacttcaaggacaagttcaagccactccc  780
      S  F  A  E  Q  D  F  L  N  M  Y  F  K  D  K  F  K  P  L  P
781  catagactacaacttagtcttagccttcctgtggaggcatccggagaaagttgaccttaa  840
      I  D  Y  N  L  V  L  A  F  L  W  R  H  P  E  K  V  D  L  N
841  ccgagtgaaggtagttcactactgtgcggcgggtctaagccatggaggtacacgggcaa  900
      R  V  K  V  V  H  Y  C  A  A  G  S  K  P  W  R  Y  T  G  K
901  ggaagagaacatggacagagaagacatcaaattgcttgtgaaaaaatggtgggatatcta  960
      E  E  N  M  D  R  E  D  I  K  L  L  V  K  K  W  W  D  I  Y
961  caacgacgagtcattggacctcaagaaaccggtccatttagtgcagcagcccacggaggt 1020
      N  D  E  S  L  D  L  K  K  P  V  H  L  V  Q  Q  P  T  E  V
1021 gctcaaggcggcgctctcggaggctagcctgttaaatatgtggctgctccttccgcagc  1080
      L  K  A  A  L  S  E  A  R  P  V  K  Y  V  A  A  P  S  A  A
1081 ttaagtatcggcttgtatttggtaatggttttgtttttgcgaatgtaaagtagaaagaa  1140
       *
1141 ggggcgagagtttgtgatattggggcaatgcggaatggtgcgtataaatgtgtgttgtaa 1200
1201 tggcaactgttttacttggaattatatgtaagaagtaagaatatatgtataaaaaaaaa  1260
1261 aaaaaaaaa                                                    1269
```

FIGURE 1

```
   1  ttggtttcgaacttgatcaaaacctcacaaaaacacgtaagcaaaatcacttccgagatg    60
                                                     M  T  S  E  M
  61  gcgccacagaacataacgaatgcagaaagaggagccgagcaagtgaagccgtcgagccag   120
       A  P  Q  N  I  T  N  A  E  R  G  A  E  Q  V  K  P  S  S  Q
 121  ccaagccgagcctacgtgacattcttagccggcaacggtgactacgtgaagggagttata   180
       P  S  R  A  Y  V  T  F  L  A  G  N  G  D  Y  V  K  G  V  I
 181  gggctcgccaaaggcctgaggaaaactcagagcggttacccgcttgtggtggcggttctc   240
       G  L  A  K  G  L  R  K  T  Q  S  G  Y  P  L  V  V  A  V  L
 241  cctgacgttccgcaggagcaccgccgtatgctggtggcccaaggctgtataataaaggaa   300
       P  D  V  P  Q  E  H  R  R  M  L  V  A  Q  G  C  I  I  K  E
 301  atccagcccgttaacccgccgataaccagactcagtttgccatggcttattacgtcatc   360
       I  Q  P  V  N  P  P  D  N  Q  T  Q  F  A  M  A  Y  Y  V  I
 361  aactactccaagctccgtatatggagtttatcgagtatagtaagatcatatatcttgat   420
       N  Y  S  K  L  R  I  W  F  I  E  Y  S  K  M  I  Y  L  D
 421  ggagacatccaagtttacgacaacatcgaccacctcttcgacctaccagaccggtacttg   480
       G  D  I  Q  V  Y  D  N  I  D  H  L  F  D  L  P  D  G  Y  L
 481  tacggtgccatggattgcttttgcgagaagacttggagtcattcgcttccatataagatt   540
       Y  G  A  M  D  C  F  C  E  K  T  W  S  H  S  L  P  Y  K  I
 541  gggtattgccaacagtgccccggacagggtccagtggcccgaaaggctcggcccaaaacca   600
       G  Y  C  Q  Q  C  P  D  R  V  Q  W  P  E  R  L  G  P  K  P
 601  acactctacttcaatgcagggatgttcatcttccagcctagcgtttctacttataatgat   660
       T  L  Y  F  N  A  G  M  F  I  F  Q  P  S  V  S  T  Y  N  D
 661  ctccttcatacactcgagatcacccctcctacaccttttgctgagcaggactttttcaat   720
       L  L  H  T  L  E  I  T  P  P  T  P  F  A  E  Q  D  F  L  N
 721  atgtacttcaaggatgtgtacagaccaattccgaacgtttacaacttggtattggctttg   780
       M  Y  F  K  D  V  Y  R  P  I  P  N  V  Y  N  L  V  L  A  L
 781  ttgtggtatcatcctgggttaatgaagcttgatgacgttaaagtcgttcactattgtgcc   840
       L  W  Y  H  P  G  L  M  K  L  D  D  V  K  V  V  H  Y  C  A
 841  gatggttcaaaaccatggcgtatacaggcaaaggggataacatggacagggaagacgtt   900
       D  G  S  K  P  W  R  Y  T  G  K  G  D  N  M  D  R  E  D  V
 901  aggatgctagtgaagaagtggtggagatttacgatgatcagtctctcgaccctcagcct   960
       R  M  L  V  K  K  W  W  E  I  Y  D  D  Q  S  L  D  P  Q  P
 961  aagatggtcgagggcaagaagttcgacaaattagaggagtacagcgagtccctcgaccac  1020
       K  M  V  E  G  K  K  F  D  K  L  E  E  Y  S  E  S  L  D  H
1021  ccgcccaaggtggcagaggaagataagctagagaagccatggcagcgatgacaggcttc  1080
       P  P  K  V  A  E  E  D  K  L  E  K  P  M  A  A  M  T  G  F
1081  agctacgtacacgccccgtctgctgcctgattgttgaaacaaggccaaggttccacaaa  1140
       S  Y  V  H  A  P  S  A  A  *
1141  cgaggga ccaaaaactcctatagtattatagatcgtatatttctgttattgctttcca  1200
1201  attaagcaactaagatgttcatatagtagttctggaaatgaatacgggcatagttgtga  1260
1261  acttgtaatctcattttgtttttcggaatgttcaagtatttcttctaaaaaaaaaaaa  1320
1321  aaaaaa                                                        1326
```

| | | |
|---|---|---|
| 1 | agccaaaagtttgttttcatagtgtgttttgtttcccaaatcctactcttgtgaccacaa | 60 |
| 61 | cccttcctcctctttcttttgaaacctcttttttctattccccaaccaaacaagcaaac | 120 |
| 121 | gctactcactcatcatcactgagatc<u>atg</u>gctcctaatatcaccactgtcaaaaccacca | 180 |
| |                          M  A  P  N  I  T  T  V  K  T  T  I | |
| 181 | tcaccgacgctcaagccaaggtcgccaccgatcatggtcgtgcctacgtcaccttcctcg | 240 |
| | T  D  A  Q  A  K  V  A  T  D  H  G  R  A  Y  V  T  F  L  A | |
| 241 | ccggaaacggtgactatgtgaaaggtgtcgttggcttggcaaaaggtctgagaaaagtga | 300 |
| | G  N  G  D  Y  V  K  G  V  V  G  L  A  K  G  L  R  K  V  K | |
| 301 | agagcatgtaccctctggtggttgcagtgctacccgatgttccccaagatcaccgcaaca | 360 |
| | S  M  Y  P  L  V  V  A  V  L  P  D  V  P  Q  D  H  R  N  I | |
| 361 | ttctcacctcccaaggttgcattgttagagagattgagcccgtgtaccccccagagaatc | 420 |
| | L  T  S  Q  G  C  I  V  R  E  I  E  P  V  Y  P  P  E  N  Q | |
| 421 | aaacccagtttgccatggcatattacgtcatcaactattccaagctacgtatttgggagt | 480 |
| | T  Q  F  A  M  A  Y  Y  V  I  N  Y  S  K  L  R  I  W  E  F | |
| 481 | tgtggagtacagcaagatgatatacctagacggtgatatccaagttttgacaacattg | 540 |
| | V  E  Y  S  K  M  I  Y  L  D  G  D  I  Q  V  F  D  N  I  D | |
| 541 | accacttgtttgacttgcctgataactacttctatgcggtgatggactgtttctgtgagc | 600 |
| | H  L  F  D  L  P  D  N  Y  F  Y  A  V  M  D  C  F  C  E  P | |
| 601 | caacttggggccacactaaacaatatcagatcggttactgccagcagtgcccccataagg | 660 |
| | T  W  G  H  T  K  Q  Y  Q  I  G  Y  C  Q  Q  C  P  H  K  V | |
| 661 | ttcagtggcccactcactttgggcccaaacctcctctctatttcaatgctggcatgtttg | 720 |
| | Q  W  P  T  H  F  G  P  K  P  P  L  Y  F  N  A  G  M  F  V | |
| 721 | tgtatgagcccaatttggctacttaccgtgacctccttcaaacagtccaagtcacccagc | 780 |
| | Y  E  P  N  L  A  T  Y  R  D  L  L  Q  T  V  Q  V  T  Q  P | |
| 781 | ccacttcctttgctgaacaggatttttgaacattacttcaaggacaaatataggccaa | 840 |
| | T  S  F  A  E  Q  D  F  L  N  I  Y  F  K  D  K  Y  R  P  I | |
| 841 | ttcctaatgtctacaatcttgtgctggccatgctgtggcgtcaccctgagaacgttgagc | 900 |
| | P  N  V  Y  N  L  V  L  A  M  L  W  R  H  P  E  N  V  E  L | |
| 901 | ttgacaaagttaaagtggttcactactgtgctgctgggtctaagccttggaggtacactg | 960 |
| | D  K  V  K  V  V  H  Y  C  A  A  G  S  K  P  W  R  Y  T  G | |
| 961 | ggaaggaggagaatatggagagagaagatatcaagatgttagtgaaaaagtggtgggata | 1020 |
| | K  E  E  N  M  E  R  E  D  I  K  M  L  V  K  K  W  D  I | |
| 1021 | tatatgaggatgagactttggactacaacaatcccactcaatgtggataagttcactgcgg | 1080 |
| | Y  E  D  E  T  L  D  Y  N  N  P  L  N  V  D  K  F  T  A  A | |
| 1081 | cacttatggaggttggtgaagtcaagttcgtccgtgccccatctgctgct<u>taa</u>gagtgtc | 1140 |
| | L  M  E  V  G  E  V  K  F  V  R  A  P  S  A  A  * | |
| 1141 | tttggaaatcaagtgtgatccaagtacatgtacaaagtcatacatcattacattaacttt | 1200 |
| 1201 | tatgtatttctaaaagtcatacatcattacattaagttttatgtatttctaaagtcttaa | 1260 |
| 1261 | gacttaagaggacctttttatgtgtcccggcttttcttttttcttttttccaattctgt | 1320 |
| 1321 | cattgtaaagcaggtgaataccggtatccttaattttataaatggatatgaattttattt | 1380 |
| 1381 | tgcaaaaaaaaaaaaaaaaaaaaaaaa | 1406 |

FIGURE 4

```
FeGolS-1    MAPELITIGADHSILPAESLIP---VDRAYVTFLAGNGDYVKGVVGLAKG
FeGolS-2    MTSEMAPQNITNAERGAEQVKPSSQPSRAYVTFLAGNGDYVKGVIGLAKG
FeGolS-3    --------------------------------------------------

FeGolS-1    LRKVKAAYPLVVAVLPDVPLEHRRLLEAQGCIVREIEPIYPPENNCEFAH
FeGolS-2    LRKTQSGYPLVVAVLPDVPQEHRRMLVAQGCIIKEIQPVNPPDNQTQFAM
FeGolS-3    ------------------------------------------------AM
                 GS3 ▶
FeGolS-1    AYYVINYSKLRIWEFVEYSKMIYLDGDIQVYQNIDHLFDQPDGYFYAVMD
FeGolS-2    AYYVINYSKLRIWEFIEYSKMIYLDGDIQVYDNIDHLFDLPDGYLYGAMD
FeGolS-3    AYYVINYSKLRIWEFIEYSKMIYLDGDIQVYDNIDHLFDLPDGYLYGAMD
              ◀GS2              ◀GS1
FeGolS-1    CFCEPSWSKTIQYKIGYCQQCPEKVAWRLEAGPKPSLYFNAGFFVYEPSL
FeGolS-2    CFCEKTWSHSLPYKIGYCQQCPDRVQWPERLGPKPTLYFNAGMFIFEPSV
FeGolS-3    CFCEKTWSHSLPYKIGYCQQCPDRVQWPERLGPKPTLYFNAGMFIFEPSV

FeGolS-1    ETYKDLIDTLKVTTPTSFAEQDFLNMYFKDKFKPLPIDYNLVLAFLWRHP
FeGolS-2    STYNDLLHTLEITPPTPFAEQDFLNMYFKDVYRPIPNVYNLVLALLWYHP
FeGolS-3    STYNDLLHTLEITPPTPFAEQDFLNMYFKDVYRPIPNVYNLVLALLWYHP

FeGolS-1    EKVDLNRVKVVHYCAAGSKPWRYTGKEENMDREDIKLLVKKWWDIYNDES
FeGolS-2    GLMKLDEVKVVHYCADGSKPWRYTGKGDNMDREDVRMLVKKWWEIYDDQS
FeGolS-3    GLMNLDEVKVVHYCADGSKPWRYTGKGDNMDREDVRMLVKKWWEIYDDQS

FeGolS-1    LDLKKPVH--------------LVQQP-----TEVLKAALSEARPVKYVAA
FeGolS-2    LDPQPKMVEGKKFDKLEEYSESLDHPPKVAEEDKLEKPMAAMTGFSYVHA
FeGolS-3    LDPQPKVVEGKKFDKL-EYSESLDHPPKVAEEDKLEKPMAAMTGFSYVHA
              ◀GS4
FeGolS-1    PSAA
FeGolS-2    PSAA
FeGolS-3    PSAA
```

FAGOPYRITOL SYNTHASE GENES AND USES THEREOF

This application claims the benefit of U.S. Provisional Patent Application Ser. No. 60/379,373, filed May 9, 2002, which is hereby incorporated by reference in its entirety.

The present invention was developed with support under Cooperative State Research, Education and Extension Service, U.S. Department of Agriculture Project No. NYC-125323. The U.S. Government has certain rights.

FIELD OF THE INVENTION

The present invention relates to fagopyritol synthase genes and methods of producing fagopyritols, insulin mediators, insulin mediator analogues, or insulin mediator homologues.

BACKGROUND OF THE INVENTION

Embryos of many plant seeds accumulate sucrose and the raffinose family of oligosaccharides (RSO), such as raffinose, stachyose and verbascose, as the major soluble sugars in mature seeds (Horbowicz et al., Seed Sci. Res. 4:385-405 (1994); Obendorf, See Sci. Res. 7:63-74 (1997)). Soybean (*Glycine max* (L.) Merrill) seeds accumulate soluble carbohydrates, primarily sucrose, raffinose, and stachyose and lesser amounts of galactopinitol A, galactopinitol B, ciceritol, and fagopyritol B1 in axis and cotyledon tissues as part of the seed maturation process (Obendorf et al., Crop Science 38:78-84 (1998)). By contrast, embryos of maturing buckwheat (*Fagopyrum esculentum* Moench) seeds accumulate fagopyritols, galactosyl derivatives of D-chiro-inositol, instead of raffinose and stachyose (Horbowicz et al., Planta 205:1-11 (1998)). Six fagopyritols, in two different series, are present in buckwheat embryos: fagopyritol A1 (α-D-galactopyranosyl-(1→3)-1D-chiro-inositol), fagopyritol A2 (α-D-galactopyranosyl-(1→6)-α-D-galactopyranosyl-(1→3)-1D-chiro-inositol), fagopyritol A3(α-D-galactopyranosyl-(1→6)-α-D-galactopyranosyl-(1→6)-α-D-galactopyranosyl-(1→3)-1D-chiro-inositol), fagopyritol B1 (α-D-galactopyranosyl-(1→2)-1D-chiro-inositol), fagopyritol B2 (α-D-galactopyranosyl-(1→6)-α-D-galactopyranosyl-(1→2)-1D-chiro-inositol), and fagopyritol B3 (α-D-galactopyranosyl-(1→6)-α-D-galactopyranosyl-(1→6)-α-D-galactopyranosyl-(1→2)-1D-chiro-inositol) (Horbowicz et al., Planta 205:1-11 (1998); Szczecinski et al., Bull. Polish Acad. Sci., Chem. 46:9-13 (1998); Obendorf et al., Carbohydr. Res. 328:623-627 (2000); Steadman et al., Carbohydr. Res. 331: 19-25 (2001)). Fagopyritols are concentrated in the axis and cotyledon tissues of embryos in mature buckwheat seeds (Horbowicz et al., Planta 205:1-11 (1998)). Buckwheat bran, a commercial milling fraction (Steadman et al., J. Cereal Sci. 33:271-278 (2001)), is a rich source of fagopyritols (Steadman et al., J. Agric. Food Chem. 48:2843-2847 (2000)).

Fagopyritols are of considerable interest for the treatment of non-insulin dependent diabetes mellitus (NIDDM) and polycystic ovary syndrome (PCOS), both insulin response disorders. Fagopyritol A1 is isosteric with 2-amino-2-deoxy-α-D-galactopyranosyl-(1→3)-1D-chiro-inositol (Berlin et al., Tetrahedron Lett. 31:1109-1112 (1990)) related to a putative insulin mediator (Berlin et al., Tetrahedron Lett. 31:1109-1112 (1990); Lamer et al., Biochem. Biophys. Res. Comm. 151:1416-1426 (1988)) deficient in subjects with NIDDM (Fonteles et al., Diabetologia 39:731-734 (1996); Lamer et al., Diabetes Rev. 7:217-231 (1999)) and PCOS (Nestler et al., J. Clin. Endocrin. Metab. 83:2001-2005 (1998); Nestler et al., New England J. Med. 340:1314-1320 (1999); Nestler et al., J. Pediatric Endocrin. Metab. 13(Suppl. 5):1295-1298 (2000)).

Enzymes (fagopyritol synthases) catalyzing the biosynthesis of fagopyritols in buckwheat or other plants have not been described. The present invention is directed to overcoming this and other deficiencies in the prior art. SUMMARY OF THE INVENTION The present invention relates to isolated nucleic acid molecules which encode a fagopyritol synthase and the amino acid sequences encoded by such nucleic acid molecules.

Another aspect of the present invention pertains to host cells, expression vectors, transgenic plants, and transgenic plant seeds containing the isolated nucleic acid molecules of the present invention.

The present invention is also directed to a method for producing a fagopyritol, an insulin mediator, an insulin mediator analogue, or an insulin mediator homologue. This method includes providing a fagopyritol synthase, providing a substrate including a galactosyl donor and a galactosyl acceptor, and combining the fagopyritol synthase with the substrate under conditions effective to produce a fagopyritol, an insulin mediator, an insulin mediator analogue, or an insulin mediator homologue.

The fagopyritol synthases of the present invention can be used to produce fagopyritols, insulin mediators, insulin mediator analogues, or insulin mediator homologues which can be used in a pharmaceutical composition which also includes a pharmaceutical carrier. This pharmaceutical composition or, alternatively, the fagopyritols, insulin mediators, insulin mediator analogues, or insulin mediator homologues can be administered to a patient to treat disorders, such as diabetes and PCOS. In addition, the fagopyritol synthases can be used to produce transgenic plants useful for nutraceutical applications.

BRIEF DESCRIPTION OF THE DRAWINGS

FIG. 1 shows the complete nucleotide sequence of the full-length FeGolS-1 cDNA clone (SEQ ID NO:1). The amino acid sequence deduced from the major open reading frame of the cDNA sequence is shown below (SEQ ID NO:2). The translation start (ATG) and termination (TAA) codons are underlined.

FIG. 2 shows the complete nucleotide sequence of the full-length FeGolS-2 cDNA clone (SEQ ID NO:3). The amino acid sequence deduced from the major open reading frame of the cDNA sequence is shown below (SEQ ID NO:4). The translation start (ATG) and termination (TGA) codons are underlined.

FIG. 3 shows the complete nucleotide sequence of the partial FeGolS-3 cDNA clone (SEQ ID NO:5). The amino acid sequence deduced from the major open reading frame of the cDNA sequence is shown below (SEQ ID NO:6). The termination (TGA) codon is underlined.

FIG. 4 shows the complete nucleotide sequence of the soybean GmGolS clone (SEQ ID NO:7). The amino acid sequence deduced from the major open reading frame of the cDNA sequence is shown below (SEQ ID NO:8). The translation start (ATG) and termination (TAA) codons are underlined.

FIG. 6 shows a multiple sequence alignment of the three FeGolS cDNA clones (protein ID: AAM96868, AAM96870, AAM96869; SEQ ID NOS:2, 4, and 6, respectively). Amino acid sequences deduced from the three FeGolS cDNAs were aligned by the CLUSTAL W (1.81) multiple sequence alignment program. The conserved amino acid residues are shown in bold letters. The amino acid sequences corresponding to the PCR primers used in the RT-PCR assays are boxed.

FIG. 7 shows a multiple sequence alignment of GolS amino acid sequences from various plant species. The amino acid sequences deduced from three FeGolS cDNA clones (FeGolS-1 AY126718, FeGolS-2 AY126716, FeGolS-3 AY126717; protein ID AAM96868, AAM96870, AAM96869; SEQ ID NOS: 2, 4, and 6, respectively) and *G. max* (SEQ. ID NO.9) were aligned with those reported from various plant species, including *A. thaliana* (SEQ ID NOS:9 and 10), *B. napus* (SEQ ID NO:11), *P. sativum* (SEQ ID NO:12), *O. sativa* (SEQ ID NO:13), *A. reptans* GolS-1 (SEQ ID NO:14), and *A. reptans* GolS-2 (SEQ ID NO: 15) (indicated in the left margin), by the CLUSTAL W program. The highly conserved amino acid residues are shown in bold letters. The hypothetical manganese-binding motif, DXD, is italicized, and an asterisk marks the conserved serine phosphorylation site. The accession numbers of the sequences used in the comparison are: *Glycine max*, AY126715 (protein ID AAM96867) (BE330777); *Arabidopsis thaliana*, AC002337 and AC009323; *Brassica napus*, AF106954; *Pisum sativum*, PSA243815; *Ajuga reptans* GolS-1, ARE237693; and *Ajuga reptans* GolS-2, ARE237694.

FIGS. 9A-C show fagopyritol synthase products with 20 mM D-chiro-inositol, 20 mM UDP-galactose ("UDP-Gal"), 5 mM $MnCl_2$, 2 mM dithiothreitol ("DTT"), and 50 mM Hepes buffer, pH 7.0. FIGS. 9D-F show galactinol synthase products with 20 mM myo-inositol, 20 mM UDP-Gal, 5 mM $MnCl_2$, 2 mM DTT, and 50 mM Hepes buffer, pH 7.0. Reactions were run 30 to 300 minutes at 30° C. with recombinant protein FeGolS-1 (FIGS. 9A and D), FeGolS-2 (FIGS. 9B and E), and GmGolS (FIGS. 9C and F). Products were analyzed by high resolution gas chromatography. Retention times were: fagopyritol A1 (A1), 24.3 minutes; fagopyritol B1 (B1), 24.8 minutes; and galactinol (Gol), 25.3 minutes.

FIGS. 10A-C are axis tissues. FIGS. 10D-F are cotyledon tissues. Abbreviations in FIGS. 10A-F are as follows: myo-inositol (myo), D-pinitol (Pin), D-chiro-inositol (chiro), fagopyritol B1 (B1), galactinol (Gol), galactopinitol A (GPA), galactopinitol B (GPB), raffinose (Raf), stachyose (Sta), and sucrose (Suc).

FIGS. 12A-C are axis tissues. FIGS. 12D-F are cotyledon tissues. Abbreviations in FIGS. 12A-F are as follows: myo-inositol (myo), D-pinitol (Pin), D-chiro-inositol (chiro), fagopyritol B1 (B1), galactinol (Gol), galactopinitol A (GPA), galactopinitol B (GPB), raffinose (Raf), stachyose (Sta), and sucrose (Suc).

FIGS. 13A-C are axis tissues. FIGS. 13D-F are cotyledon tissues. Abbreviations in FIGS. 13A-F are as follows: myo-inositol (myo), D-pinitol (Pin), D-chiro-inositol (chiro), fagopyritol B1 (B1), galactinol (Gol), galactopinitol A (GPA), galactopinitol B (GPB), raffinose (Raf), stachyose (Sta), and sucrose (Suc).

FIGS. 14A-C are axis tissues. FIGS. 14D-F are cotyledon tissues. Abbreviations in FIGS. 14A-F are as follows: myo-inositol (myo), D-pinitol (Pin), D-chiro-inositol (chiro), fagopyritol B1 (B1), galactinol (Gol), galactopinitol A (GPA), galactopinitol B (GPB), raffinose (Raf), stachyose (Sta), and sucrose (Suc).

FIGS. 15A-C are axis tissues. FIGS. 15D-F are cotyledon tissues. Abbreviations in FIGS. 15A-F are as follows: myo-inositol (myo), D-pinitol (Pin), D-chiro-inositol (chiro), fagopyritol B1 (B1), galactinol (Gol), galactopinitol A (GPA), galactopinitol B (GPB), raffinose (Raf), stachyose (Sta), and sucrose (Suc).

FIGS. 16A-C are axis tissues. FIGS. 16D-F are cotyledon tissues. Abbreviations in FIGS. 16A-F are as follows: myo-inositol (myo), D-pinitol (Pin), D-chiro-inositol (chiro), fagopyritol B1 (B1), galactinol (Gol), galactopinitol A (GPA), galactopinitol B (GPB), raffinose (Raf), stachyose (Sta), and sucrose (Suc).

FIGS. 17A-C are axis tissues. FIGS. 17D-F are cotyledon tissues. Abbreviations in FIGS. 17A-F are as follows: myo-inositol (myo), D-pinitol (Pin), D-chiro-inositol (chiro), fagopyritol B1 (B1), galactinol (Gol), galactopinitol A (GPA), galactopinitol B (GPB), raffinose (Raf), stachyose (Sta), and sucrose (Suc).

FIGS. 18A-C are axis tissues. FIGS. 18D-F are cotyledon tissues. Abbreviations in FIGS. 18A-F are as follows: myo-inositol (myo), D-pinitol (Pin), D-chiro-inositol (chiro), fagopyritol B1 (B1), galactinol (Gol), galactopinitol A (GPA), galactopinitol B (GPB), raffinose (Raf), stachyose (Sta), and sucrose (Suc).

FIG. 19A shows galactinol (retention time 25.8 min) accumulation after enzyme incubation with 25 mM myo-inositol, 25 mM UDP-Gal, 5 mM MnCl$_2$, and 2 mM DTT at 30° C. FIG. 19B shows fagopyritol B1 (retention time 25.3 min) accumulation after enzyme incubation with 25 mM D-chiro-inositol, 25 mM UDP-Gal, 5 mM MnCl$_2$, and 2 mM DTT at 30° C. Reactions were run to near completion to emphasize products.

DETAILED DESCRIPTION OF THE INVENTION

Figure 5:
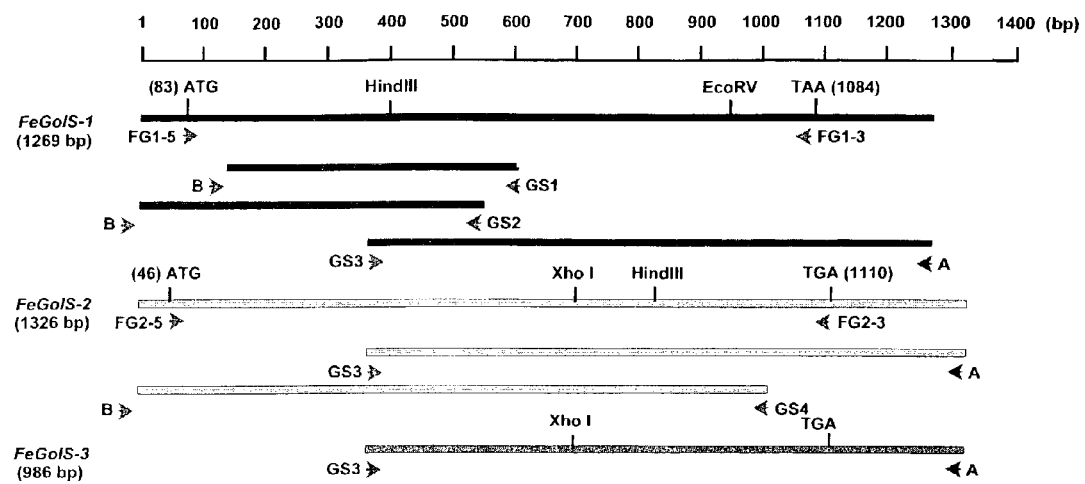
FIG. 5 shows a summary of the cloning of three FeGolS cDNAs. The full length FeGolS-1 (1269 bp) and FeGolS-2 (1326 bp) cDNA clones and the partial FeGolS-3 (986 bp) cDNA clone are diagrammed in scale with the locations of the restriction enzyme recognition sites at the top. For FeGolS-1 and FeGolS-2, the overlapping partial cDNA clones generated by 5' and 3' rapid amplification of cDNA ends-polymerase chain reaction (RACE-PCR) are shown under the full-length clones. The translation start (ATG) and termination (TAA/TGA) codons are shown with their relative positions indicated in the parentheses. The PCR primers used in the RACE-PCR assays are shown with arrows indicating the direction of the PCR amplifications.

The present invention relates to nucleic acid molecules encoding fagopyritol synthase enzymes. Fagopyritol is a general term used herein to mean an unspecified α-galactosyl D-chiro-inositol or its salt or derivative. More particularly, the present invention relates to an isolated nucleic acid molecule encoding a fagopyritol synthase. In accordance with the present invention, the fagopyritol synthase catalyzes the biosynthesis of a fagopyritol. Suitable fagopyritols include fagopyritol A1, particularly fagopyritol A1s have the following Formula I:

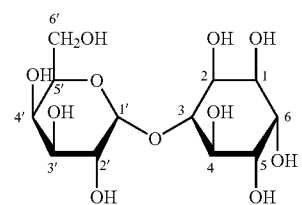

fagopyritol A2, particularly fagopyritol A2s having the following Formula II:

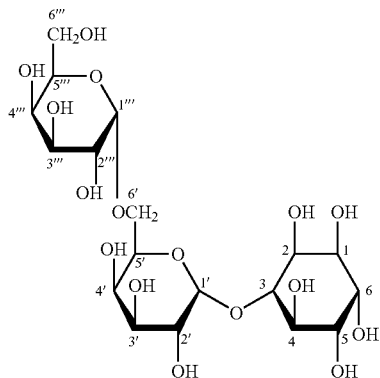

fagopyritol A3, particularly fagopyritol A3s having the following Formula III:

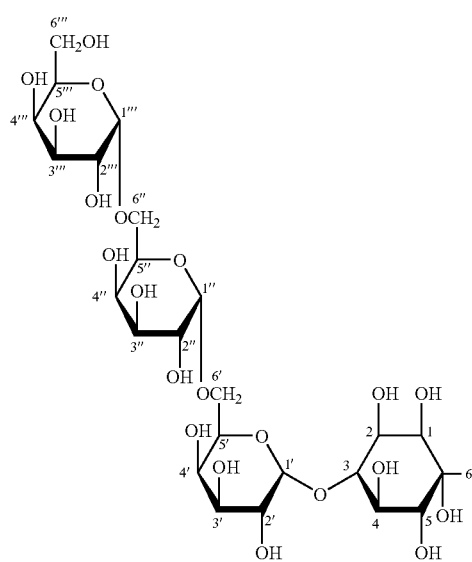

fagopyritol B1, particularly fagopyritol B1s having the following Formula IV:

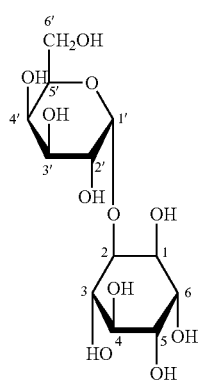

fagopyritol B2, particularly fagopyritol B2s having the following Formula V:

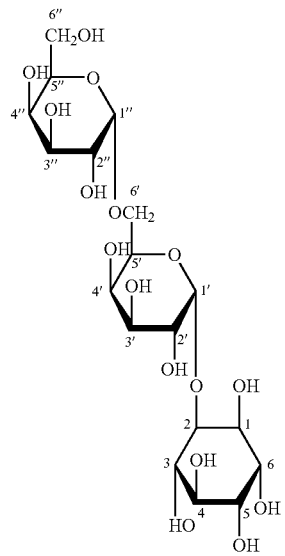

and fagopyritol B3, particularly fagopyritol B3s having the following Formula VI:

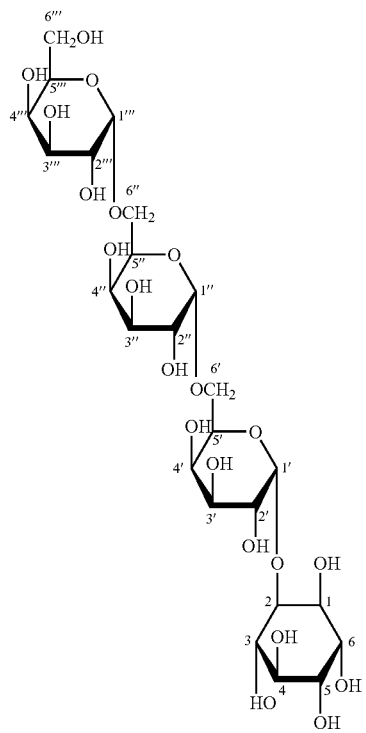

One suitable source of a nucleic acid molecule encoding a fagopyritol synthase enzyme is *Fagopyrum esculentum*.

In a first embodiment, the fagopyritol synthase from *Fagopyrum esculentum* is identified herein as FeGolS-1 and is encoded by a nucleic acid molecule having a nucleotide sequence of SEQ ID NO:1 as follows:

```
gagcacccaa agctctgcta gcaccatatt caaatcctca agaatcatca aatcttccaa     60
ccaatcctca agttccaacc aaatggcacc agaactcatc acaatcggag ccgatcactc    120
gattttgcca gcggaatcgt tgattccggt tgaccgagct acgtgacgt ttctcgccgg    180
gaacggagac tatgtcaagg gagttgtcgg attagcaaag ggactgagga aagtgaaggc    240
tgcttatcct cttgttgtag cggttttacc ggacgttccg ctagagcatc gccgactcct    300
ggaggcgcag ggttgtatcg taagggaaat cgagccgata tacccgccgg aaaacaattg    360
cgagttcgct cacgcatact atgtcatcaa ctactccaag cttcgcatct gggagtttgt    420
ggagtacagt aagatgatat acttggacgg ggacatacag gtgtaccaga acattgacca    480
cctgtttgac cagccggacg gctacttta cgcggtgatg gactgttttt gtgagccatc    540
atggagcaag acgattcagt acaagatcgg atactgccaa cagtgcccgg agaaggtagc    600
gtggccgttg gaggctggcc cgaagccttc tctgtacttc aatgccggat tctttgttta    660
cgagccgagc cttgagactt acaaggatct cattgacact ctcaaagtca cgactcctac    720
ctcctttgcc gagcaggact tcttgaacat gtacttcaag gacaagttca agccactccc    780
catagactac aacttagtct tagccttcct gtggaggcat ccggagaaag ttgaccttaa    840
ccgagtgaag gtagttcact actgtgcggc ggggtctaag ccatggaggt acacgggcaa    900
ggaagagaac atggacagag aagacatcaa attgcttgtg aaaaaatggt gggatatcta    960
caacgacgag tcattggacc tcaagaaacc ggtccattta gtgcagcagc ccacggaggt   1020
gctcaaggcg gcgctctcgg aggctaggcc tgttaaatat gtggctgctc cttccgcagc   1080
ttaagtatcg gcttgtattt ggtaatggtt tttgttttg cgaatgtaaa gtagaaagaa   1140
ggggcgagag tttgtgatat tggggcaatg gggaatggtg cgtataaatg tgtgttgtaa   1200
tggcaactgt ttttacttgg aattatatgt aagaagtaag aatatatgta taaaaaaaaa   1260
aaaaaaaaa                                                            1269
```

The nucleic acid sequence corresponding to SEQ ID NO:1 encodes an isoform of fagopyritol synthase isolated from *Fagopyrum esculentum*, identified herein as FeGolS-1, which has a deduced amino acid sequence corresponding to SEQ ID NO:2, as follows:

```
Met Ala Pro Glu Leu Ile Thr Ile Gly Ala Asp His
 1               5                  10
Ser Ile Leu Pro Ala Glu Ser Leu Ile Pro Val Asp
            15                  20
Arg Ala Tyr Val Thr Phe Leu Ala Gly Asn Gly Asp
 25              30                  35
Tyr Val Lys Gly Val Val Gly Leu Ala Lys Gly Leu
            40                  45
Arg Lys Val Lys Ala Ala Tyr Pro Leu Val Val Ala
 50              55                  60
Val Leu Pro Asp Val Pro Leu Glu His Arg Arg Leu
            65                  70
Leu Glu Ala Gln Gly Cys Ile Val Arg Glu Ile Glu
        75                  80
Pro Ile Tyr Pro Pro Glu Asn Asn Cys Glu Phe Ala
 85              90                  95
His Ala Tyr Tyr Val Ile Asn Tyr Ser Lys Leu Arg
           100                 105
Ile Trp Glu Phe Val Glu Tyr Ser Lys Met Ile Tyr
           110                 115                 120
Leu Asp Gly Asp Ile Gln Val Tyr Gln Asn Ile Asp
           125                 130
His Leu Phe Asp Gln Pro Asp Gly Tyr Phe Tyr Ala
           135                 140
Val Met Asp Cys Phe Cys Glu Pro Ser Trp Ser Lys
145                 150                 155
Thr Ile Gln Tyr Lys Ile Gly Tyr Cys Gln Gln Cys
           160                 165
Pro Glu Lys Val Ala Trp Pro Leu Glu Ala Gly Pro
           170                 175                 180
Lys Pro Ser Leu Tyr Phe Asn Ala Gly Phe Phe Val
           105                 190
Tyr Glu Pro Ser Leu Glu Thr Tyr Lys Asp Leu Ile
           195                 200
Asp Thr Leu Lys Val Thr Thr Pro Thr Ser Phe Ala
205                 210                 215
Glu Gln Asp Phe Leu Asn Met Tyr Phe Lys Asp Lys
           220                 225
```

```
Phe Lys Pro Leu Pro Ile Asp Tyr Asn Leu Val Leu
    230                 235                 240

Ala Phe Leu Trp Arg His Pro Glu Lys Val Asp Leu
                245                 250

Asn Arg Val Lys Val Val His Tyr Cys Ala Ala Gly
            255                 260

Ser Lys Pro Trp Arg Tyr Thr Gly Lys Glu Glu Asn
265                 270                 275

Met Asp Arg Glu Asp Ile Lys Leu Leu Val Lys Lys
                280                 285

Trp Trp Asp Ile Tyr Asn Asp Glu Ser Leu Asp Leu
    290                 295                 300

Lys Lys Pro Val His Leu Val Gln Gln Pro Thr Glu
                305                 310

Val Leu Lys Ala Ala Leu Ser Glu Ala Arg Pro Val
            315                 320

Lys Tyr Val Ala Ala Pro Ser Ala Ala
325                 330
```

The fagopyritol synthase has a molecular mass of from 38 to 41 kDa, and preferably 38.3 kDa. FeGoS-1, isolated from *Fagopyrum esculentum* ("buckwheat"), has a single open reading frame ("ORF") of 1002 bp, extending between nucleotides 83-1084. The starting codon "ATG" is identified at 83-85 bp, with the stop codon "TAA" found between nucleotides 1082-1084, as shown in FIG. 1.

In a second embodiment, the fagopyritol synthase from *Fagopyrum esculentum* is identified herein as FeGolS-2 and is encoded by a nucleic acid molecule having a nucleotide sequence of SEQ ID NO:3 as follows:

```
ttggtttcga acttgatcaa aacctcacaa aaacacgtaa gcaaaatgac ttccgagatg    60
gcgccacaga acataacgaa tgcagaaaga ggagccgagc aagtgaagcc gtcgagccag   120
ccaagccgag cctacgtgac attcttagcc gggaacggtg actacgtgaa gggagttata   180
gggctcgcca aaggcctgag gaaaactcag agcggttacc cgcttgtggt ggcggttctc   240
cctgacgttc cgcaggagca ccgccgtatg ctggtggcgc aaggctgtat aataaaggaa   300
atccagcccg ttaacccgcc cgataaccag actcagtttg ccatggctta ttacgtcatc   360
aactactcca agctccgtat atgggagttt atcgagtata gtaagatgat atatcttgat   420
ggagacatcc aagtttacga caacatcgac cacctcttcg cactaccaga cgggtacttg   480
tacggtgcca tggattgctt ttgcgagaag acttggagtc attcgcttcc atataagatt   540
gggtattgcc aacagtgccc ggacagggtc cagtggcccg aaaggctcgg cccaaaacca   600
acactctact tcaatgcagg gatgttcatc ttcgagccta gcgtttctac ttataatgat   660
ctccttcata cactcgagat caccccctcct acaccttttg ctgagcagga ctttttgaat   720
atgtacttca aggatgtgta cagaccaatt ccgaacgttt acaacttggt attggctttg   780
ttgtggtatc atcctgggtt aatgaagctt gatgaggtta aagtcgttca ctattgtgcc   840
gatggttcaa aaccatggcg gtatacaggg aaggggata acatggacag ggaagacgtt    900
aggatgctag tgaagaagtg gtgggagatt tacgatgatc agtctctcga ccctcagcct   960
aagatggtcg agggcaagaa gttcgacaaa ttagaggagt acagcgagtc cctcgaccac  1020
ccgcccaagg tggcagagga agataagcta gagaagccca tggcagcgat gacaggcttc  1080
agctacgtac acgccccgtc tgctgcctga tttgttgaaa caaggccaag gttccacaaa  1140
tgagggaatc aaaaacctcc tatagtatta tagatcgtat atttctgtta ttgctttcca  1200
attaagcaac taagatgttc atatagtagt tctggaaaat gaatacgggc atagttgtga  1260
acttgtaatc tcattttgtt tttcggaatg ttcaagtatt tcttctaaaa aaaaaaaaa   1320 aaaaaa                                                              1326
```

The nucleic acid sequence corresponding to SEQ ID NO:3 encodes an isoform of fagopyritol synthase isolated from *Fagopyrum esculentum*, identified herein as FeGolS-2, which has a deduced amino acid sequence corresponding to SEQ ID NO:4, as follows:

```
Met Thr Ser Glu Met Ala Pro Gln Asn Ile Thr Asn
 1               5                   10

Ala Glu Arg Gly Ala Glu Gln Val Lys Pro Ser Ser
         15                  20

Gln Pro Ser Arg Ala Tyr Val Thr Phe Leu Ala Gly
 25              30                      35

Asn Gly Asp Tyr Val Lys Gly Val Ile Gly Leu Ala
             40              45

Lys Gly Leu Arg Lys Thr Gln Ser Gly Tyr Pro Leu
     50              55                      60

Val Val Ala Val Leu Pro Asp Val Pro Gln Glu His
                 65              70

Arg Arg Met Leu Val Ala Gln Gly Cys Ile Ile Lys
         75              80

Glu Ile Gln Pro Val Asn Pro Pro Asp Asn Gln Thr
 85              90                      95

Gln Phe Ala Met Ala Tyr Tyr Val Ile Asn Tyr Ser
             100             105

Lys Leu Arg Ile Trp Glu Phe Ile Glu Tyr Ser Lys
     110             115                     120

Met Ile Tyr Leu Asp Gly Asp Ile Gln Val Tyr Asp
                 125             130

Asn Ile Asp His Leu Phe Asp Leu Pro Asp Gly Tyr
             135             140

Leu Tyr Gly Ala Met Asp Cys Phe Cys Glu Lys Thr
145                 150                     155

Trp Ser His Ser Leu Pro Tyr Lys Ile Gly Tyr Cys
             160             165

Gln Gln Cys Pro Asp Arg Val Gln Trp Pro Glu Arg
170                 175                     180

Leu Gly Pro Lys Pro Thr Leu Tyr Phe Asn Ala Gly
                 185             190

Met Phe Ile Phe Glu Pro Ser Val Ser Thr Tyr Asn
            195                 200

Asp Leu Leu His Thr Leu Glu Ile Thr Pro Pro Thr
205                 210                     215

Pro Phe Ala Glu Gln Asp Phe Leu Asn Met Tyr Phe
                220                 225

Lys Asp Val Tyr Arg Pro Ile Pro Asn Val Tyr Asn
            230                 235             240

Leu Val Leu Ala Leu Leu Trp Tyr His Pro Gly Leu
                245                 250

Met Lys Leu Asp Glu Val Lys Val Val His Tyr Cys
            255                 260

Ala Asp Gly Ser Lys Pro Trp Arg Tyr Thr Gly Lys
265                 270                     275

Gly Asp Asn Met Asp Arg Gln Asp Val Arg Met Leu
                280                 285

Val Lys Lys Trp Trp Glu Ile Tyr Asp Asp Glu Ser
            290                 295             300

Leu Asp Pro Gln Pro Lys Met Val Glu Gly Lys Lys
                305                 310

Phe Asp Lys Leu Glu Glu Tyr Ser Glu Ser Leu Asp
            315                 320

His Pro Pro Lys Val Ala Glu Glu Asp Lys Leu Glu
325                 330                     335

Lys Pro Met Ala Ala Met Thr Gly Phe Ser Tyr Val
                340                 345

His Ala Pro Ser Ala Ala
350
```

The fagopyritol synthase has a molecular mass of from 38 to 41 kDa, and preferably 40.7 kDa. FeGoS-2, isolated from *Fagopyrum esculentum*, has a single ORF of 1065 bp, extending between nucleotides 46-1110. The starting codon "ATG" is identified at 46-48 bp, with the stop codon "TGA" found between nucleotides 1108-1110, as shown in FIG. 2.

In a third embodiment, the fagopyritol synthase from *Fagopyrum esculentum* is identified herein as FeGolS-3 and comprises a nucleic acid molecule having a nucleotide sequence of SEQ ID NO:5 (see FIG. 3) as follows:

```
gctcacgcat actatgtcat caactactcc aagctccgta tatgggagtt tatcgagtat     60
agtaagatga tatatcttga tggagacatc caagtttacg acaacatcga ccacctcttc    120
gacctaccag acgggtactt gtacggtgcc atggattgct tttgcgagaa gacttggagt    180
cattcgcttc catataagat tgggtattgc caacagtgcc cggacagggt ccagtggccc    240
gaaaggctcg gcccaaaacc aacactctac ttcaatgcag ggatgttcat cttcgagcct    300
agcgtttcta cttataatga tctccttcat acactcgaga tcaccctcc tacaccttt     360
gctgagcagg actttttgaa tatgtacttc aaggatgtgt acagaccaat tccgaacgtg    420
tacaacttgg tattggcttt gttgtggtat catcctgggt taatgaatct tgatgaggtt    480
aaagtcgttc actattgtgc cgatggttca aaaccatggc ggtatacagg aagggggat    540
aacatggaca gggaagacgt taggatgcta gtgaagaagt ggtgggagat ctacgatgat    600
cagtctctcg accctcagcc taaggtggtc gagggcaaga agttcgacaa attagagtac    660
```

```
agcgagtccc tcgaccaccc gcctaaggtg gcagaggaag ataagttaga gaagcccatg    720
gcggcgatga cagggttcag ctacgtacac gccccgtctg ctgcctgact tgttgaaaca    780
aggccaaggt tccacaaatg agggaatcaa aaacctccta tagtattata gatcgtatat    840
ttctgttatt gctttccaat taagcaacta agatgttcat atagtagttc tggaaaatga    900
aaacgggcat agttgtgaac ttgtaatctc attttgtttt tcggaatgtg caagtatttc    960
ttctaaataa aaaaaaaaaa aaaaaa                                          986
```

The nucleic acid sequence corresponding to SEQ ID NO:5 encodes an isoform of fagopyritol synthase isolated from *Fagopyrum esculentum*, identified herein as FeGolS-3, which comprises a deduced amino acid sequence corresponding to SEQ ID NO:6, as follows:

```
Ala His Ala Tyr Tyr Val Ile Asn Tyr Ser Lys Leu
  1               5                        10

Arg Ile Trp Glu Phe Ile Glu Tyr Ser Lys Met Ile
            15                   20

Tyr Leu Asp Gly Asp Ile Gln Val Tyr Asp Asn Ile
 25                  30                        35

Asp His Leu Phe Asp Leu Pro Asp Gly Tyr Leu Tyr
                40                   45

Gly Ala Met Asp Cys Phe Cys Glu Lys Thr Trp Ser
         50                  55                  60

His Ser Leu Pro Tyr Lys Ile Gly Tyr Cys Gln Gln
                65                   70

Cys Pro Asp Arg Val Gln Trp Pro Gln Arg Leu Gly
             75                   80

Pro Lys Pro Thr Leu Tyr Phe Asn Ala Gly Met Phe
 85                  90                        95

Ile Phe Glu Pro Ser Val Ser Thr Tyr Asn Asp Leu
                100                 105

Leu His Thr Leu Glu Ile Thr Pro Pro Thr Pro Phe
         110                 115                120

Ala Glu Gln Asp Phe Leu Asn Met Tyr Phe Lys Asp
                125                 130

Val Tyr Arg Pro Ile Pro Asn Val Tyr Asn Leu Val
                135                 140

Leu Ala Leu Leu Trp Tyr His Pro Gly Leu Met Asn
145                 150                          155

Leu Asp Glu Val Lys Val Val His Tyr Cys Ala Asp
                160                 165

Gly Ser Lys Pro Trp Arg Tyr Thr Gly Lys Gly Asp
                170                 175                 180

Asn Met Asp Arg Glu Asp Val Arg Met Leu Val Lys
                     185                 190

Lys Trp Trp Glu Ile Tyr Asp Asp Gln Ser Leu Asp
                195                 200

Pro Gln Pro Lys Val Val Glu Gly Lys Lys Phe Asp
205                 210                          215

Lys Leu Glu Tyr Ser Glu Ser Leu Asp His Pro Pro
                220                 225

Lys Val Ala Glu Glu Asp Lys Leu Glu Lys Pro Met
            230                 235                 240

Ala Ala Met Thr Gly Phe Ser Tyr Val His Ala Pro
                     245                 250

Ser Ala Ala
         255
```

Another suitable source of a nucleic acid molecule encoding a fagopyritol synthase enzyme is *Glycine max*. A fagopyritol synthase from *Glycine max* is identified herein as GmGolS and is encoded by a nucleic acid molecule having a nucleotide sequence of SEQ ID NO:7 as follows:

```
agccaaaagt ttgttttcat agtgtgtttt gtttcccaaa tcctactctt gtgaccacaa    60
cccttcctcc tctttctttt gaaacctctt tttttctatt ccccaaccaa acaagcaaac   120
gctactcact catcatcact gagatcatgg ctcctaatat caccactgtc aaaaccacca   180
tcaccgacgc tcaagccaag gtcgccaccg atcatggtcg tgcctacgtc accttcctcg   240
ccggaaacgg tgactatgtg aaaggtgtcg ttggcttggc aaaaggtctg agaaaagtga   300
agagcatgta ccctctggtg gttgcagtgc tacccgatgt tccccaagat caccgcaaca   360
ttctcacctc ccaaggttgc attgttagag agattgagcc cgtgtacccc ccagagaatc   420
aaacccagtt tgccatggca tattacgtca tcaactattc caagctacgt atttgggagt   480 tgtggagta cagcaagatg atataccta g acggtgatat ccaagttttt gacaacattg   540
accacttgtt tgacttgcct gataactact tctatgcggt gatggactgt ttctgtgagc   600
```

```
caacttgggg ccacactaaa caatatcaga tcggttactg ccagcagtgc ccccataagg    660
ttcagtggcc cactcacttt gggcccaaac ctcctctcta tttcaatgct ggcatgtttg    720
tgtatgagcc caatttggct acttaccgtg acctccttca aacagtccaa gtcacccagc    780
ccacttcctt tgctgaacag gattttttga acatttactt caaggacaaa tataggccaa    840
ttcctaatgt ctacaatctt gtgctggcca tgctgtggcg tcaccctgag aacgttgagc    900
ttgacaaagt taaagtggtt cactactgtg ctgctgggtc taagccttgg aggtacactg    960
ggaaggagga gaatatggag agagaagata tcaagatgtt agtgaaaaag tggtgggata    1020
tatatgagga tgagactttg gactacaaca atccactcaa tgtggataag ttcactgcgg    1080
cacttatgga ggttggtgaa gtcaagttcg tccgtgcccc atctgctgct taagagtgtc    1140
tttggaaatc aagtgtgatc caagtacatg tacaaagtca tacatcatta cattaacttt    1200
tatgtatttc taaaagtcat acatcattac attaagtttt atgtatttct aaagtcttaa    1260
gacttaagag gacctttttt atgtgtcccg gctttcttt ttttcttttt ccaattctgt    1320
cattgtaaag caggtgaata ccggtatcct taattttata aatggatatg aattttattt    1380
tgcaaaaaaa aaaaaaaaaa aaaaaa    1406
```

The nucleic acid sequence corresponding to SEQ ID NO:7 encodes an isoform of fagopyritol synthase isolated from *Glycine max*, identified herein as GmGolS, which has a deduced amino acid sequence corresponding to SEQ ID NO: 8, as follows:

```
Met Ala Pro Asn Ile Thr Thr Val Lys Thr Thr Ile
 1               5                  10

Thr Asp Ala Gln Ala Lys Val Ala Thr Asp His Gly
         15                  20

Arg Ala Tyr Val Thr Phe Leu Ala Gly Asn Gly Asp
 25              30                  35

Tyr Val Lys Gly Val Val Gly Leu Ala Lys Gly Leu
             40                  45

Arg Lys Val Lys Ser Met Tyr Pro Leu Val Val Ala
 50              55                  60

Val Leu Pro Asp Val Pro Gln Asp His Arg Asn Ile
             65                  70

Leu Thr Ser Gln Gly Cys Ile Val Arg Glu Ile Glu
         75                  80

Pro Val Tyr Pro Pro Glu Asn Gln Thr Gln Phe Ala
 85              90                  95

Met Ala Tyr Tyr Val Ile Asn Tyr Ser Lys Leu Arg
             100                 105

Ile Trp Glu Phe Val Glu Tyr Ser Lys Met Ile Tyr
     110             115                 120

Leu Asp Gly Asp Ile Gln Val Phe Asp Asn Ile Asp
             125                 130

His Leu Phe Asp Leu Pro Asp Asn Tyr Phe Tyr Ala
         135                 140

Val Met Asp Cys Phe Cys Glu Pro Thr Trp Gly His
 145             150                 155

Thr Lys Gln Tyr Gln Ile Gly Tyr Cys Gln Gln Cys
             160                 165

Pro His Lys Val Gln Trp Pro Thr His Phe Gly Pro
         170                 175                 180

Lys Pro Pro Leu Tyr Phe Asn Ala Gly Met Phe Val
             185                 190

Tyr Glu Pro Asn Leu Ala Thr Tyr Arg Asp Leu Leu
         195                 200

Gln Thr Val Gln Val Thr Gln Pro Thr Ser Phe Ala
 205             210                 215

Glu Glu Asp Phe Leu Asn Ile Tyr Phe Lys Asp Lys
             220                 225

Tyr Arg Pro Ile Pro Asn Val Tyr Asn Leu Val Leu
 230             235                 240

Ala Met Leu Trp Arg His Pro Glu Asn Val Glu Leu
             245                 250

Asp Lys Val Lys Val Val His Tyr Cys Ala Ala Gly
         255                 260

Ser Lys Pro Trp Arg Tyr Thr Gly Lys Glu Glu Asn
 265             270                 275

Met Glu Arg Glu Asp Ile Lys Met Leu Val Lys Lys
             280                 285

Trp Trp Asp Ile Tyr Glu Asp Glu Thr Leu Asp Tyr
 290             295                 300

Asn Asn Pro Leu Asn Val Asp Lys Phe Thr Ala Ala
             305                 310

Leu Met Glu Val Gly Glu Val Lys Phe Val Arg Ala
         315                 320

Pro Ser Ala Ala
 325
```

(see FIG. 4). The fagopyritol synthase has a molecular mass of approximately 38.0 kDa.

Other suitable sources of nucleic acid molecules encoding fagopyritol synthases include any plant that expresses galactinol synthase (i.e., any plant that accumulates raffinose series of oligosaccharides), including, but not limited to, sugar beet, vetch, beans, legumes, cereals and grasses, cucurbits, and Brassicas (see, e.g., Kuo et al., J. Agricul. Food Chem. 36:32-36 (1988), which is hereby incorporated by reference in its entirety).

Fragments of the above fagopyritol synthase enzymes are encompassed by the present invention.

Suitable fragments can be produced by several means. In one method, subclones of the genes encoding the fagopyritol synthase enzymes of the present invention are produced by conventional molecular genetic manipulation by subcloning gene fragments. The subclones then are expressed in vitro or in vivo in bacterial cells to yield a smaller protein or peptide.

In another approach, based on knowledge of the primary structure of the protein, fragments of a fagopyritol synthase enzyme encoding gene may be synthesized by using the PCR technique together with specific sets of primers chosen to represent particular portions of the protein. These then would be cloned into an appropriate vector for increased expression of a truncated peptide or protein.

Chemical synthesis can also be used to make suitable fragments. Such a synthesis is carried out using known amino acid sequences for a fagopyritol synthase enzyme being produced. Alternatively, subjecting a full length fagopyritol synthase enzyme to high temperatures and pressures will produce fragments. These fragments can then be separated by conventional procedures (e.g., chromatography, SDS-PAGE).

Another example of suitable fragments of the nucleic acids of the present invention are fragments of the genes which have been identified as conserved ("con") regions of the proteins, or alternatively, those portions of nucleotide sequences that have been identified as variable ("var") regions. Sequences identified using DNAStar Mega alignment program as either variable or conserved in a gene can be amplified using standard PCR methods using forward and reverse primers designed to amplify the region of choice and which include a restriction enzyme sequence to allow ligation of the PCR product into a vector of choice. Combinations of amplified conserved and variable region sequences can be ligated into a single vector to create a "cassette" which contains a plurality of DNA molecules in one vector.

Mutations or variants of the above polypeptides or proteins are encompassed by the present invention. Variants may be made by, for example, the deletion or addition of amino acids that have minimal influence on the properties, secondary structure, and hydropathic nature of an enzyme. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

Also suitable as an isolated nucleic acid molecule according to the present invention is a nucleic acid molecule having a nucleotide sequence that is at least 55% similar, preferably at least 80% similar, and most preferably, at least 90% similar, to the nucleotide sequence of SEQ ID NO:1, SEQ ID NO:3, SEQ ID NO:5, or SEQ ID NO:7 by basic BLAST using default parameters analysis.

Suitable nucleic acid molecules are those that hybridize to a nucleic acid molecule comprising a nucleotide sequence of SEQ ID No:1, SEQ ID NO:3, SEQ ID NO:5, or SEQ ID NO:7 under stringent conditions. For the purposes of defining the level of stringency, reference can conveniently be made to Sambrook et al., *Molecular Cloning: a Laboratory Manual*, 2$^{nd}$ Edition, Cold Spring Harbor, N.Y., Cold Spring Harbor Laboratory Press, at 11.45 (1989). An example of low stringency conditions is 4-6×SSC/0.1-0.5% w/v SDS at 37°-45° C. for 2-3 hours. Depending on the source and concentration of the nucleic acid involved in the hybridization, alternative conditions of stringency may be employed such as medium stringent conditions. Examples of medium stringent conditions include 1-4×SSC/0.25% w/v SDS at ≧45° C. for 2-3 hours. An example of high stringency conditions includes 0.1-1×SSC/0.1% w/v SDS at 60° C. for 1-3 hours. The skilled artisan is aware of various parameters which may be altered during hybridization and washing and which will either maintain or change the stringency conditions. Other examples of high stringency conditions include: 4-5×SSC/0.1% w/v SDS at 54° C. for 1-3 hours and 4×SSC at 65° C., followed by a washing in 0.1×SSC at 65° C. for about one hour. Alternatively, an exemplary stringent hybridization condition is in 50% formamide, 4×SSC, at 42° C. Still another example of stringent conditions include hybridization at 62° C. in 6×SSC, 0.05×BLOTTO, and washing at 2×SSC, 0.1% SDS at 62° C.

The precise conditions for any particular hybridization are left to those skilled in the art because there are variables involved in nucleic acid hybridizations beyond those of the specific nucleic acid molecules to be hybridized that affect the choice of hybridization conditions. These variables include: the substrate used for nucleic acid hybridization (e.g., charged vs. non-charged membrane); the detection method used (e.g., radioactive vs. chemiluminescent); and the source and concentration of the nucleic acid involved in the hybridization. All of these variables are routinely taken into account by those skilled in the art prior to undertaking a nucleic acid hybridization procedure.

A fagopyritol synthase enzyme of the present invention is preferably produced in purified form (e.g., at least about 80%, more preferably 90% pure) by conventional techniques. One example of a suitable technique is set forth in the Examples herein. Alternatively, a fagopyritol synthase enzyme of the present invention is secreted into the growth medium of recombinant host cells. To isolate the fagopyritol synthase enzyme, a protocol involving a host cell such as *Escherichia coli* may be used, in which protocol the *E. coli* host cell carrying a recombinant plasmid is propagated, homogenized, and the homogenate is centrifuged to remove bacterial debris. The supernatant is then subjected to sequential ammonium sulfate precipitation. The fraction containing the fagopyritol synthase enzyme of the present invention is subjected to gel filtration in an appropriately sized dextran or polyacrylamide column to separate the proteins or polypeptides. If necessary, the protein fraction may be further purified by high performance liquid chromatography ("HPLC").

The nucleic acid molecule encoding the fagopyritol synthase enzyme of the present invention, or a suitable portion thereof, can be incorporated into host cells using conventional recombinant DNA technology. Generally, this involves inserting the nucleic acid molecule into an expression system to which the nucleic acid molecule is heterologous (i.e. not normally present). The expression system contains the necessary elements for the transcription and translation of the inserted protein-coding sequences.

The present invention also relates to an expression vector containing a nucleic acid molecule encoding a fagopyritol synthase enzyme of the present invention. The nucleic acid molecules of the present invention may be inserted into any of the many available expression vectors and cell systems using reagents that are well known in the art. In preparing a DNA vector for expression, the various DNA sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. Numerous plasmids, referred to as transformation vectors, are available for transformation. The selection of a vector will depend on the preferred transformation technique and target cells for transfection.

Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC11, SV 40, pBluescript II SK+/− or KS+/− (see "Stratagene Cloning Systems" Catalog (1993) from Stratagene, La Jolla, Calif., which is hereby incorporated by reference in its entirety), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference in its entirety), and any derivatives thereof. Any appropriate vectors now known or later described for genetic transformation are suitable for use with the present invention. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Second Edition, Cold Spring Harbor Press, NY (1989), and Ausubel, F. M. et al. (1989) *Current Protocols in Molecular Biology*, John Wiley & Sons, New York, N.Y., which are hereby incorporated by reference in their entirety.

U.S. Pat. No. 4,237,224 issued to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Thus, certain "control elements" or "regulatory sequences" are also incorporated into the plasmid-vector constructs of the present invention. These include non-transcribed regions of the vector and 5' and 3' untranslated regions, which interact with host cellular proteins to carry out transcription and translation. Such elements may vary in their strength and specificity. Depending on the vector system and host utilized, any number of suitable transcription and/or translation elements, including constitutive, inducible, and repressible promoters, as well as minimal 5' promoter elements may be used. A constitutive promoter is a promoter that directs expression of a gene throughout the development and life of an organism. An inducible promoter is a promoter that is capable of directly or indirectly activating transcription of one or more DNA sequences or genes in response to an inducer. In the absence of an inducer, the DNA sequences or genes will not be transcribed or will only be minimally transcribed.

The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Promotors vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promotor, trp promotor, recA promotor, ribosomal RNA promotor, the $P_R$ and $P_L$ promotors of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Other examples of some constitutive promoters that are widely used for inducing expression of transgenes include the nopoline synthase (NOS) gene promoter, from *Agrobacterium tumefaciens*, (U.S. Pat. No. 5,034,322 issued to Rogers et al., which is hereby incorporated by reference in its entirety), the cauliflower mosaic virus (CaMV) 35S and 19S promoters (U.S. Pat. No. 5,352,605 issued to Fraley et al., which is hereby incorporated by reference in its entirety), the enhanced CaMV35S promoter ("enh CaMV35S"), the figwort mosaic virus full-length transcript promoter ("FMV35S"), those derived from any of the several actin genes, which are known to be expressed in most cells types (U.S. Pat. No. 6,002,068 issued to Privalle et al., which is hereby incorporated by reference in its entirety), and the ubiquitin promoter, which is a gene product known to accumulate in many cell types. Examples of constitutive promoters for use in mammalian cells include the RSV promoter derived from Rous sarcoma virus, the CMV promoter derived from cytomegalovirus, β-actin and other actin promoters, and the EF1α promoter derived from the cellular elongation factor 1α gene.

Bacterial host cell strains and expression vectors may be chosen which inhibit the action of the promoter unless specifically induced. In certain operations, the addition of specific inducers is necessary for efficient transcription of the inserted nucleic acid. For example, the lac operon is induced by the addition of lactose or IPTG (isopropylthio-beta-D-galactoside). A variety of other operons, such as trp, pro, etc., are under different controls.

Other examples of some inducible promoters, induced, for examples by a chemical agent, such as a metabolite, growth regulator, herbicide or phenolic compound, or a physiological stress/physical means, such as cold, heat, salt, toxins, or through the action of a pathogen or disease agent such as a virus or fungus, include a glucocorticoid-inducible promoter (Schena et al., *Proc. Natl. Acad. Sci.* 88:10421-5 (1991), which is hereby incorporated by reference in its entirety), the heat shock promoter ("Hsp"), IPTG or tetracycline ("Tet on" system), the metallothionine promoter, which is activated by heavy metal ions, and hormone-responsive promoters, which are activated by treatment of certain hormones. A host cell containing an inducible promoter may be exposed to an inducer by externally applying the inducer to the cell. In addition, "tissue-specific" promoters can be used, which are promoters that function in a tissue specific manner to regulate the gene of interest within selected tissues of the host. Examples of such tissue specific promoters include seed, flower, or root specific promoters as are well known in the field (e.g., U.S. Pat. No. 5,750,385 to Shewmaker et al., which is hereby incorporated by reference in its entirety). Promoters of the nucleic acid construct of the present invention may be either homologous (derived from the same species as the host cell) or heterologous (derived from a different species than the host cell).

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in E. coli requires an SD sequence about 7-9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the E. coli tryptophan E, D, C, B or A genes. Additionally, any SD-ATG combination produced by recombinant DNA or other techniques involving incorporation of synthetic nucleotides may be used.

The constructs of the present invention also include an operable 3' regulatory region, selected from among those which are capable of providing correct transcription termination and polyadenylation of mRNA for expression in the host cell of choice, operably linked to a DNA molecule which encodes for a protein of choice. A number of 3' regulatory regions are known in the art. Virtually any 3' regulatory region known to be operable in the host cell of choice would suffice for proper expression of the coding sequence of the nucleic acid of the present invention.

In one aspect of the present invention, the nucleic acid molecule of the present invention is incorporated into an appropriate vector in the sense direction, such that the open reading frame is properly oriented for the expression of the encoded protein under control of a promoter of choice. This involves the inclusion of the appropriate regulatory elements into the DNA-vector construct. These include non-translated regions of the vector, useful promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used.

A nucleic acid molecule of the preset invention, promoter of choice, an appropriate 3' regulatory region, and, if desired, a reporter gene, can be incorporated into a vector-expression system which contains the nucleic acids of the present invention, or suitable fragments thereof, using standard cloning techniques as described in Sambrook et al., *Molecular Cloning: A Laboratory Manual*, Second Edition, Cold Spring Harbor Press, NY (1989), and Ausubel et al. (1989) *Current Protocols in Molecular Biology*, John Wiley & Sons, New York, N.Y., which are hereby incorporated by reference in their entirety. The transcriptional and translational elements are operably linked to the nucleic acid molecule of the present invention or a fragment thereof, meaning that the resulting vector expresses the fagopyritol synthase when placed in a suitable host cell.

Once an isolated DNA molecule encoding a fagopyritol synthase enzyme has been cloned into an expression vector, it is ready to be incorporated into a host cell. Such incorporation can be carried out by the various forms of transformation noted above, depending upon the vector/host cell system. Recombinant molecules can be introduced into cells via transformation, particularly transduction, conjugation, mobilization, or electroporation. The nucleic acid sequences are cloned into the host cell using standard cloning procedures known in the art, as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable host cells include, but are not limited to, bacteria, virus, yeast, mammalian cells, insect, plant, and the like.

Thus, the present invention also relates to a host cell incorporating one or more of the isolated nucleic acid molecules of the present invention. In one embodiment, the isolated nucleic acid molecule is heterologous to the host cell. Such incorporation can be carried out by the various forms of transformation noted above, depending upon the vector/host system, and using the various host cells described above.

Methods of transformation may result in transient or stable expression of the DNA under control of the promoter. Preferably, the nucleic acid of the present invention is stably inserted into the genome of the host cell as a result of the transformation, although transient expression can serve an important purpose.

One approach to transforming host cells with a nucleic acid molecule of the present invention is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference in their entirety. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells. Other variations of particle bombardment, now known or hereafter developed, can also be used.

Transient expression in protoplasts allows quantitative studies of gene expression, because the population of cells is very high (on the order of $10^6$). To deliver DNA inside protoplasts, several methodologies have been proposed, but the most common are electroporation (Fromm et al., *Proc. Natl. Acad. Sci. USA* 82:5824-5828 (1985), which is hereby incorporated by reference in its entirety) and polyethylene glycol (PEG) mediated DNA uptake (Krens et al., *Nature* 296:72-74 (1982), which is hereby incorporated by reference in its entirety). During electroporation, the DNA is introduced into the cell by means of a reversible change in the permeability of the cell membrane due to exposure to an electric field. PEG transformation introduces the DNA by changing the elasticity of the membranes. Unlike electroporation, PEG transformation does not require any special equipment and transformation efficiencies can be equally high. Another appropriate method of introducing the nucleic acid molecule of the present invention into a host cell is fusion of protoplasts with other entities, either minicells, cells, lysosomes, or other fusible lipid-surfaced bodies that contain the chimeric gene (Fraley, et al., *Proc. Natl. Acad. Sci. USA* 76:3348-52 (1979), which is hereby incorporated by reference in its entirety).

Stable transformants are preferable for the methods of the present invention. An appropriate method of stably introducing the nucleic acid molecule into plant cells is to infect a plant cell with *Agrobacterium tumefaciens* or *Agrobacterium rhizogenes* previously transformed with a DNA construct of the present invention. Under appropriate conditions known in the art, the transformed plant cells are grown to form shoots or roots, and develop further into plants.

Plant tissues suitable for transformation include without limitation, floral buds, leaf tissue, root tissue, meristems, zygotic and somatic embryos, megaspores, callus, protoplasts, tassels, pollen, embryos, anthers, and the like. The means of transformation chosen is that most suited to the tissue to be transformed.

Suitable plants include dicots and monocots. Monocots suitable for the present invention include Gramineae (e.g., grass, corn, grains, bamboo, sugar cane), Liliaceae (e.g., onion, garlic, asparagus, tulips, hyacinths, day lily, and aloes), Iridaceae (e.g., iris, gladioli, freesia, crocus, and watsonia), and Orchidacea (e.g., orchid). Examples of dicots suitable for the present invention include Salicaceae (e.g., willow, and poplar), Ranunculaceae (e.g., *Delphinium, Paeonia, Ranunculus, Anemone, Clematis*, columbine, and marsh marigold), Magnoliaceae (e.g., tulip tree and *Magnolia*), Cruciferae (e.g., mustards, cabbage, cauliflower, broccoli, brussel sprouts, kale, kohlrabi, turnip, and radish), Rosaceae (e.g., strawberry, blackberry, peach, apple, pear, quince, cherry, almond, plum, apricot, and rose), Leguminosae (e.g., pea, bean, peanut, alfalfa, clover, vetch, redbud, broom, wisteria, lupine, black locust, and acacia), Malvaceae (e.g., cotton, okra, and mallow), Umbelliferac (e.g., carrot, parsley, parsnips, and hemlock), Labiatae (e.g., mint, peppermints, spearmint, thyme, sage, and lavender), Solanaceae (e.g., potato, tomato, pepper, eggplant, and *Petunia*), Cucurbitaceae (e.g., melon, squash, pumpkin, and cucumber), Compositae (e.g., sunflower, endive, artichoke, lettuce, safflower, aster, marigold, dandelions, sage brush, *Dalia, Chrysanthemum*, and *Zinna*), and Rubiaceae (e.g., coffee).

After transformation, the transformed plant cells can be selected and regenerated. Preferably, transformed cells are first identified using a selection marker simultaneously introduced into the host cells along with the DNA construct of the present invention. Suitable selection markers include, without limitation, markers encoding for antibiotic resistance, such as the nptII gene which confers kanamycin resistance (Fraley, et al., *Proc. Natl. Acad. Sci. USA* 80:4803-4807 (1983), which is hereby incorporated by reference in its entirety), and the genes which confer resistance to gentamycin, G418, hygromycin, streptomycin, spectinomycin, tetracycline, chloramphenicol, and the like. Any known antibiotic-resistance marker can be used to transform and select transformed host cells in accordance with the present invention. Cells or tissues are grown on a selection medium containing the appropriate antibiotic, whereby generally only those transformants expressing the antibiotic resistance marker continue to grow. Other types of markers are also suitable for inclusion in the expression cassette of the present invention. For example, a gene encoding for herbicide tolerance, such as tolerance to sulfonylurea is useful, or the dhfr gene, which confers resistance to methotrexate (Bourouis et al., *EMBO J.* 2:1099-1104 (1983), which is hereby incorporated by reference in its entirety). Similarly, "reporter genes," which encode for enzymes providing for production of a compound identifiable are suitable. The most widely used reporter gene for gene fusion experiments has been uidA, a gene from *Escherichia coli* that encodes the β-glucuronidase protein, also known as GUS (Jefferson et al., *EMBO J.* 6:3901-3907 (1987), which is hereby incorporated by reference in its entirety). Similarly, enzymes providing for production of a compound identifiable by luminescence, such as luciferase, are useful. The selection marker employed will depend on the target species; for certain target species, different antibiotics, herbicide, or biosynthesis selection markers are preferred.

Once a recombinant plant cell or tissue has been obtained, it is possible to regenerate a full-grown plant therefrom. It is known that practically all plants can be regenerated from cultured cells or tissues, including but not limited to, all major species of sugarcane, sugar beets, cotton, fruit trees, and legumes. Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

Plant regeneration from cultured protoplasts is described in Evans, et al., *Handbook of Plant Cell Cultures, Vol.* 1: (MacMillan Publishing Co., New York, 1983); and Vasil I. R. (ed.), *Cell Culture and Somatic Cell Genetics of Plants*, Acad. Press, Orlando, Vol. I, 1984, and Vol. III (1986), which are hereby incorporated by reference in their entirety.

After the DNA construct is stably incorporated in transgenic plants, it can be transferred to other plants by sexual crossing or by preparing cultivars. With respect to sexual crossing, any of a number of standard breeding techniques can be used depending upon the species to be crossed. Cultivars can be propagated in accord with common agricultural procedures known to those in the field. Alternatively, transgenic seeds or propagules (e.g., cuttings) are recovered from the transgenic plants. The seeds can then be planted in the soil and cultivated using conventional procedures to produce transgenic plants.

Another aspect of the present invention relates to a method for producing a fagopyritol, an insulin mediator, an insulin mediator analogue, an insulin mediator homologue, or an insulin mediator inhibitor. As used herein, fagopyritols, insulin mediators, insulin mediator analogues, insulin mediator homologues, and insulin mediator inhibitors include salts and derivatives thereof.

Studies have been completed that link Type II diabetes and PCOS to deficiencies in insulin mediators composed of galactosamine D-chiro-inositol. Although their functions have yet to be fully characterized, it is known that insulin mediators act as second messengers of insulin action, and they are believed to be inositol phosphoglycans bound to cell membranes (Lamer et al., *Diabetes Reviews* 7:217-231 (1999), which is hereby incorporated by reference in its entirety). In the presence of insulin, these mediators are released and may activate glycogen synthesis. It has been found that feeding D-chiro-inositol to women with PCOS increased insulin response and ovulatory function (Nestler et al., *N. Engl. J. Med.* 340:1314-1320 (1999), which is hereby incorporated by reference in its entirety). Another study has also shown that insulin resistance has been associated with abnormal D-chiro-inositol metabolism (Ortmeyer et al., *Endocrinology* 132:640-645 (1993), which is hereby incorporated by reference in its entirety). Thus, synthesis of insulin mediators containing D-chiro-inositol is of importance in order to determine a treatment for Type II diabetes and PCOS.

This method of the present invention includes providing a fagopyritol synthase, providing a substrate including a galactosyl donor and a galactosyl acceptor, and combining the fagopyritol synthase with the substrate under conditions effective to produce a fagopyritol, an insulin mediator, an insulin mediator analogue, an insulin mediator homologue, or an insulin mediator inhibitor.

Suitable fagopyritols which can be produced by the above method of the present invention are described above.

Suitable insulin mediators, insulin mediator analogues, insulin mediator homologues, and insulin mediator inhibitors which can be produced by the above method of the present invention include, but are not limited to, galactosamine-D-chiro-inositols, galactosamine L-chiro-inositols, galactosamine-myo-inositols, galactosamine-scyllo-inositols, galactosamine-bornesitols, galactose-D-chiro-inositols, galactose L-chiro-inositols, galactose-myo-inositols, galactose-scyllo-inositols, galactose-bornesitols, glucose-D-chiro-inositols, glucose L-chiro-inositols, glucose-myo-inositols, glucose-scyllo-inositols, glucose-bornesitols, glucosamine-D-chiro-inositols, glucosamine L-chiro-inositols, glucosamine-myo-inositols, glucosamine-scyllo-inositols, and glucoseamine-bornesitols.

Suitable galactosyl donors include, but are not limited to, UDP-galactose, UDP-galactosamine, UDP-glucose, and UDP-glucosamine, which may be used with the enzymes described herein or enzyme mutants.

Suitable galactosyl acceptors include, but are not limited to, D-chiro-inositol, L-chiro-inositol, myo-inositol, bornesitol, and scyllo-inositol.

The fagopyritol synthase and substrate are combined to produce a fagopyritol, an insulin mediator, an insulin mediator analogue, or an insulin mediator homologue. Suitable conditions are determined by the fagopyritol synthase and substrate used, and include suitable amounts of $Mn^{2+}$ (e.g., approximately 1-15 mM $MnCl_2$, preferably 5 mM $MnCl_2$) and suitable amounts of reducing agents, such as DTT and mercaptoethanol. One example of suitable conditions is disclosed in the enzyme assays described in the Examples, below.

Separation of the resulting fagopyritol, insulin mediator, insulin mediator analogue, or insulin mediator homologue from any other components may be achieved by methods known to one of ordinary skill in the art, such as with carbon-Celite, BioRad P2 gel, TLC, HPLC, or Dowex columns.

Thus, the method of the present invention can be used to produce an isolated or substantially pure fagopyritol, insulin mediator, insulin mediator analogue, insulin mediator homologue, insulin mediator inhibitor, or salts or derivatives thereof. As used herein, an isolated fagopyritol, insulin mediator, insulin mediator analogue, insulin mediator homologue, or insulin mediator inhibitor, is one which is substantially free of other components with which it naturally occurs. As referred to herein, substantially pure means substantially free of other compounds or materials, such as galactinol, myo-inositol, digalactosyl myo-inositol, phytin, aromatic materials (e.g. polyphenols and pigments and other colored aromatic materials), cell wall particles, proteins, and acids (e.g. organic acids, nucleic acids, and amino acids) and their salts. Typically, substantially pure fagopyritols, insulin mediators, insulin mediator analogues, insulin mediator homologues, or insulin mediator inhibitors are those having greater than about 95% purity, such as greater than about 98% purity or from about 95% to about 99% purity.

Salts of the fagopyritols can be the reaction product of a base having a pKa (i.e., –log Ka) greater than the pKa of one or more of the fagopyritols' hydroxyl groups, such as a metal hydroxide or alkoxide, an amonium hydroxide, or an amine (e.g. a tertiary amine, like triethyl amine). Exemplary salts are alkali metal salts, such as lithium salts, sodium salts, and potassium salts, alkali earth metal salts, such as calcium salts and barium salts, ammonium salts, sufonium salts, and phosphonium salts.

Derivatives of the fagopyritols, include, for example, the reaction products of the fagopyritols with compounds bearing a carbon having a positive charge, such as an alkyl halide, in which case the derivative is an ether of the fagopyritol, or a carboxylic acid halide (e.g., acetyl chloride) or anhydride (e.g., acetic anhydride), in which case the derivative is an ester of the fagopyritol (e.g., the acetate).

The fagopyritols, insulin mediators, insulin mediator analogues, insulin mediator homologues, and insulin mediator inhibitors produced with the fagopyritol synthase genes of the present invention can be used in a composition which includes one or more of fagopyritol A1, fagopyritol A2, fagopyritol A3, fagopyritol B1, fagopyritol B2, fagopyritol B3, D-chiro-inositol, an insulin mediator, an insulin mediator analogue, an insulin mediator homologue, or an insulin mediator inhibitor. Preferably, the composition is substantially free of one or more of galactinol, myo-inositol, digalactosyl myo-inositol, phytin, aromatic materials (e.g. polyphenols and pigments and other colored aromatic materials), cell wall particles, proteins, and acids (e.g. organic acids, nucleic acids, and amino acids) and their salts. It was observed that a mixture of fagopyritols was degraded within six hours in the presence of human fecal bacteria under in vitro conditions in the laboratory. Therefore, it is believed that the fagopyritols are digested by bacteria in the digestive tract to release free D-chiro-inositol for uptake, or in the case of monomers or dimers, may be taken up by cells of the digestive tract.

The aforementioned fagopyritols, insulin mediators, insulin mediator analogues, insulin mediator homologues, insulin mediator inhibitors, and compositions are useful in treating diabetes in patients, such as mammals, including dogs, cats, rats, mice, and humans, by administering an effective amount of isolated or substantially pure fagopyritols, insulin mediators, insulin mediator analogues, insulin mediator homologues, insulin mediator inhibitors, or compositions to such patients. The aforementioned fagopyritols, insulin mediators, insulin mediator analogues, insulin mediator homologues, insulin mediator inhibitors, and compositions may also be useful in treating polycystic ovary syndrome (see Nestler et al., *New England J. of Med.*, 340:1314-1320 (1999), which is hereby incorporated by reference in its entirety). For example, the substantially pure fagopyritols, insulin mediators, insulin mediator analogues, insulin mediator homologues, and insulin mediator inhibitors, the compositions, or one or more isolated fagopyritols, insulin mediators, insulin mediator analogues, insulin mediator homologues, and insulin mediator inhibitors can be administered alone, or in combination with suitable pharmaceutical carriers or diluents. The diluent or carrier ingredients should be selected so that they do not diminish the therapeutic effects of the fagopyritols, insulin mediators, insulin mediator analogues, insulin mediator homologues, insulin mediator inhibitors, or compositions. Suitable pharmaceutical compositions include those which include a pharmaceutical carrier and, for example, one or more of an isolated fagopyritol A1, an isolated fagopyritol A2, an isolated fagopyritol A3, an isolated fagopyritol B1, an isolated fagopyritol B2, an isolated fagopyritol B3, an insulin mediator, an insulin mediator analogue, an insulin mediator homologue, or an insulin mediator inhibitor.

The fagopyritols, insulin mediators, insulin mediator analogues, insulin mediator homologues, insulin mediator inhibitors, and compositions herein can be made up in any suitable form appropriate for the desired use; e.g., oral, parenteral, or topical administration. Examples of parenteral administration are intraventricular, intracerebral, intramuscular, intravenous, intraperitoneal, rectal, and subcutaneous administration. The preferred route for administration is oral. In cases where the fagopyritols, insulin mediators, insulin mediator analogues, insulin mediator homologues, or insulin mediator inhibitors, are administered topically or parenterally, it is preferred that they be pre-hydrolyzed.

Suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents, such as starch and alginic acid; binding agents, such as starch, gelatin, and acacia; and lubricating agents, such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, such as methyl cellulose, tragacanth, sodium alginate; wetting agents, such as lecithin and polyoxyethylene stearate; and preservatives, such as ethyl-p-hydroxybenzoate. Dosage forms suitable for parenteral administration include solutions, suspensions, dispersions, emulsions, and the like. They may also be manufactured in the form of sterile solid compositions which can be dissolved or suspended in sterile injectable medium immediately before use. They may contain suspending or dispersing agents known in the art.

For oral administration either solid or fluid unit dosage forms can be prepared. For preparing solid compositions, such as tablets, a suitable fagopyritol, insulin mediator, insulin mediator analogue, insulin mediator homologue, insulin mediator inhibitor, or composition, as disclosed above, is mixed with conventional ingredients, such as talc, magnesium stearate, dicalcium phosphate, magnesium aluminum silicate, calcium sulfate, starch, lactose, acacia methylcellulose, and functionally similar materials as pharmaceutical diluents or carriers. Capsules are prepared by mixing the disclosed fagopyritols, insulin mediators, insulin mediator analogues, insulin mediator homologues, insulin mediator inhibitors, or compositions with an inert pharmaceutical diluent and filling the fixture into a hard gelatin capsule of appropriate size. Soft gelatin capsules are prepared by machine encapsulation of a slurry of the fagopyritol, insulin mediator, insulin mediator analogue, insulin mediator homologue, insulin mediator inhibitor, or composition with an acceptable vegetable oil, light liquid petrolatum, or other inert oil.

Fluid unit dosage forms for oral administration such as syrups, elixirs, and suspensions can be prepared. The water-soluble forms can be dissolved in an aqueous vehicle together with sugar, aromatic flavoring agents, and preservatives to form a syrup. An elixir is prepared by using a hydro-alcoholic (ethanol) vehicle with suitable sweeteners, such as sugar and saccharin, together with an aromatic flavoring agent. Suspensions can be prepared with a syrup vehicle with the aid of a suspending agent, such as acacia, tragacanth, methylcellulose, and the like.

When the fagopyritols, insulin mediators, insulin mediator analogues, insulin mediator homologues, insulin mediator inhibitors, or compositions are administered orally, suitable daily dosages can be based on suitable doses of free D-chiro-inositol, such as those described in U.S. Pat. No. 5,124,360 to Larner et al., which is hereby incorporated by reference in its entirety. It is believed that about half of the fagopyritols as extracted is D-chiro-inositol, mostly as bound D-chiro-inositol with small amounts of free D-chiro-inositol. Therefore, suitable doses of fagopyritol are about twice the suitable doses of D-chiro-inositol. Typically, for oral administration, suitable daily doses are from about 5 mg to about 200 mg of the fagopyritol or composition per kilogram of the subject's body weight.

Alternatively, the fagopyritols, insulin mediators, insulin mediator analogues, insulin mediator homologues, or insulin mediator inhibitors, can be administered orally in foodstuffs. For example, fagopyritols can be incorporated in purified form or in the form of buckwheat bran in bread, bread rolls, or other foodstuffs to form an edible product for consumption of fagopyritols. Fortification of breads, bread rolls, and other foodstuffs with synthesized fagopyritols, insulin mediators, insulin mediator analogues, insulin mediator homologues, or insulin mediator inhibitors can provide a way to incorporate larger quantities of fagopyritols, insulin mediators, insulin mediator analogues, insulin mediator homologues, or insulin mediator inhibitors into a daily diet. Suitable procedures for bread preparation can be found, for example, in Brown, *The Tassajara Bread Book*, Boston: Shambhala Publications (1986), which is hereby incorporated by reference.

For parenteral administration, fluid unit dosage forms are prepared utilizing the aforementioned fagopyritols, insulin mediators, insulin mediator analogues, insulin mediator homologues, insulin mediator inhibitors, or compositions and a sterile vehicle, water being preferred. The fagopyritol, insulin mediator, insulin mediator analogue, insulin mediator homologue, insulin mediator inhibitor, or composition, depending on the vehicle and concentration used, can be either suspended or dissolved in the vehicle. In preparing solutions, the fagopyritol, insulin mediator, insulin mediator analogue, insulin mediator homologue, insulin mediator inhibitor, or composition can be dissolved in water for injection and filter sterilized before filling into a suitable vial or ampule and sealing. Advantageously, adjuvants, such as a local anesthetic, preservative, and buffering agents, can be dissolved in the vehicle. To enhance the stability, the fluid unit dosage form can be frozen after filling into the vial, and the water removed under vacuum. The dry lyophilized powder is then sealed in the vial, and an accompanying vial of water for injection is supplied to reconstitute the liquid prior to use. Parenteral suspensions are prepared in substantially the same manner except that the fagopyritol, insulin mediator, insulin mediator analogue, insulin mediator homologue, insulin mediator inhibitor, or composition is suspended in the vehicle instead of being dissolved, and sterilization cannot be accomplished by filtration. The fagopyritol, insulin mediator, insulin mediator analogue, insulin mediator homologue, insulin mediator inhibitor, or composition can be sterilized by exposure to ethylene oxide before suspending in the sterile vehicle. Advantageously, a surfactant or wetting agent is included in the parenteral suspension to facilitate uniform distribution of the fagopyritol, insulin mediator, insulin mediator analogue, insulin mediator homologue, insulin mediator inhibitor, or composition. Parenteral dosages can range from about 5 mg to about 200 mg of fagopyritol, insulin mediator, insulin mediator analogue, insulin mediator homologue, insulin mediator inhibitor, or composition per kilogram of the subject's body weight per day. Preferably, the daily parenteral dosage would be considerably less than the dose per kilogram of subject body weight, considering that, in oral administration, the galactose from the fagopyritols would be consumed by microbes in the digestive tract whereas, in parenteral administration the galactose would contribute to blood sugar levels.

Alternatively, the fagopyritol, insulin mediator, insulin mediator analogue, insulin mediator homologue, insulin mediator inhibitor, or composition can be incorporated into a sustained release formulation and surgically implanted using conventional methods. Suitable sustained release matrices include those made of ethylene vinyl acetate and other biocompatible polymers.

For topical administration, carriers, such as phospholipid vesicles, which contain the aforementioned fagopyritols, insulin mediators, insulin mediator analogues, insulin mediator homologues, or insulin mediator inhibitors, may facilitate uptake through the skin.

As indicated above, it is believed that the fagopyritols are digested in the digestive tract by bacteria to release free D-chiro-inositol for uptake. It is known that D-chiro-inositol is an anti-oxidant and, more particularly, a hydroxyl radical scavenger. Accordingly, the fagopyritol and compositions can also be used as a source of the antioxidant D-chiro-inositol, for example, by administering, preferably orally, the subject fagopyritols and compositions to a subject.

The present invention is further illustrated by the following examples.

EXAMPLES

Example 1

Fagopyritol Synthase, A Novel Multi-Functional Galactinol Synthase Homologue, Catalyzes the Biosynthesis of Fagopyritol A1 and Fagopyritol B1 in Buckwheat Seeds Nucleotide and Amino Acid Sequence Analyses The nucleotide sequences of galactinol synthase genes identified to date and their corresponding amino acid sequences were obtained from the nucleotide and protein databases (http://www.ncbi.nlm.nih.gov). Nucleotide and amino acid sequences were compared using a multiple sequence alignment program, CLUSTAL W (http://workbench.sdsc.edu). The identities of buckwheat cDNA fragments amplified from RT-PCR and RACE-PCR assays were examined by BLASTN and BLASTX programs (http://www.ncbi.nlm.nih.gov and http://workbench.sdsc.edu).

Isolation of FeGolS cDNA

The synthesis of PCR-directed cDNA from the poly(A)+ RNA isolated from developing buckwheat seeds (harvested at 20 to 25 days after pollination) was described previously (Lewis et al., Gene 246:81-91 (2000), which is hereby incorporated by reference in its entirety). Briefly, it involved the synthesis of the first strand cDNA using an oligo-dT primer (primer A, 5'-GCGGCCGCTTTTTTTTTTTTTTTT-3' (SEQ ID NO:16), FIG. 5) and reverse transcriptase, followed by oligo-dG-homopolymer-tailing of the first-strand cDNA with terminal transferase. Buckwheat FeGolS cDNAs were isolated by 5' and 3' RACE-PCR assays which were typically performed in either 25 or 50 µl reaction volume containing 100 pmol primers, 200 µM dNTPs, diluted G-tailed first strand cDNA (2 to 20 ng), 2 mM MgCl$_2$ in 1×PCR reaction buffer (50 mM Tris/HCl, 10 mM KCl, 5 mM (NH$_4$)$_2$SO$_4$, pH 8.3) with 1 to 2 units of FastStart Taq DNA Polymerase (Roche Applied Science, Indianapolis, Ind.). In the PCR assays, after the initial 4 minute denaturation step at 94° C., 38 to 40 cycles of amplification were carried out with each cycle consisting of the three consecutive incubations at 94° C. for 45 seconds, at 50 to 58° C. for 45 seconds, and at 72° C. for 45 seconds. Finally, the assays were terminated after a 10 minute final extension cycle at 72° C. All PCR products were cloned into pCRII-TOPO vector (Invitrogen, Carlsbad, Calif.) and propagated in *Escherichia coli*. For the isolation of cDNAs corresponding to buckwheat GolS genes, the initial amplification was carried out using the G-tailed cDNA preparation in combination with GS1 primer (5'-GGGCCACTGAACCTTATGGGGGCACTGCTGGC-3') (SEQ ID NO:17) representing an internal protein coding sequence highly conserved in most GolS genes, and primer B (5'-AAGGAATTCCCCCCCCCCCCCC-3') (SEQ ID NO:18) partially complementary to the G-tailed 5'-end of the first strand cDNAs (FIG. 5). One of the amplified cDNA fragments, 469 bp in length, was shown to represent a GolS homolog in buckwheat when its nucleotide sequence was analyzed by BLASTN and BLASTX programs. The gene represented by this partial cDNA clone was designated as FeGolS-1 for *Fagopyrum esculentum* GolS-1. The overlapping cDNA fragments containing the 5'-end region of FeGolS-1 cDNA were further amplified in 5' RACE-PCR assays using an upstream internal primer, GS2 (5'-GCTCCATGATGGCTCACAGAAACAGTCC-3') (SEQ ID NO:19) and primer B (FIG. 5). This PCR amplification yielded a cDNA fragment of 548 bp in length which contained the complete 5'-end of the protein coding sequence and 82 bp long 5' untranslated region (5'UTR). An overlapping cDNA fragment of about 900 bp in length containing the complete 3'-end region of FeGolS-1 was also obtained in 3' RACE-PCR assays, using an internal primer, GS3 (5'-GCTCACGCATACTATGTCATCAACTACTCC-3') (SEQ ID NO:20) and primer A (FIG. 5). In addition, two additional cDNA fragments of about 960 bp in length exhibiting nucleotide sequences that were nearly identical to each other but clearly distinct from the 3'-end region of FeGolS-1 cDNA were obtained. Analyses of their nucleotide sequences by BLASTN and BLASTX programs also identified them as GolS homologues. Thus, the genes corresponding to these two additional cDNAs were designated as FeGolS-2 and FeGolS-3. In an attempt to amplify the 5'-end regions of the FeGolS-2 and FeGolS-3 cDNAs, 5' RACE-PCR assays were performed using primer A and an internal primer, GS4 (5'-GAACTTCTTGCCCTCGACCATCTTAGGCTGAG-3') (SEQ ID NO:21) representing the nucleotide sequence that was common to FeGolS-2 and FeGolS-3 cDNA's but not shared by FeGolS-1 cDNA (FIG. 5). An overlapping cDNA fragment of 984 bp in length was obtained from the assays (FIG. 5). The nucleotide sequence of the cDNA fragment confirmed that it was a part of FeGolS-2 cDNA. Finally, an intact FeGolS-1 cDNA containing the complete protein coding sequence as well as 5' and 3' UTRs was reconstituted by joining the 398 bp long 5'-end region of the 5' RACE-PCR clone with the 871 bp long 3'-end region of the 3' RACE-PCR clone at the unique HindIII site (FIG. 5). Similarly, an intact FeGolS-2 cDNA was reconstituted by joining the 700-bp 5'-end region of the 5' RACE-PCR clone with the 650-bp long 3'-end region of the 3' RACE-PCR clone at the unique XhoI site (FIG. 5).

DNA Sequencing

All PCR-generated cDNA clones were sequenced at the DNA Sequencing Facility, BioResource Center, Cornell University (http://brcweb.biotech.cornell.edu).

Bacterial Expression and Purification of Recombinant GolS Proteins

The entire 1002 bp long protein coding sequence of FeGolS-1 cDNA was amplified from the reconstituted FeGolS-1 cDNA using two oligonucleotide primers, FG1-5 (5'-GTTCCAACCATATGGCACCAGAACTC-3') (SEQ ID NO:22) and FG1-3 (5'-GGATCCGATACTTAAGCTGCG-GAAGGAGC-3') (SEQ ID NO:23) (FIG. 5). FG1-5 and FG1-3 primers contained the restriction enzyme recognition sites for NdeI and BamHI, respectively, to allow easy cloning of the amplified coding sequence into a bacterial expression vector, pET-14b (Novagen, Madison, Wis.), in frame with the preceding poly-histidine codons in the vector. After initial cloning into pCRIITOPO vector and amplification of the plasmid in $E.\ coli$, the protein coding sequence was excised from the plasmid by digestion with NdeI and BamHI, and cloned into pET-14b vector at the corresponding cloning sites. Similarly, the 1065 bp long entire protein coding sequence from the reconstituted FeGolS-2 cDNA was inserted into pET14b vector after amplifying it with FG2-5 (5'-CATATGACTTCCGAGATGGCGCCACAG-3') (SEQ ID NO:24) and FG2-3 (5'-GGATCCTCAGGCAGCA-GACGGGGCGTGTACG-3') (SEQ ID NO:25) primers which also contained NdeI and BamHI sites, respectively (FIG. 5). In addition, the 987 bp long entire coding sequence was isolated from a soybean EST clone (GenBank accession no. BE330777) presumed to encode soybean galactinol synthase (GmGolS) in leaf tissues (INCYTE GENOMICS, cat. no. Gm-c1041), and it was cloned into pET14-b vector. Since only partial cDNA sequence data were available in GenBank, the whole cDNA insert was re-sequenced (GenBank Accession No. AY126715). Two primers, GG-5 (5'-CATCACT-GAGCATATGGCTGG-3') (SEQ ID NO:26) and GG-3 (5'-GGATCCAAAGACACTCTTAAGCAGCAGATGGGG-3') (SEQ ID NO:27), containing NdeI and BamHI restriction enzyme recognition sites, respectively, were used for the amplification of the protein coding sequence. After cloning into pCRIITOPO vector and amplification in $E.\ coli$, the NdeI/BamHI fragment containing the entire protein coding sequence was isolated and cloned into pET-14b vector. The pET14b plasmids containing the buckwheat and soybean GolS cDNAs were mobilized into $E.\ coli$ strain BL21 (DE3) (Novagen, Madison, Wis.). Expression of the recombinant GolS proteins in $E.\ coli$ were induced with 1 mM isopropyl β-D-thiogalactoside (IPTG) according to the manufacture's recommended protocol (Novagen, Madison, Wis.). The bacterial cells were collected by centrifugation, and resuspended in 10 mM Tris-HCl buffer (pH 8.0). The soluble protein fraction was extracted from the bacterial cells by the gentle disruption of their cell walls with BugBuster Protein Extraction Reagent (Novagen, Madison, Wis.) containing Benzonase (Novagen, Madison, Wis.). In some experiments, the soluble protein fraction was extracted from bacterial cells through disruption of bacterial cells by sonic oscillation (at 50% level, twice for 10 seconds each, at 4° C.) with a sonicator (Fisher Scientific Sonic Dismembrator Model 500). Poly-histidine tagged recombinant proteins were purified from the extracts using His.Bind Quick 300 Cartridges (Novagen, Madison, Wis.) according to the manufacture's recommended protocol. Purified recombinant proteins were dialyzed against 50 mM Hepes buffer, pH 7.0, containing 5 mM $MnCl_2$, immediately after elution from the His.Bind Quick 300 Cartridges and before enzyme assay. Aliquots (0.25 to 0.5 μg) of samples of the purified proteins were checked by SDS-PAGE using a 12% resolving gel and a 5% stacking gel. Protein samples (10 μg each) extracted from uninduced and induced bacterial cells prior to protein purification were also included in the SDS-PAGE analysis. Proteins in the gels were visualized by staining with Coomassie Brilliant Blue R250 solution (25 g/liter in methanol:acetic acid:water, 45:10:45, v/v/v) and destained in methanol:acetic acid:water (30:10:60, v/v/v).

Enzyme Assays

Both the crude soluble protein extracts from $E.\ coli$ and the purified GolS recombinant proteins were used in enzyme assays. Fagopyritol synthase assays included 20 mM UDP-Gal as the galactosyl donor, 20 mM D-chiro-inositol as the galactosyl acceptor, 50 mM Hepes buffer, pH 7.0, 2 mM dithiothreitol, 5 mM $MnCl_2$, and 1 to 5 μg of crude protein extract or purified enzyme protein (estimated by the Bio-Rad Protein Assay, BIO-RAD) in 50 μL total volume. In galactinol synthase assays, UDP-Gal was substituted with 20 mM galactinol as the galactosyl donor. Assays were run at 30° C. for 30 to 300 minutes. Reactions were stopped by addition of 50 μL of 100% ethanol. After addition of 25 μg of phenyl α-D-glucoside as internal standard, the reaction mixture was heated at 80° C. for 30 minutes, passed through a 10,000 MW cutoff filter (NANOSEP™ Microconcentrators, Pall Filtron Co.), and evaporated to dryness under a stream of nitrogen gas. Residues were stored overnight in a desiccator with phosphorus pentoxide to remove traces of water, derivatized with trimethylsilylimidazole:pyridine (1:1, v/v) at 80° C. for 45 minutes, and analyzed for fagopyritols or other soluble carbohydrate products by high resolution gas chromatography on a HP1-MS (Agilent Technologies) capillary column (15 m length, 0.25 mm i.d., 0.25 μm film thickness) as previously described (Horbowicz et al., *Seed Sci. Res.* 4:385-405 (1994); Horbowicz et al., *Planta* 205:1-11 (1994), which are hereby incorporated by reference in their entirety).

Results

Cloning of cDNAs Encoding Two Distinct Types of GolS Enzymes in Buckwheat Seeds

Initially, several GolS gene sequences reported from various plant species, either derived from genomic or cDNA clones, were compiled and compared to identify stretches of highly conserved nucleotide sequences corresponding to the conserved amino acid domains of GolS enzymes. By using oligonucleotide primers representing these conserved nucleotide sequences and the first-strand cDNA synthesized from polyA$^+$ RNA extracted from developing seeds in our PCR assays, a total of three different GolS cDNAs from buckwheat were isolated (FIG. 5). The genes corresponding to these three buckwheat cDNA clones were designated as FeGolS-1, -2, and -3 for *Fagopyrum esculentum* GolS-1, -2, and -3.

FeGolS-1 cDNA was initially obtained as a partial clone of 469 bp in length, using an internal GolS gene-specific primer (GS1) and primer B corresponding to the dG homopolymer tail present at the 5' end of the cDNA (FIG. 5). Subsequently, the missing 5'-end region of FeGolS-1 cDNA was obtained by 5' RACE-PCR using the second internal primer (GS2) and primer B (FIG. 5). One of the 5' RACE-PCR clones contained a complete 5'-end of the protein coding region together with 82 bp long 5' untranslated region (5'UTR) (FIG. 5). The missing 3'-end region of FeGolS-1 cDNA was obtained by 3' RACE-PCR using an internal primer (GS3) and primer A complementary to the polyA tail present in all cDNAs (FIG. 5). In the 3' RACE-PCR assays, two additional clones (Fe- GolS-2 and FeGolS-3) were obtained. They were longer (987 bp and 986 bp for FeGolS-2 and FeGolS-3, respectively) than the FeGolS-1 cDNA clone (901 bp) and exhibited restriction patterns clearly distinct from that of FeGolS-1. No obvious polyadenylation signals were found upstream of the polyadenylation sites in any of the three genes. The 5'-end region of FeGolS-2 cDNA containing the complete 5'-end of the protein coding region was obtained by 5' RACE-PCR using a gene-specific primer, GS4 and primer B (FIG. 5). Cloning of cDNA fragments containing the 5'-end of the FeGolS-3 gene was not successful.

Intact FeGolS-1 and FeGolS-2 cDNAs containing the complete protein coding sequences with 5' and 3' UTRs were reconstituted by joining the overlapping 5' and 3' RACE-PCR clones for each gene (FIG. 5). The reconstituted FeGolS-1 cDNA is 1269 bp long containing a single open reading frame (ORF) (GenBank accession no. AY126718). On the other hand, the reconstituted FeGolS-2 cDNA is 1326 bp long; it also contains a single ORF (GenBank Accession No. AY126716). The partial FeGolS-3 cDNA clone is 986 bp long and contains the complete 3'-end of the cDNA (GenBank accession no. AY126717). According to the nucleotide sequence comparison, FeGolS-1 is distinct from FeGolS-2 sharing only 62.2% sequence identity. On the other hand, FeGolS-2 and FeGolS-3 share a nearly identical nucleotide sequence in their 3' regions. Whereas the FeGolS-2 cDNA clone differs from FeGolS-3 only by 15 nucleotides within the 986/987 bp long 3' region, FeGolS-2 differs from FeGolS-1 by 385 nucleotides at the corresponding 3' region. These results suggest that FeGolS-1 and FeGolS-2 represent two different members of a GolS gene family in buckwheat. The complete 1406 bp nucleotide sequence of the soybean galactinol synthase (GmGolS) cDNA (assigned GenBank Accession No. AY126715) had a high degree of sequence similarity to FeGolS-1.

Primary Structures of GolS Polypeptides Deduced From cDNA Sequences

The amino acid sequence deduced from the reconstituted FeGolS-1 cDNA indicated that it is capable of encoding a polypeptide of 333 amino acid residues with a predicted molecular mass of 38.3 kDa (FIG. 1). On the other hand, FeGolS-2 cDNA is capable of encoding a polypeptide of 354 amino acids with a predicted molecular mass of 40.7 kDa (FIG. 2). Predicted FeGolS-2 and -3 differ from each other only by three amino acid residues in the carboxyl half of the polypeptide whereas each differs from FeGolS-1 by 96 amino acid residues in the corresponding region. The presence of a longer stretch (additional 17 residues) of amino acid sequence was identified near the carboxyl termini in FeGolS-2 (and also in FeGolS-3), mainly accounting for its larger predicted molecular mass than that for FeGolS-1 (FIG. 6). The amino acid sequence deduced from the 987 bp long coding sequence of the soybean GmGolS cDNA indicated that it is capable of encoding a polypeptide of 328 amino acid residues with a predicted molecular mass of 38.0 kDa (FIG. 4).

Both FeGolS-1 and FeGolS-2 polypeptides share a high degree of amino acid sequence similarity with other GolSs identified from a wide variety of plant species (FIG. 7). The highly conserved serine phosphorylation site and the carboxyl terminal pentapeptide, APSAA (SEQ ID NO:28) (Sprenger et al., *Plant J.* 21:249-258 (2000), which is hereby incorporated by reference in its entirety) are also present in all three FeGolS proteins. In addition, a putative manganese binding motif, DXD, believed to be conserved in most galactosyl transferases (Breton et al., *J. Biochem.* 123:1000-1009 (1998); Busch et al., *J. Biol. Chem.* 273:19566-19572 (1998); Wiggins et al., *Proc. Natl. Acad. Sci. USA* 95:7945-7950 (1998), which are hereby incorporated by reference in their entirety) is also present in all GolSs examined, including the three FeGolSs. A phylogenetic analysis indicated that both FeGolS-1 and FeGolS-2 are evolutionarily most closely related to a *Brassica napus* GolS.

Recombinant Protein Expression and Purification

Figure 8:
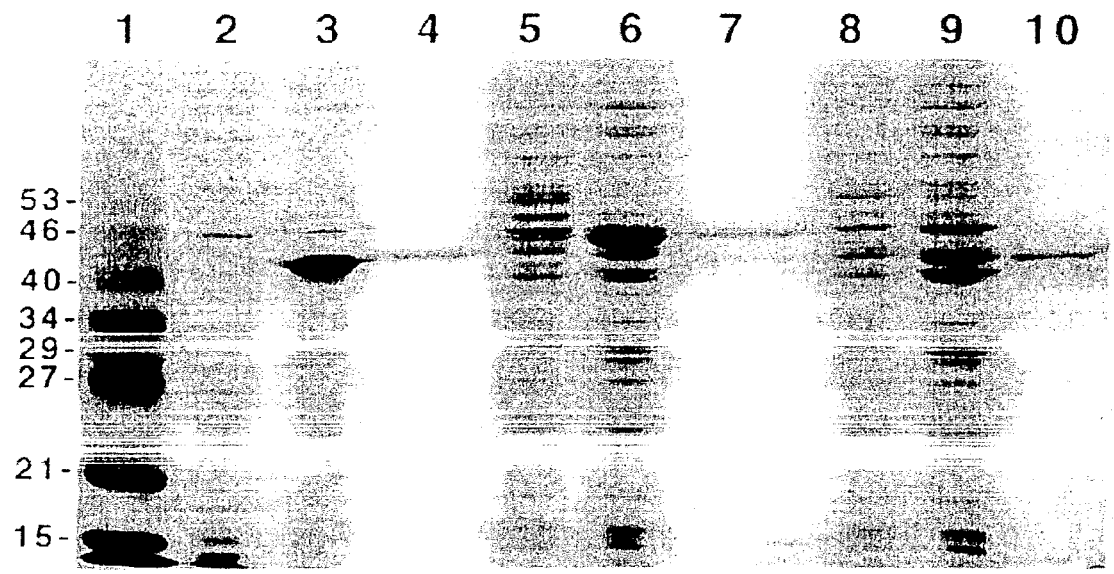
FIG. 8 shows the bacterial expression and purification of recombinant GolS proteins. The recombinant GolS proteins expressed in *E. coli* and subsequently purified proteins were examined by SDS-PAGE: lane 1, protein molecular weight marker (kDa of bands indicated in the left margin); lanes 2 and 3, 10 µg each of the total soluble protein extracts from uninduced and induced bacteria cells harboring FeGolS-1 cDNA, respectively; lane 4, 0.25 µg of the purified recombinant FeGolS-1 protein; lanes 5 and 6, 10 µg each of the total soluble protein extracts from uninduced and induced bacteria cells harboring FeGolS-2 cDNA, respectively; lane 7, 0.25 µg of the purified recombinant FeGolS-2 protein; lanes 8 and 9, 10 µg each of the total soluble protein extracts from uninduced and induced bacteria cells harboring GmGolS cDNA, respectively; lane 10, 0.25 µg of the purified recombinant GmGolS protein.

FIG. 8 shows an SDS-PAGE gel used to monitor the protein expression and purification steps. Total soluble protein extracts from uninduced and induced bacteria cells harboring FeGolS-1 cDNA are shown in lanes 2 and 3, respectively. The purified recombinant FeGolS-1 protein fraction (lane 4) contained a single prominent polypeptide with an apparent molecular mass of 43 kDa. Total soluble protein extracts from uninduced and induced bacteria cells harboring FeGolS-2 cDNA are shown in lanes 5 and 6, respectively. The purified recombinant FeGolS-2 protein fraction (lane 7) contained a single prominent polypeptide with an apparent molecular mass of 45.5 kDa. Total soluble protein extracts from uninduced and induced bacteria cells harboring GmGolS cDNA are shown in lanes 8 and 9, respectively. A single polypeptide of with an apparent molecular mass of 43 kDa was found in the purified recombinant GmGolS protein fraction (lane 10). No polypeptide with its molecular mass corresponding to any of the recombinant GolS proteins described above was found after purification of histidine-tagged protein from the total soluble protein extract from control bacteria which had been transformed with the pET-14b vector alone. These results indicated that the purified recombinant FeGolS-1, FeGolS-2, and GmGolS proteins were derived from the expression of their corresponding genes.

Substrate Specificity of FeGolS-1 and FeGolS-2

Figure 9:
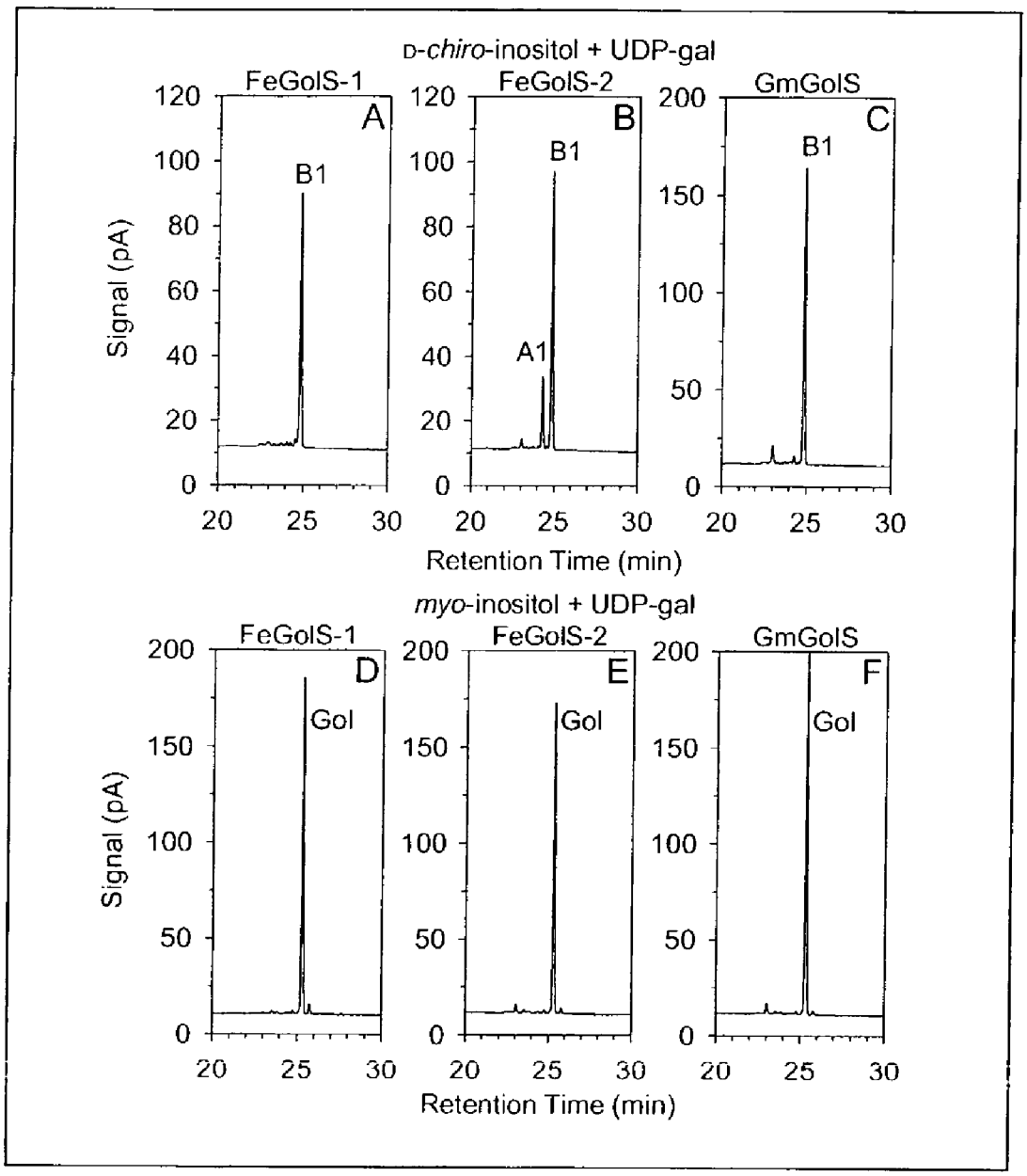
FIGS. 9A-F show product accumulation with purified recombinant protein.

Both purified recombinant FeGolS-1 and FeGolS-2 proteins exhibited fagopyritol synthase activities. FeGolS-1 catalyzed the biosynthesis of fagopyritol B1 with UDP-Gal as the galactosyl donor and D-chiro-inositol as the galactosyl receptor (FIG. 9A). However, only FeGolS-2 catalyzed the biosynthesis of both fagopyritol A1 and fagopyritol B1 in a ratio of 1:4 demonstrating the unique product specificity of FeGolS-2 (FIG. 9B). Both FeGolS-1 and FeGolS-2 catalyzed the biosynthesis of galactinol with UDP-Gal as galactosyl donor and myo-inositol as galactosyl receptor (FIGS. 9D and 9E), consistent with the structural homology of these enzymes to galactinol synthase. No products were biosynthesized using protein extracts from control bacteria transformed with the vector only, confirming that FeGolS-1 and FeGolS-2 catalyzed the biosynthesis of fagopyritols and galactinol. Neither FeGolS-1 nor FeGolS-2 was active with galactinol as the galactosyl donor, demonstrating that both enzymes had substrate specificity for UDP-Gal. Neither FeGolS-1 nor FeGolS-2 biosynthesized fagopyritol A1 from fagopyritol B1 (as both donor and receptor) indicating that FeGolS-2 catalyzes the biosynthesis of fagopyritol A1 directly by transfer of the galactosyl residue from UDP-Gal. As a control, soybean galactinol synthase (GmGolS) catalyzed the biosynthesis of galactinol with UDP-Gal and myo-inositol as substrates (FIG. 9F), but also catalyzed the biosynthesis of fagopyritol B1, but not fagopyritol A1, with UDP-Gal and D-chiro-inositol as substrates (FIG. 9C). Activity of FeGolS-1 was similar to that for GmGolS, whereas FeGolS-2, by catalyzing the biosynthesis of fagopyritol A1, was uniquely different from the soybean enzyme.

Discussion

The FeGolS-1 gene encodes an enzyme that catalyzes fagopyritol B1 biosynthesis using UDP-Gal as galactosyl donor and D-chiro-inositol as galactosyl acceptor. The FeGolS-2 gene, a unique member of the buckwheat galactinol synthase gene family, encodes a fagopyritol synthase that catalyzes the biosynthesis of both fagopyritol A1 and fagopyritol B1 using UDP-Gal as galactosyl donor and D-chiro-inositol as galactosyl acceptor. Based on the molecular structure and absolute configuration of fagopyritol A1 and fagopyritol B1 determined by NMR (Obendorf et al., *Carbohydr. Res.* 328:623-627 (2000), which is hereby incorporated by reference in its entirety), FeGolS-2 catalyzes the formation of the α-(1→3)-linkage unique to fagopyritol A1 and other members of the fagopyritol A series found only in buckwheat, as well as the α-(1→2)-linkage of fagopyritol B1 and other members of the fagopyritol B series (Obendorf et al., *Carbohydr. Res.* 328:623627 (2000); Steadman et al., *Carbohydr. Res.* 331:19-25 (2001), which are hereby incorporated by reference in their entirety). FeGolS-1, FeGolS-2, and GmGolS all biosynthesize galactinol using UDP-Gal as galactosyl donor and myo-inositol as galactosyl acceptor. However, buckwheat FeGolS-1 and soybean GmGolS do not form fagopyritol A1. Thus, the novel buckwheat FeGolS-2 gene and its protein product are distinctly different in both structure and function from the buckwheat FeGolS-1 gene and the soybean GmGolS gene and their corresponding proteins. The longer amino acid sequence (13 to 23 amino acids) near the carboxyl end of buckwheat FeGolS-2 (and also FeGolS-3) is unique among known GolS sequences from various species and may be related to the property of FeGolS-2 to form the unique α-(1→3)-linkage.

Retention of fagopyritol synthase activity by purified recombinant FeGolS-1, FeGolS-2, and GmGolS protein required $Mn^{+2}$ (5 mM optimal) as a cofactor, as it has been reported with galactinol synthase from other sources (Saravitz et al., *Plant Physiol.* 83:185-189 (1987); Castillo et al., *J. Agric. Food Chem.* 38:351-355 (1990); Smith et al., *Plant Physiol.* 96:693698 (1991); Liu et al., *Plant Physiol.* 109:505-511 (1995); Kuo et al., *Plant Sci.* 125:1-11 (1997), which are hereby incorporated by reference in their entirety). One to 10 mM $Mn^{+2}$ was most commonly used for the retention of galactinol synthase activity. Interestingly, the antihyperglycemic effects of D-chiro-inositol were associated with manganese (Fonteles et al., *Hormone Metab. Res.* 32:129 132 (2000), which is hereby incorporated by reference in its entirety) in subjects with non-insulin dependent diabetes melitus. Buckwheat seeds are a rich source of manganese (Steadman et al., *J. Sci. Food Agric.* 81:1094-1100 (2001), which is hereby incorporated by reference in its entirety), and buckwheat has been used for the treatment of diabetes (Lu et al., in *Proceedings of the 5th International Symposium on Buckwheat*, eds. Lin et al., Agriculture Publishing House, Beijing, pp 458-464 (1992); Wang et al., in *Proceedings of the 5th International Symposium on Buckwheat*, eds. Lin et al., Agriculture Publishing House, Beijing, pp 465-467 (1992), which are hereby incorporated by reference in their entirety).

Pea (*Pisum sativum* L.) seed galactinol synthase (Frydman et al., *Biochem. Biophys. Res. Comm.* 12:121-125 (1963), which is hereby incorporated by reference in its entirety) and lentil (*Lens culinaris* Medik.) stachyose synthase (Hoch et al., *Arch. Biochem. Biophys.* 366:75-81 (1999), which is hereby incorporated by reference in its entirety) have been reported to form a product with D-chiro-inositol as substrate, but the product was not confirmed to be a fagopyritol. The lack of activity of Adzuki bean (*Vigna angularis* Ohwi and Ohashi) stachyose synthase with D-chiro-inositol (Peterbauer et al., *Plant Physiol.* 117:165-172 (1998), which is hereby incorporated by reference in its entirety) and the very limited accumulation of stachyose in buckwheat seeds (Horbowicz et al., *Planta* 205:1-11 (1998), which is hereby incorporated by reference in its entirety) suggest that stachyose synthase is not involved in the biosynthesis of fagopyritols. The results reported herein clearly demonstrate that FeGolS-2, a galactinol synthase homologue, catalyzes the biosynthesis of both fagopyritol A1 and fagopyritol B1.

Among seven GolS genes identified in *Arabidopsis thaliana*, three were identified as stress responsive (Taji et al., *Plant J.* 29:417-426 (2002), which is hereby incorporated by reference in its entirety). AtGolS-1 and AtGolS-2 were induced by drought and high-salinity stresses but not by cold stress. In contrast, AtGolS-3 was induced by cold stress by not by drought or high-salinity stress. Buckwheat seeds matured at 18° C. accumulated more fagopyritol A1 and fagopyritol B1 than seeds matured at 25° C. (Horbowicz et al., *Planta* 205:1-11 (1998), which is hereby incorporated by reference in its entirety), indicating that FeGolS genes may be cold-responsive.

The nucleotide sequence of the soybean EST clone, BE330777, isolated by a public source (Shoemaker et al., Public soybean EST project; GenBank BE33077; Genome Systems Clone ID: Gm-c1041-80 (5'), Genome Systems, Inc., 4633 World Parkway Circle, St. Louis, Mo. 63134 (1999), which is hereby incorporated by reference in its entirety) with the full sequence first reported herein, demonstrated a very high homology to the soybean seed galactinol synthase gene (I55634), sequence 6 (U.S. Pat. No. 5,648,210 to Kerr et al., which is hereby incorporated by reference in its entirety). The deduced amino acid sequence (328 amino acids) differed by only one amino acid, Ile 223 in GmGolS (AY126715) rather than Met 223 (I55634) (U.S. Pat. No. 5,648,210 to Kerr et al., which is hereby incorporated by reference in its entirety). Of the multiple genes for galactinol synthase, some are specifically expressed in seeds. Modification of galactinol biosynthesis is of commercial interest (U.S. Pat. No. 5,648,210 to Kerr et al.; U.S. Pat. No. 5,710,365 to Kerr, which are hereby incorporated by reference in their entirety) for producing soybean seeds with lower stachyose concentrations for the poultry and pig feed industry (Sebastian et al., in *Soy in Animal Nutrition*, ed. Drackley, Federation of Animal Science Societies, Savoy, Ill., pp 56-73 (2000), which is hereby incorporated by reference in its entirety). A mutant with a single base change in a seed-expressed myo-inositol 1-phosphate synthase (MIPS, EC 5.5.1.4) gene coupled with appropriate modifiers resulted in soybean seeds with both reduced phytic acid and reduced stachyose (Hitz et al., *Plant Physiol.* 128:650-660 (2002), which is hereby incorporated by reference in its entirety) for use in the feed industry.

Fagopyritol A1 is isosteric with 2-amino-2-deoxy-α-D-galactopyranosyl-(1→3)-D-chiro-inositol (Berlin et al., *Tetrahedron Lett.* 31:1109-1112 (1990), which is hereby incorporated by reference in its entirety) related to a putative insulin mediator (Lamer et al., *Biochem. Biophys. Res. Comm.* 151:1416-1426 (1988), which is hereby incorporated by reference in its entirety) deficient in subjects with NIDDM and PCOS. The novel FeGolS-2 gene and FeGolS-2 enzyme described herein may be used to form the unique α-(1→3)-linkage between galactose and D-chiro-inositol.

Example 2

Seed Galactosyl Cyclitols Enhanced by Substrate Feeding

Materials and Methods

Plant Materials

Soybean (*Glycine max* (L.) Merrill) plants were grown in the greenhouse (Obendorf et al., *Crop Sci.* 20:483-486

(1980); Obendorf et al., *Crop Sci.* 38:78-84 (1998), which are hereby incorporated by reference in their entirety) at 27° C. during the day (14 hours) and 22° C. at night (10 hours) under natural sunlight supplemented 14 hours daily with 640 µmol m$^{-2}$ s$^{-1}$ incandescent light from metal halide lamps (Sylvania 1000 watt BU). Three embryos isolated from immature seeds (250±20 mg fresh weight, approximately 35 DPA) by removal of the seed coat and nucellus remnants were incubated in 20 mL screw-capped vials containing 3 mL of substrate (cyclitol and/or sucrose) solutions for 24 hours at 25° C. and 200 µmol m$^{-2}$ s$^{-1}$ fluorescent light. Embryos were blotted, placed in small plastic Petri dishes, and subjected to slow drying at 22° C. by daily transfer to successive lower relative humidity (RH) controlled by saturated salt solutions (Blackman et al., *Plant Physiol.* 100:225-230 (1992), which is hereby incorporated by reference in its entirety): day 1, 92% RH; day 2, 87% RH; day 3, 75% RH; day 4, 54% RH; day 5, 45% RH; day 6, 32% RH; day 7, 12% RH; and remained at 12% RH days 8-14.

Embryo Feeding Experiments—Substrate Concentration Series

Four substrate concentration experiments were conducted. Embryos for each experiment were incubated in each of the substrate solutions for 24 hours, blotted, and slow dried for 14 days. Axis and cotyledon tissues were separated and analyzed for soluble carbohydrates. Four replications of three embryos each (total of 12 embryos/treatment) were incubated in the myo-inositol-sucrose concentration series: A) 0 mM myo-inositol+100 mM sucrose, B) 10 mM myo-inositol+90 mM sucrose, C) 25 mM myo-inositol+75 mM sucrose, D) 50 mM myo-inositol+50 mM sucrose, E) 100 mM myo-inositol+0 mM sucrose, and F) 0 mM myo-inositol+0 mM sucrose. Six replications of three embryos each (total of 18 embryos/treatment) were incubated in the D-chiro-inositol-sucrose concentration series, and three replications of three embryos each (total of 9 embryos/treatment) were incubated in the D-pinitol-sucrose concentration series. Treatments A) through F) were identical in both concentration series, except for the substitution of D-chiro-inositol or D-pinitol instead of myo-inositol. In the sucrose concentration series, three replications of three embryos (total of 9 embryos/treatment) were incubated with 0, 25, 50, 75, 100, and 200 mM sucrose.

Embryo Feeding Experiments—Drying Time Series

Six slow drying time experiments were conducted. In each experiment, three replications of three embryos each (total of 9 embryos per treatment) were incubated in a different sucrose and/or cyclitol substrate solution for 24 hours, blotted, and slow dried for 0, 1, 2, 3, 4, or 14 days. Axis and cotyledon tissues were separated and analyzed for soluble carbohydrates. The substrate solutions for the six experiments were as follows: 30 mM myo-inositol plus 100 mM sucrose; 100 mM D-chiro-inositol; 100 mM D-pinitol; 100 mM D-pinitol plus 100 mM D-chiro-inositol; 50 mM D-pinitol plus 50 mM D-chiro-inositol; and 100 mM D-pinitol plus 100 mM D-chiro-inositol plus 100 mM sucrose.

Substrates

Sucrose, myo-inositol, scyllo-inositol, epi-inositol, and UDP-Gal were purchased from Sigma-Aldrich (St. Louis, Mo.). D-Pinitol, D-chiro-inositol, L-chiro-inositol, D-ononitol, and L-quebrachitol were purchased from Industrial Research Limited (Lower Hutt, New Zealand). Sequoyitol was purchased from Carl Roth GmbH & Co. KG (Karlsruhe, Germany). Bornesitol was purified from seeds of *Lathyrus odoratus* L. Galactinol was purified from lemon balm (*Melissa officinalis* L.) leaves. When needed, substrates were purified by carbon-Celite column chromatography (Whistler et al., *J. Amer. Chem. Soc.* 72:677-679 (1950), which is hereby incorporated by reference in its entirety) before use. Carbon was purchased from Mallinckrodt Baker Inc (Phillipsburg, N.J.). Celite was purchased from Supelco (Bellefonte, Pa.).

Carbohydrate Analysis

Soluble carbohydrates were extracted from 2 cotyledons or 1 axis for each embryo. Two cotyledons were extracted with 2.0 mL of ethanol:water (1:1, v/v) containing 300 µg of phenyl α-D-glucoside as internal standard. One axis was extracted with 1.0 mL of ethanol:water (1:1, v/v) containing 100 µg of phenyl α-D-glucoside as internal standard. Extracts were passed through a 10,000 molecular weight cut-off filter (NANOSEP 10K Omega, Paul Filton Co., Northborough, Mass.) by centrifugation, and 200 µL were dried in silylation vials under nitrogen gas, derivatized with 200 µL of trimethylsilylsylimidazole:pyridine (1:1, v/v), and analyzed by high resolution gas chromatography on a HP1-MS (Agilent Technologies, Palo Alto, Calif.) capillary column (15 m length, 0.25 mm i.d., 0.25 µm film thickness) as previously described (Horbowicz et al., *Seed Sci. Res.* 4:385-405 (1994), which is hereby incorporated by reference in its entirety).

Results

Cyclitols, including myo-inositol, D-chiro-inositol, and D-pinitol, were fed to immature soybean embryos followed by precocious maturation induced by slow-drying of the embryos and analysis of soluble carbohydrates in axis and cotyledon tissues. Exogenously fed free cyclitols were taken up by embryo tissues. In 250 mg fresh weight embryos, initial concentrations of cyclitols in axis and cotyledon tissues, respectively, were myo-inositol 10.9 and 11.0 mg/g dry weight, D-chiro-inositol 1.4 and 1.2 mg/g dry weight, and D-pinitol 6.0 and 4.0 mg/g dry weight. After incubation with 30 mM myo-inositol, 100 mM D-chiro-inositol, or 100 mM D-pinitol for 24 hours at 22° C., concentrations of myo-inositol increased 1.8 fold in axis and 2 fold in cotyledon tissues, D-chiro-inositol increased 18 fold and 40 fold, and D-pinitol increased 6 fold and 11 fold, respectively.

Both embryonic axis and cotyledon tissues were assayed for experiments reported herein. Embryonic axes mature earlier than cotyledons and accumulate higher concentrations of soluble carbohydrates (up to 25% of dry weight) (Horbowicz et al., *Seed Sci. Res.* 4:385-405 (1994); Obendorf et al., *Crop Sci.* 38:78-84 (1998), which are hereby incorporated by reference in their entirety). Accumulation of products in axis tissues generally precedes accumulation of products in cotyledons, reflecting the differential in progression toward maturation. In general, data were more variable for axis tissues than for cotyledon tissues, mainly because of the small mass of axis tissues, about 1 mg dry weight for experiments reported herein.

Figure 10:
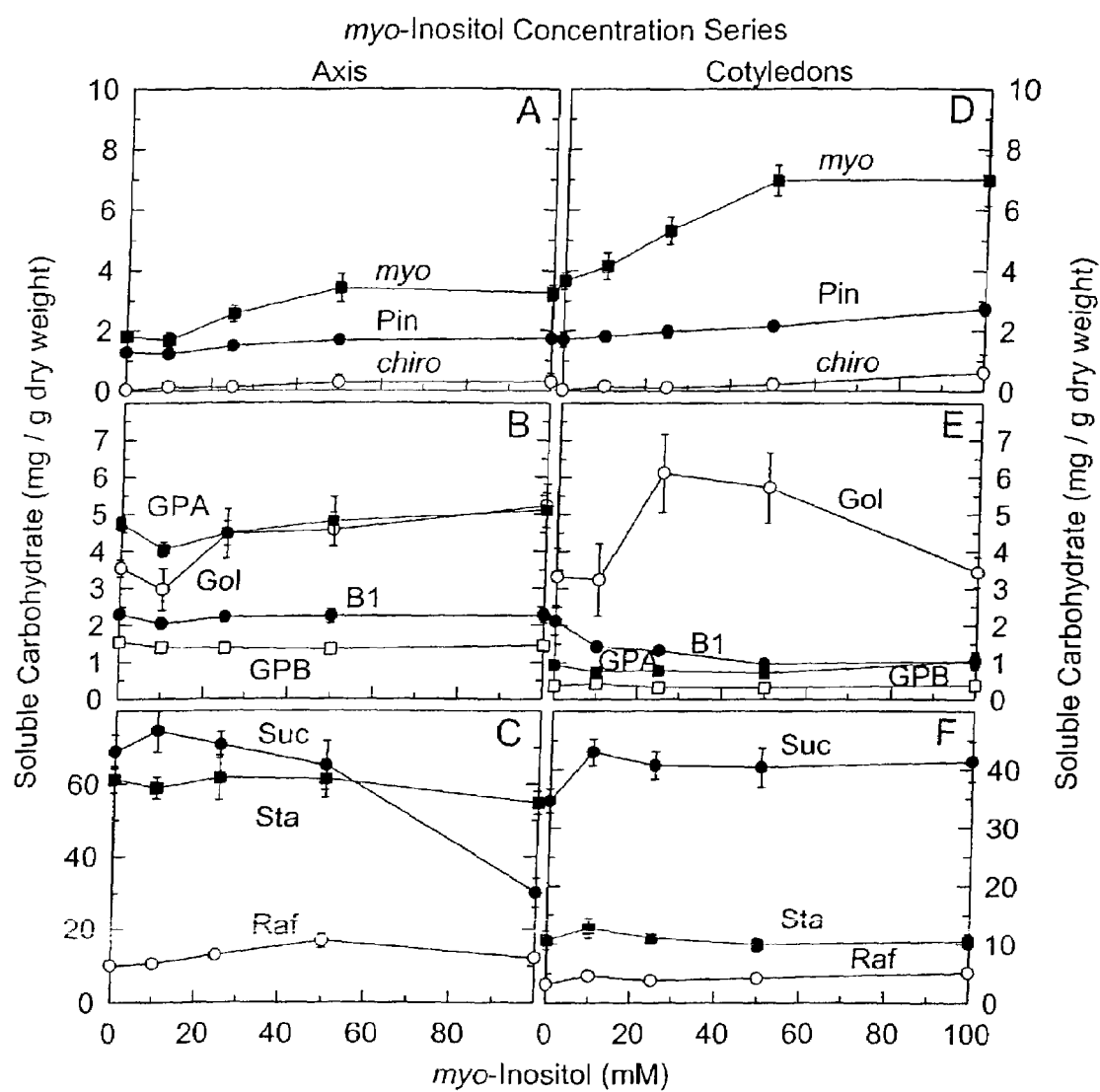
FIGS. 10A-F are graphs showing accumulated soluble carbohydrates in axis and cotyledon tissues after precocious maturation of immature soybean embryos as a function of myo-inositol concentration. The results are shown after feeding myo-inositol (0 to 100 mM) plus sucrose (100 to 0 mM) (100 mM total concentration) for 24 hours at 25° C. followed by 14 days precocious maturation in slow drying series relative humidities. Values are mean ±SE(n=12).
Figure 11:
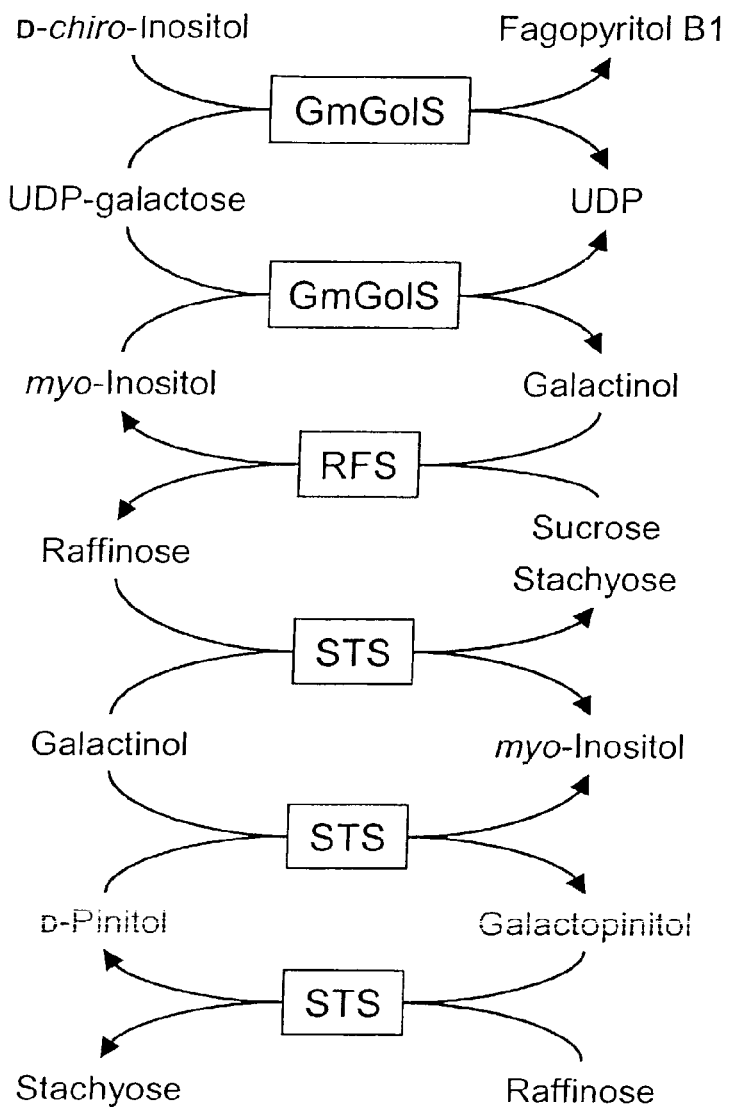
FIG. 11 is a schematic of the proposed pathways for biosynthesis of fagopyritol B1, galactinol, raffinose, stachyose, and galactopinitols. Abbreviations: *Glycine max* galactinol synthase (GmGolS); raffinose synthase (RFS); stachyose synthase (STS).

Concentration series experiments were adjusted to be a constant 100 mM (cyclitol plus sucrose) excluding the sucrose concentration series experiment. Feeding myo-inositol up to 50 mM doubled free myo-inositol concentration in dry axis and cotyledon tissues after precocious maturation with small increases in D-pinitol and D-chiro-inositol (FIGS. 10A and D). Galactinol accumulation doubled in cotyledons after feeding 25 to 50 mM myo-inositol while fagopyritol B1 accumulation was reduced (FIG. 10E), demonstrating a competition between the biosynthesis of galactinol and fagopyritol B1. There was little change in galactopinitol A, galactopinitol B, raffinose, or stachyose concentrations in either axis or cotyledon tissues after feeding myo-inositol (FIGS. 10B, C, E, and F). In the absence of exogenous sucrose, sucrose concentration in axis tissues was reduced to 50%, but sucrose concentration in cotyledons remained constant (FIGS. 10C and F). These results are consistent with the role of myo-inositol as a substrate in galactinol biosynthesis and a product in the biosynthesis of raffinose and stachyose in seeds (FIG. 11). Feeding 30 mM myo-inositol and 100 mM sucrose together resulted in elevated amounts of free myo-inositol during day 1 of slow drying and then a decline in myo-inositol (FIGS. 12A and D), a transient increase in galactinol during days 2 and 3 (FIGS. 12B and E), and then a decline in galactinol as raffinose and stachyose accumulated (FIGS. 12C and F). The decrease in total myo-inositol indicates metabolism of myo-inositol to other products, including phytin and cell walls, within the embryo (Loewus et al., *Plant Sci.* 150:1-19 (2000); Hegeman et al., *Plant Physiol.* 125:1941 1948 (2001); Hitz et al., *Plant Physiol.* 128:650-660 (2002), which are hereby incorporated by reference in their entirety).

Figure 12:
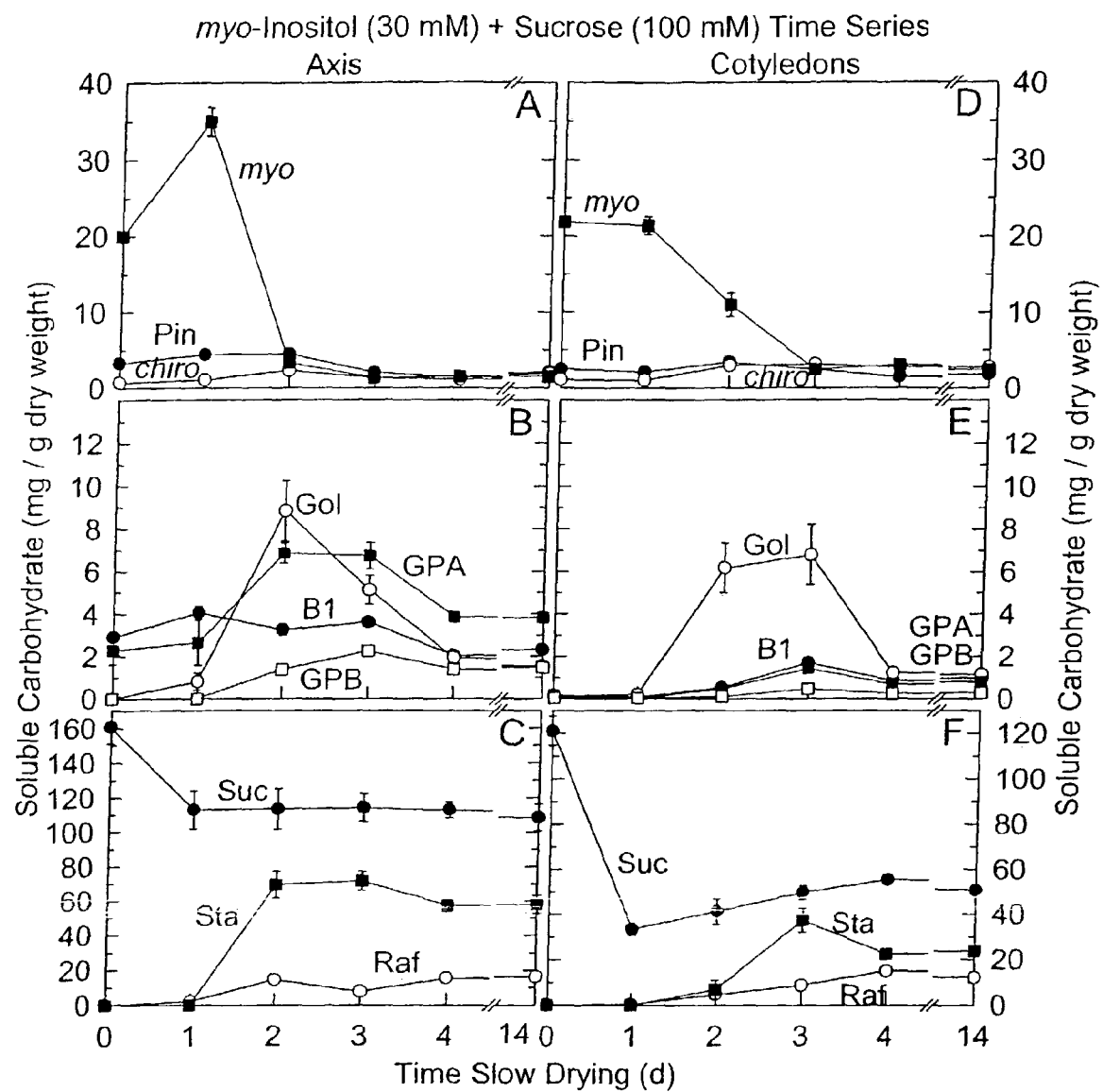
FIGS. 12A-F are graphs showing accumulated soluble carbohydrates in axis and cotyledon tissues after precocious maturation of immature soybean embryos as a function of time of slow drying. The results are shown after feeding 30 mM myo-inositol and 100 mM sucrose for 24 hours at 25° C. followed by 0 to 14 days precocious maturation in slow drying time series relative humidities. Values are mean±SE (n=9).
Figure 13:
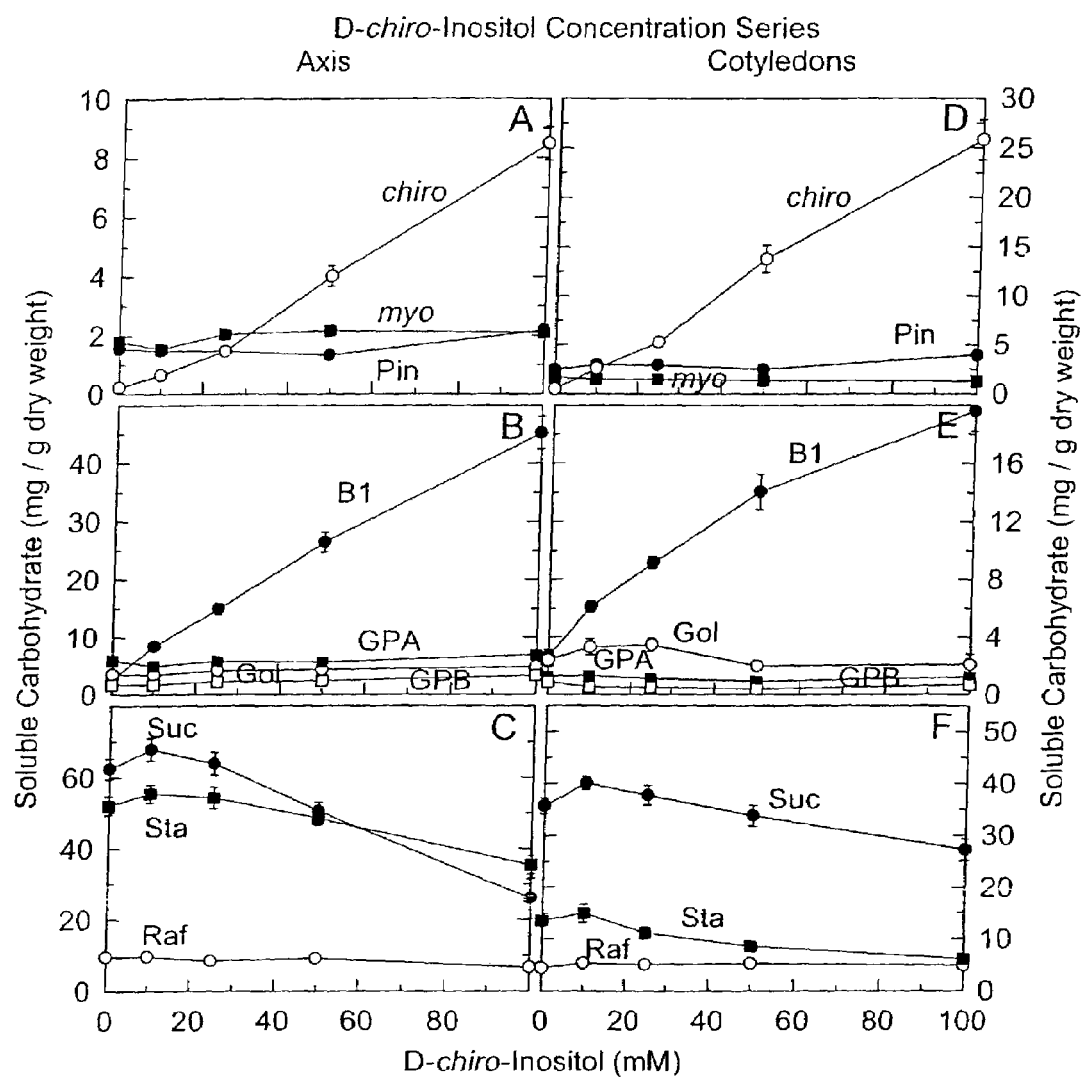
FIGS. 13A-F are graphs showing accumulated soluble carbohydrates in axis and cotyledon tissues after precocious maturation of immature soybean embryos as a function of D-chiro-inositol concentration. The results are shown after feeding D-chiro-inositol (0 to 100 mM) plus sucrose (100 to 0 mM) (100 mM total concentration) for 24 hours at 25° C. followed by 14 days precocious maturation in slow drying series relative humidities. Values are mean ±SE(n=18).
Figure 14:
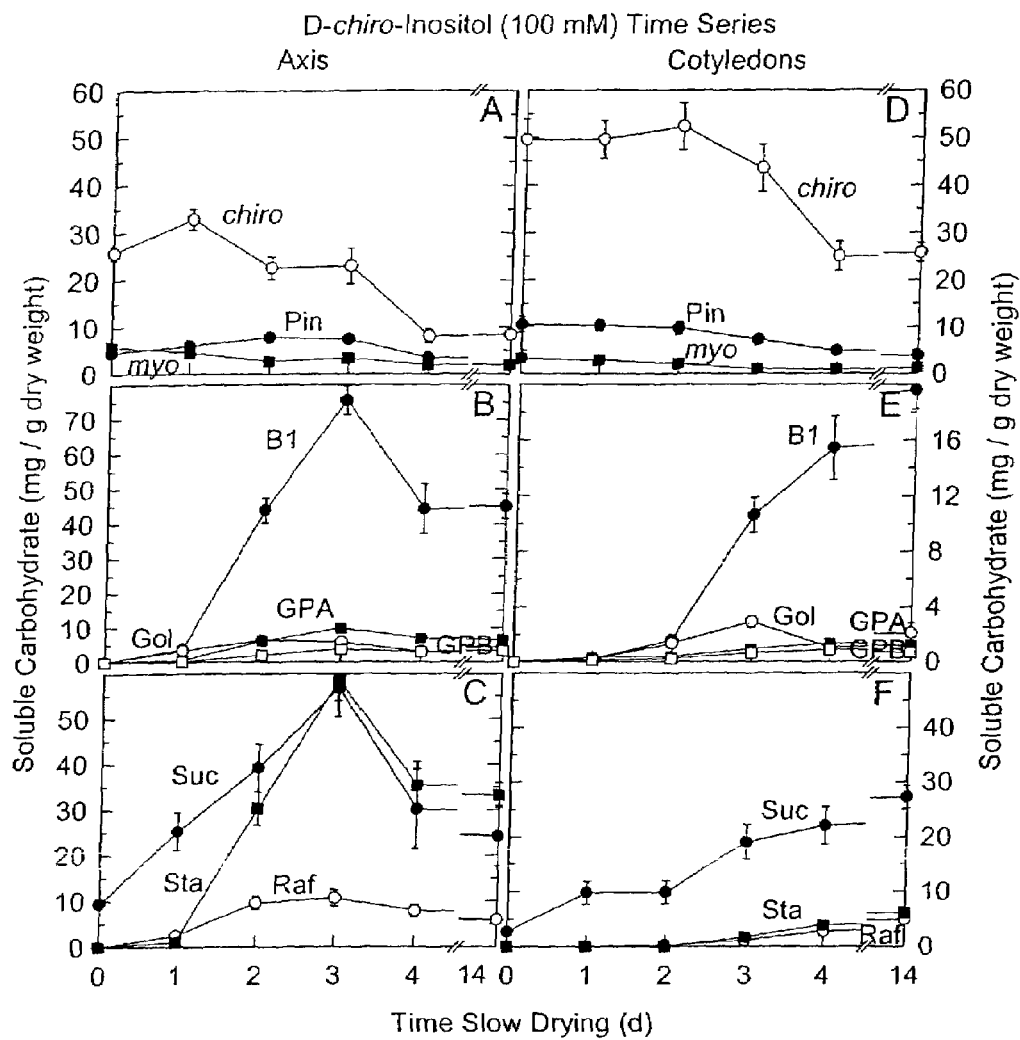
FIGS. 14A-F are graphs showing accumulated soluble carbohydrates in axis and cotyledon tissues after precocious maturation of immature soybean embryos as a function of time of slow drying. The results are shown after feeding 100 mM D-chiro-inositol for 24 hours at 25° C. followed by 0 to 14 days precocious maturation in slow drying time series relative humidities. Values are mean±SE (n=9).

Feeding D-chiro-inositol resulted in a 40- to 50-fold increase in free D-chiro-inositol concentration in axis and cotyledons (FIGS. 13A and D), a 17-fold increase in fagopyritol B1 concentration in axis tissues and a 7-fold increase in cotyledons (FIGS. 13B and E), but did not increase D-pinitol, myo-inositol, galactopinitol A, galactopinitol B, galactinol, raffinose, or stachyose concentrations (FIG. 13). The high concentrations of free D-chiro-inositol declined (FIGS. 14A and D) and a large increase in fagopyritol B1 occurred between day 2 and day 4 of slow drying accompanied by the decrease in concentration of free D-chiro-inositol in axis and cotyledon tissues (FIGS. 14A, B, D, and E). A transient accumulation of galactinol signaled an accumulation of raffinose and stachyose and modest accumulation of galactopinitol A and galactopinitol B (FIGS. 14B, C, E, and F, compared to FIG. 12). These results suggest that D-chiro-inositol does not serve as precursor to myo-inositol or D-pinitol in soybean embryos, and that fagopyritol B1 does not serve as an alternate galactosyl donor for the biosynthesis of raffinose and stachyose. The large increase in fagopyritol B1 from externally applied D-chiro-inositol suggests that D-chiro-inositol is not biosynthesized within the embryo but is transported to the embryo from maternal tissues. The increase in sucrose during slow drying (FIGS. 14C and F) probably reflects starch degradation within the embryo.

Figure 15:
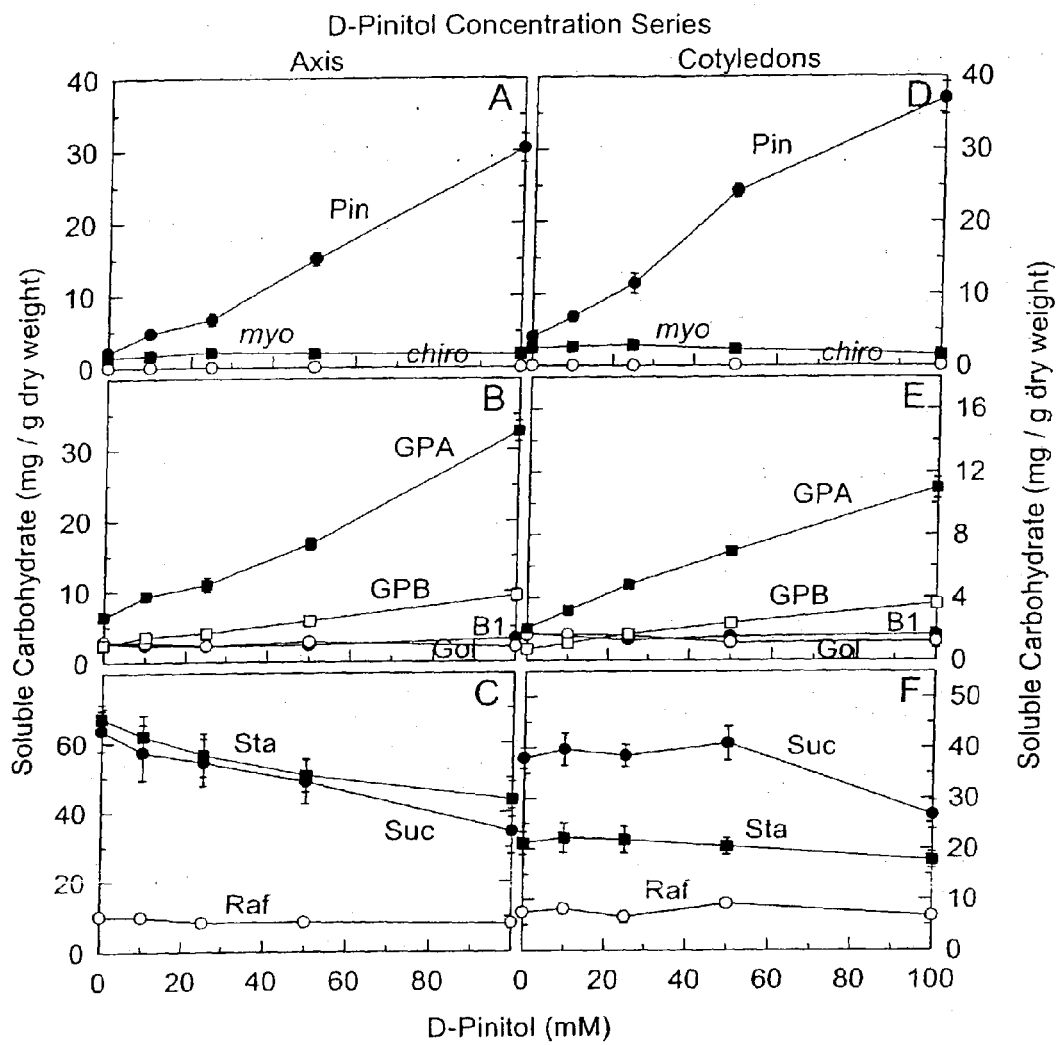
FIGS. 15A-F are graphs showing accumulated soluble carbohydrates in axis and cotyledon tissues after precocious maturation of immature soybean embryos as a function of D-pinitol concentration. The results are shown after feeding D-pinitol (0 to 100 mM) plus sucrose (100 to 0 mM) (100 mM total concentration) for 24 hours at 25° C. followed by 14 days precocious maturation in slow drying series relative humidities. Values are mean±SE (n=9).
Figure 16:
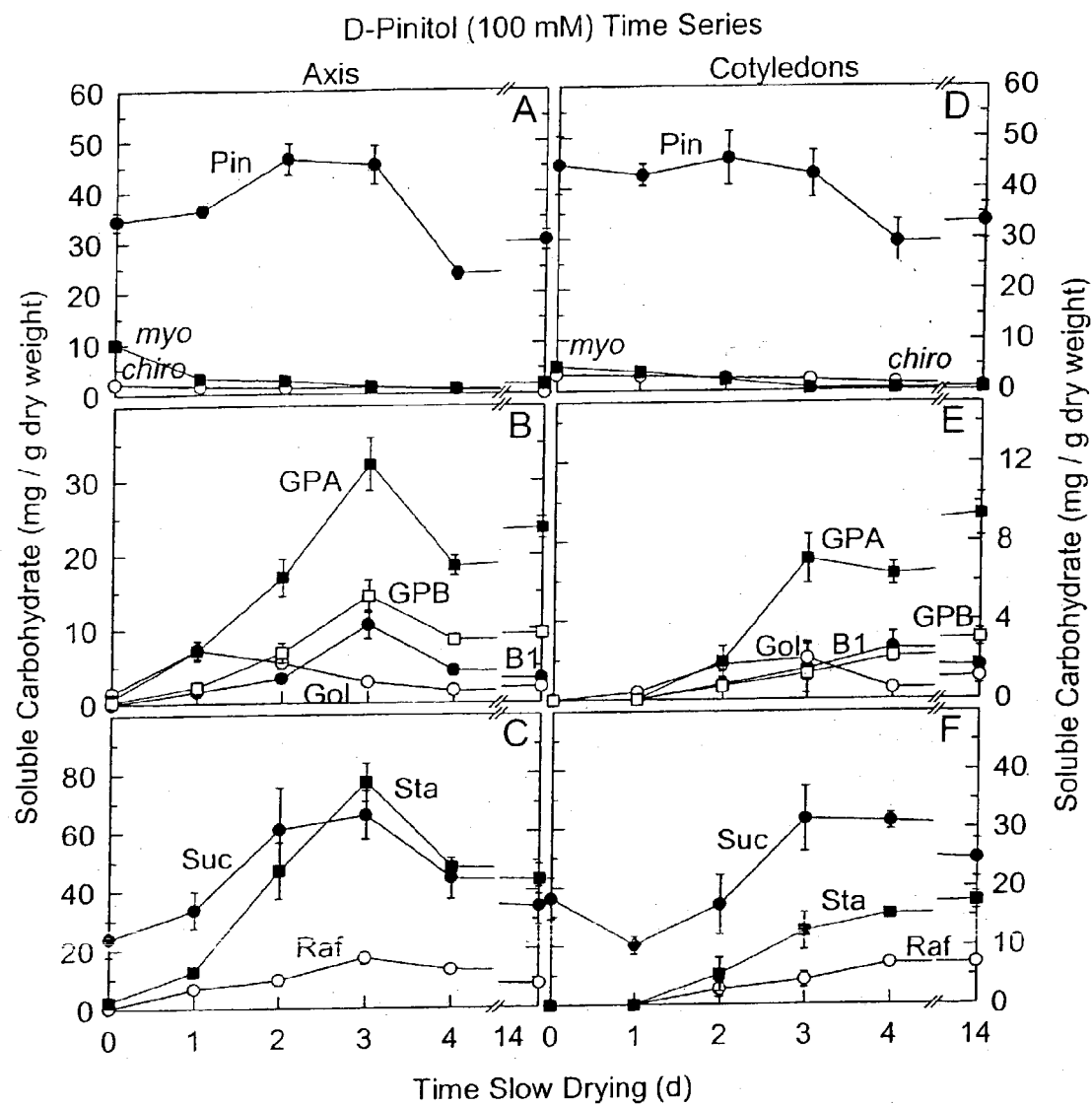
FIGS. 16A-F are graphs showing accumulated soluble carbohydrates in axis and cotyledon tissues after precocious maturation of immature soybean embryos as a function of time of slow drying. The results are shown after feeding 100 mM D-pinitol for 24 hours at 25° C. followed by 0 to 14 days precocious maturation in slow drying time series relative humidities. Values are mean±SE (n=9).

Feeding D-pinitol resulted in an 8-fold increase in free D-pinitol concentration (FIGS. 15A and D) and a more than 4-fold increase in both galactopinitol A and galactopinitol B concentrations (FIGS. 15B and E). Concentrations of D-chiro-inositol, myo-inositol, fagopyritol B1, galactinol, raffinose, and stachyose were not increased (FIG. 15). Feeding 100 mM D-pinitol resulted in high concentrations of free D-pinitol and a substantial increase in galactopinitol A and galactopinitol B between day 2 and day 4 of slow drying (FIGS. 16A, B, D, and E). A transient increase in galactinol occurred as raffinose and stachyose accumulated (FIGS. 16B, C, E, and F). The larger increase in stachyose in cotyledons, compared to feeding D-chiro-inositol (FIG. 14F), suggests that galactopinitol A may be effective as a galactosyl donor for stachyose biosynthesis as suggested by Hoch et al., *Arch. Biochem. Biophys.* 366:75-81 (1999) and Peterbauer et al., *Seed Sci. Res.* 11:185-198 (2001), which are hereby incorporated by reference in their entirety. The large increase in galactopinitols from externally applied D-pinitol suggests that D-pinitol is not biosynthesized within the embryo but is transported to the embryo from maternal tissues. Sucrose concentration increased through day 3 of slow drying (FIGS. 16C and F).

Figure 17:
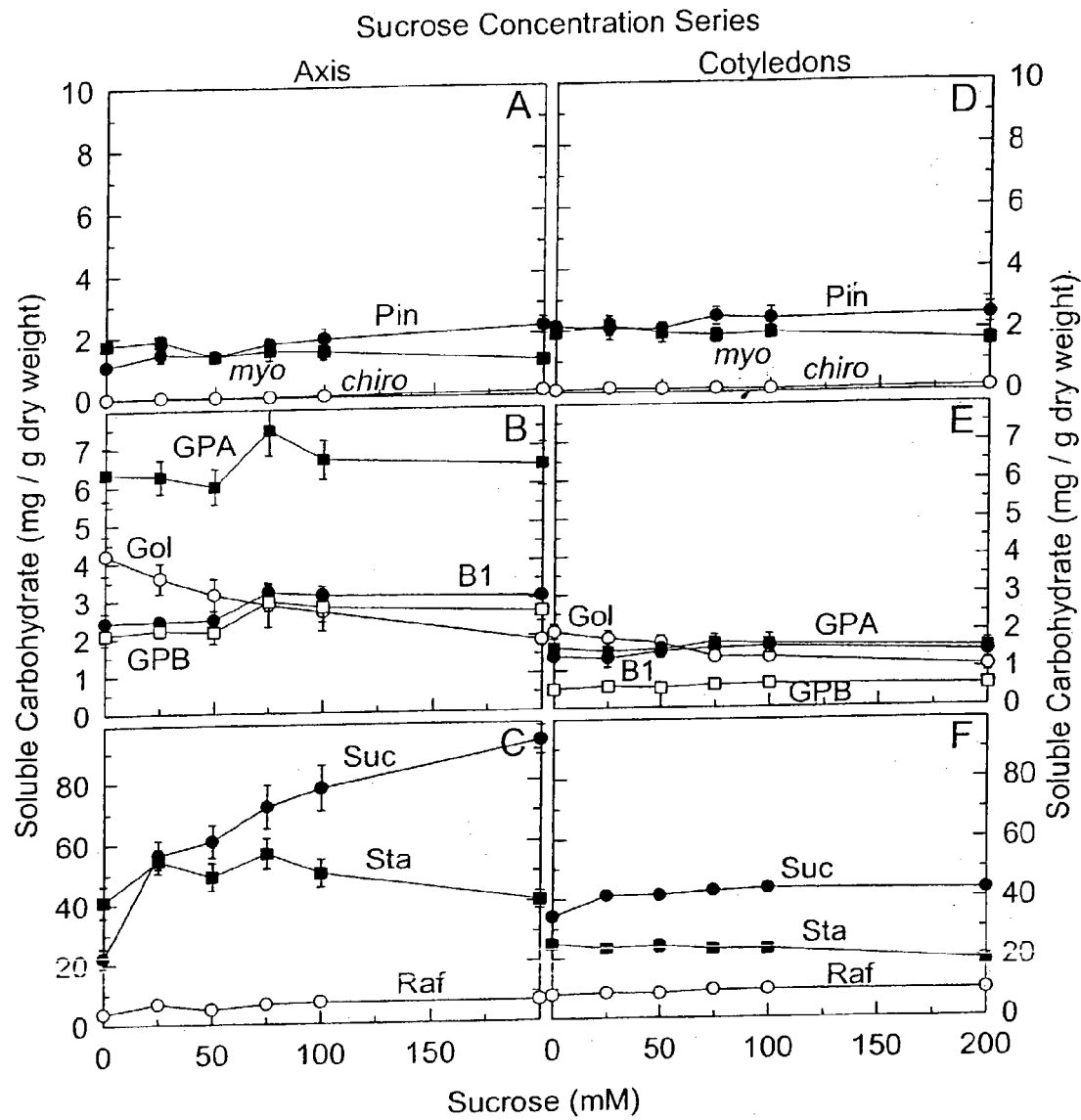
FIGS. 17A-F are graphs showing accumulated soluble carbohydrates in axis and cotyledon tissues after precocious maturation of immature soybean embryos as a function of sucrose concentration. The results are shown after feeding sucrose (0 to 200 mM) for 24 hours at 25° C. followed by 14 days precocious maturation in slow drying series relative humidities. Values are mean±SE (n=9).

Feeding sucrose at 0 to 200 mM resulted in a small decrease in galactinol (FIG. 17B) and an increase in sucrose in axis tissues (FIG. 17C) but little change in concentrations of soluble carbohydrates in cotyledon tissues (FIG. 17). These results suggest that osmotic concentrations, per se, have little effect on soluble carbohydrate concentrations under the experimental conditions used in these experiments.

Figure 18:
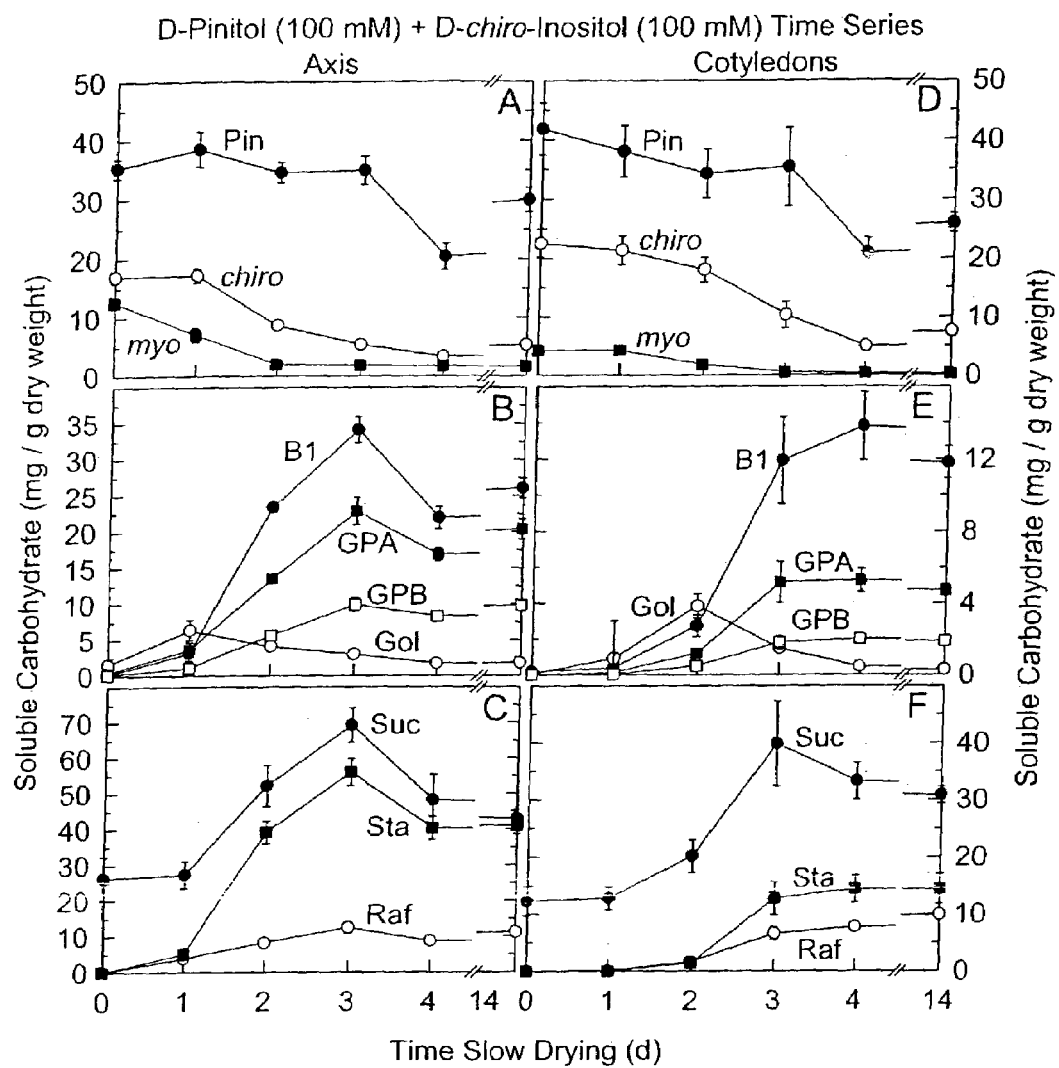
FIGS. 18A-F are graphs showing accumulated soluble carbohydrates in axis and cotyledon tissues after precocious maturation of immature soybean embryos as a function of time of slow drying. The results are shown after feeding 100 mM D-chiro-inositol and 100 mM D-pinitol for 24 hours at 25° C. followed by 0 to 14 days precocious maturation in slow drying time series relative humidities. Values are mean±SE (n=9).

Feeding a combination of 100 mM D-pinitol and 100 mM D-chiro-inositol resulted in high concentrations of both free D-pinitol and free D-chiro-inositol; free D-chiro-inositol declined with elevated concentrations of fagopyritol B1, D-pinitol decreased less but with increases in galactopinitol A, galactopinitol B, stachyose, and raffinose between day 2 and day 3 in embryo cotyledon tissues (FIG. 18). Galactinol concentration peaked by day 1 (axis) or day 2 (cotyledons) and declined as raffinose, stachyose, and galactopinitols accumulated.

Accumulation of fagopyritol B1 appeared to be independent of accumulation of galactopinitols, raffinose, and stachyose, indicating fagopyritol B1 biosynthesis is independent of galactopinitol biosynthesis. Feeding a combination of D-pinitol and D-chiro-inositol (FIG. 18) resulted in a 50% decrease (14 days in steady state galactinol concentration and a 50% decrease (14 days) in galactopinitol A plus galactopinitol B concentration in cotyledons (FIG. 18E), compared to feeding D-pinitol alone (FIG. 16E), but only a 10 to 15% decrease (4 days) in fagopyritol B1 concentration (FIG. 18E) compared to feeding D-chiro-inositol alone (FIG. 14E) (14 versus 16 mg/g DW at day 4 of slow drying). In axis tissues, galactinol, galactopinitol A, galactopinitol B, raffinose, and stachyose were not decreased by feeding a combination of D-pinitol and D-chiro-inositol (FIGS. 18C and D) compared to feeding D-pinitol alone (FIGS. 16C and D). Fagopyritol B1 in axis tissues was reduced about 50% (14 days) after feeding a combination of D-pinitol and D-chiro-inositol (FIG. 18B) compared to feeding D-chiro-inositol alone (FIG. 14B). In all cases, fagopyritol B1 was maximum in axis tissues on day 3 of slow drying while in cotyledons fagopyritol B1 continued to increase during day 4 of slow drying. The small mass of the axis tissues (approximately 1 mg dry weight) may have hastened the cessation of galactosyl cyclitol accumulation in axis tissues compared to cotyledons during precocious maturation. In addition, axis tissues yellowed 1 to 2 days sooner during precocious maturation after feeding D-pinitol or combinations of D-pinitol and D-chiro-inositol than after feeding D-chiro-inositol alone. Feeding a combination of 50 mM D-pinitol plus 50 mM D-chiro-inositol resulted in patterns identical to those with 100 mM (FIG. 18), indicating the cyclitol substrates were at saturating concentrations. Feeding a combination of 100 mM D-pinitol, 100 mM D-chiro-inositol, and 100 mM sucrose resulted in patterns identical to those without sucrose (FIG. 18), except that sucrose concentrations were higher initially.

Cyclitols detected in soybean embryos include myo-inositol, D-pinitol, and D-chiro-inositol (Horbowicz et al., *Seed Sci. Res.* 4:385-405 (1994); Obendorf et al., *Plant Sci.* 132:1-12 (1998); Obendorf et al., *Crop Sci.* 38:78-84 (1998), which are hereby incorporated by reference in their entirety). If present, other cyclitols were below the level of detection. myo-Inositol is biosynthesized in soybean embryos, and inhibition of myo-inositol biosynthesis results in reduced accumulation of phytic acid, galactinol, raffinose, and stachyose (Hegeman et al., *Plant Physiol.* 125:1941-1948 (2001); Hitz et al., *Plant Physiol.* 128:650-660 (2002), which are hereby incorporated by reference in their entirety). Total D-chiro-inositol or total D-pinitol did not increase in the absence of exogenous feeding of the corresponding cyclitols, consistent with our previous results with soybean zygotic embryos matured in vitro (Obendorf et al., *Plant Sci.* 132:1-12 (1998); Obendorf et al., *Crop Sci.* 38:78-84 (1998), which are hereby incorporated by reference in their entirety) and indicating a lack of biosynthesis of both D-chiro-inositol and D-pinitol during precocious maturation of soybean zygotic embryos.

Axis tissues accumulate higher concentrations of soluble carbohydrate products than cotyledons, suggesting that biosynthetic enzymes may be more active in axis tissues. Yellowing of axis and cotyledon tissues is a visual indicator of the cessation of growth and tissue maturation; axis tissues mature earlier than cotyledon tissues in planta (Obendorf et al., *Crop Sci*. 38:78-84 (1998), which is hereby incorporated by reference in its entirety). This difference in maturation must be considered when assaying gene expression in whole embryos or seeds in contrast to assaying axis and cotyledon tissues separately. Feeding D-pinitol or combinations of D-pinitol and D-chiro-inositol resulted in yellowing of axis tissues 1 to 2 days earlier during precocious maturation than feeding D-chiro-inositol alone. Because of their small size and more rapid maturation rate after feeding D-pinitol, precociously matured axis tissues may not reflect product accumulation patterns as accurately as cotyledons. Therefore, more emphasis should be placed on the product accumulation patterns in precociously matured cotyledons.

Feeding both D-pinitol and D-chiro-inositol reduced galactinol concentration in cotyledons by 50% compared to feeding D-pinitol alone, indicating a competition between the biosynthesis of fagopyritol B1 and galactinol by GolS. The 50% reduction in the biosynthesis of galactopinitols reflects the 50% reduction in galactinol, the galactosyl donor for galactopinitol biosynthesis by stachyose synthase (Peterbauer et al., *Seed Sci. Res*. 11:185-198 (2001), which is hereby incorporated by reference in its entirety). The small decrease in fagopyritol B1 biosynthesis after feeding both D-pinitol and D-chiro-inositol compared to feeding D-chiro-inositol alone, probably reflects competition for available UDP-Gal between galactinol and fagopyritol B1 biosynthesis. Results of substrate feeding experiments are consistent with the interpretation that D-pinitol and D-chiro-inositol are transported from maternal tissues and not biosynthesized in the embryo tissues. In addition, galactopinitols and fagopyritol B1 are biosynthesized by different pathways, fagopyritols are biosynthesized by GolS, galactopinitols are biosynthesized by stachyose synthase/raffinose synthase, and galactopinitols may serve as galactosyl donors for stachyose biosynthesis.

Example 3

Soybean EST Clone Corresponding to Galactinol Synthase (GolS) Gene

Gene or cDNA sequences corresponding to the GolS gene in soybean were searched in the nucleotide and protein databases using the BLAST programs (http://www.ncbi.nlm.nih.gov) and a multiple sequence alignment program, CLUSTAL W (http://workbench.sdsc.edu). A soybean EST clone (GenBank accession number BE330777) sharing a very high level of DNA sequence identity with the GolS genes reported from other plant species was identified, and obtained from INCYTE GENOMICS, Palo Alto, Calif. (cat. no. Gm-c1041). Since only partial DNA sequence data were available for this EST clone in GenBank, the whole EST insert was re-sequenced (nucleotide sequence assigned to GenBank Accession Number AY126715) at the DNA Sequencing Facility at BioResource Center at Cornell University (http://brcweb.biotech.cornell.edu).

The 987 bp long entire protein coding sequence of GmGolS was amplified from the soybean EST clone by PCR. Two primers, 5'-CATCACTGAGCATATGGCTGG-3' (SEQ ID NO:29) and 5'-GGATCCAAAGACACTCTTAAGCAG-CAGATGGGG-3' (SEQ ID NO:30), containing NdeI and BamHI restriction enzyme recognition sites respectively, were used in the PCR assays. After cloning into the pCRII-TOPO vector (Invitrogen, Carlsbad, Calif.) and amplification in *Escherichia coli*, the NdeI/BamHI fragment containing the entire protein coding sequence was isolated and cloned into the corresponding sites in pET-14b vector (Novagen, Madison, Wis.). This insertion resulted in the placement of the GmGolS protein coding sequence in frame with the preceding poly-histidine codons in the pET-14b vector. The pET14b plasmid containing soybean GmGolS cDNA was mobilized into *E. coli* strain BL21 (DE3) (Novagen, Madison, Wis.). Expression of the recombinant GmGolS protein was induced in *E. coli* with 1 mM isopropylthio-β-D-galactoside (IPTG) according to the manufacturer's recommended protocol (Novagen, Madison, Wis.). The bacterial cells were collected by centrifugation, and resuspended in 10 mM Tris-HCl buffer (pH 8.0). The soluble protein fraction was extracted from the bacterial cells by the gentle disruption of their cell walls with BugBuster Protein Extraction Reagent (Novagen, Madison, Wis.) containing Benzonase (Novagen, Madison, Wis.). Poly-histidine tagged recombinant proteins were purified from the extracts using His.Bind Quick 900 Cartridges (Novagen, Madison, Wis.) according to the manufacturer's recommended protocol. Purification of proteins was verified by SDS-PAGE. Purified recombinant proteins were dialyzed against 50 mM HEPES [4-(2-hydroxyethyl)-1-piperazineethanesulfonic acid]-NaOH buffer, pH 7.0, containing 5 mM $MnCl_2$, immediately after elution from the His.Bind Quick 900 Cartridges and prior to enzyme assay.

Both crude soluble protein extracts from *E. coli* containing the recombinant GmGolS protein and purified recombinant GmGolS protein were used in enzyme assays. GolS activity assays included 20 mM UDP-Gal as the galactosyl donor, 20 mM myo-inositol as the galactosyl acceptor, 50 mM HEPES buffer, pH 7.0, 2 mM DTT, 5 mM $MnCl_2$ and 1 to 5 µg of crude protein extract or purified GmGolS protein in 50 µL total volume. In fagopyritol synthase assays, myo-inositol was substituted with 20 mM D-chiro-inositol as the galactosyl acceptor. Assays were run at 30° C. for 30 to 300 minutes. Reactions were stopped by addition of 50 µL of 100% ethanol. After addition of 25 µg of phenyl α-D-glucoside as internal standard, the reaction mixture was heated at 80° C. for 30 minutes, passed through a 10,000 MW cutoff filter (NANOSEP), and evaporated to dryness under a stream of nitrogen gas. Residues were stored overnight in a desiccator with phosphorus pentoxide to remove traces of water, derivatized with trimethylsilylimidazole:pyridine (1:1, v/v) at 80° C. for 45 minutes, and analyzed for fagopyritols or other soluble carbohydrate products by high resolution gas chromatography on a HP1-MS (Agilent Technologies) capillary column as previously described (Horbowicz et al., *Seed Sci. Res*. 4:385-405 (1994), which is hereby incorporated by reference in its entirety).

Figure 19:
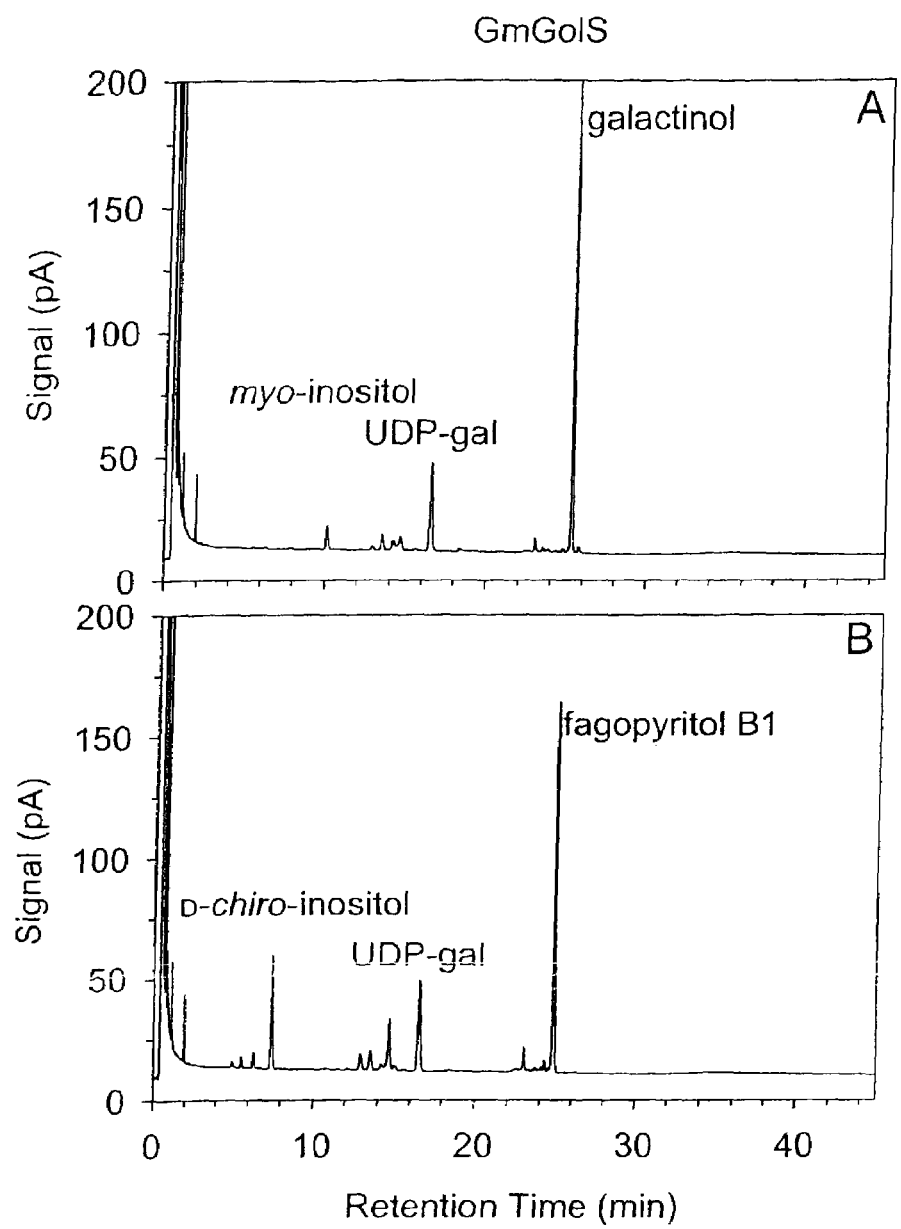
FIGS. 19A-B show GmGolS products.

To confirm that GolS catalyzes the biosynthesis of fagopyritol B1, a soybean galactinol synthase (GmGolS) gene was cloned (GenBank accession number AY126715) and heterologously expressed in *Escherichia coli*. The purified recombinant protein was assayed for fagopyritol synthase activity. Recombinant GmGolS catalyzed the biosynthesis of galactinol with UDP-Gal as the galactosyl donor and myo-inositol as the galactosyl acceptor (FIG. 19A), but also catalyzed the biosynthesis of fagopyritol B1 with UDP-Gal as the galactosyl donor and D-chiro-inositol as the galactosyl receptor (FIG. 19B). GmGolS was not active with galactinol as the galactosyl donor. Using UDP-Gal as the galactosyl donor, GmGolS was not active with O-methylated cyclitols including D-pinitol (1D-3-O-methyl-chiro-inositol), D-ononitol (1D-4-O-methyl-myo-inositol), sequoyitol (5-O-methyl-myo-inositol), or L-quebrachitol (1L-2-O-methyl-chiro-inositol) as galactosyl acceptors, except for reduced activity with D-bornesitol (1D-1-O-methyl-myo-inositol). GmGolS was active with L-chiro-inositol as the galactosyl acceptor, but had reduced activity with scyllo-inositol and no activity with epi-inositol using UDP-Gal as galactosyl donor.

The recombinant soybean galactinol synthase (GmGolS) is a multi-functional enzyme with both GolS activity and fagopyritol synthase activity, but GmGolS does not exhibit galactopinitol synthase activity. GolS activity in developing and maturing soybean seeds is associated with stachyose accumulation and remained high through seed maturity (Handley et al., *J. Amer. Soc. Hort. Sci.* 108:600-605 (1983); Saravitz et al., *Plant Physiol.* 83:185-189 (1987); Lowell et al., *Crop Sci.* 29:459-465 (1989); Kuo et al., *Plant Sci.* 125: 1-11 (1997), which are hereby incorporated by reference in their entirety). During soybean seed development in planta, GolS mRNA was first detected in axis tissues at 44 days post anthesis (DPA) and in cotyledons at 46 to 48 DPA (Volk, *Ph.D. Dissertation*, Cornell University, Ithaca, N.Y., pp 176-187 (1998), which is hereby incorporated by reference in its entirety), coincident with galactinol accumulation and at the onset of stachyose accumulation (Obendorf et al., *Crop Sci.* 38:78-84 (1998), which is hereby incorporated by reference in its entirety). GolS transcripts remained high during seed desiccation (Volk, *Ph.D. Dissertation*, Cornell University, Ithaca, N.Y., pp 176-187 (1998), which is hereby incorporated by reference in its entirety). GolS enzyme activity and mRNA increase in response to cold or desiccation (Castillo et al., *J. Agric. Food Chem.* 38:351-355 (1990); Liu et al., *Plant Sci.* 134:11-20 (1998), which are hereby incorporated by reference in their entirety). Among seven *Arabidopsis thaliana* GolS genes, three were stress responsive (Taji et al., *Plant J.* 29:417-426 (2002), which is hereby incorporated by reference in its entirety). AtGolS1 and AtGolS2 were induced by water-deficit stress and high-salinity stress but not by cold stress. AtGolS3 was induced by cold stress but not by drought or salt stress. Soybean seeds matured at 25° C. had increased D-chiro-inositol and fagopyritol B1 compared to seeds matured at 18° C., but galactinol remained unchanged (Obendorf et al., *Crop Sci.* 38:78-84 (1998), which is hereby incorporated by reference in its entirety), indicating a lack of response to a lower temperature. Similarly, tomato (*Lycopersicon esculentum* Mill.) seed GolS (LeGolS-1) mRNA increased in maturing seeds before desiccation, was concentrated in the radicle tip of mature dry seeds, was induced by desiccation but not cold in germinating seeds, and was induced by both desiccation and cold in seedling leaves (Downie et al., *Plant Physiol.* 131:1347-1359 (2003), which is hereby incorporated by reference in its entirety).

Substrate specificities of soybean GolS and stachyose synthase are different. The lack of soybean GolS activity with D-pinitol, D-ononitol, and sequoyitol as galactosyl acceptors contrasts with the activity of stachyose synthase with these O-methylated cyclitols (Peterbauer et al., *Plant Physiol.* 117: 165-172 (1998); Hoch et al., *Arch. Biochem. Biophys.* 366: 75-81 (1999); Peterbauer et al., *J. Biol. Chem.* 277:194-200 (2002), which are hereby incorporated by reference in their entirety). Likewise, activity of GmGolS with D-bornesitol contrasts with the lack of activity of stachyose synthase with D-bornesitol or L-bornesitol (Peterbauer et al., *Plant Physiol.* 117:165-172 (1998); Hoch et al., *Arch. Biochem. Biophys.* 366:75-81 (1999), which are hereby incorporated by reference in their entirety). Lentil (*Lens culinaris* Medic.) stachyose synthase has been demonstrated to catalyze the biosynthesis of galactopinitols (Hoch et al., *Arch. Biochem. Biophys.* 366:75-81 (1999), which is hereby incorporated by reference in its entirety); this enzyme had low activity with D-chiro-inositol and no activity with L-chiro-inositol. By contrast, adzuki bean (*Vigna angularis* Ohwi and Ohashi) stachyose synthase had only a trace of activity with D-pinitol and no activity with D-chiro-inositol or L-chiro-inositol (Peterbauer et al., *Plant Physiol.* 117:165-172 (1998), which is hereby incorporated by reference in its entirety). A recombinant raffinose synthase from pea (*Pisum sativum* L.) seeds was active with D-ononitol and D-pinitol to form galactosyl ononitol and galactosyl pinitol using galactinol as the galactosyl donor (Peterbauer et al., *Planta* 215:839-846 (2002), which is hereby incorporated by reference in its entirety). This *Pisum sativum* raffinose synthase also exhibited a neutral α-galactosidase activity (Peterbauer et al., *Planta* 215:839-846 (2002), which is hereby incorporated by reference in its entirety), consistent with its amino acid sequence similarity to a family of alkaline α-galactosidases (Seed Imbibition Proteins, SIPs) (Carmi et al., *Plant J.* 33:97-106 (2003), which is hereby incorporated by reference in its entirety). A multi-functional pea seed stachyose synuthase had low activities for biosynthesis of galactopinitol and verbascose (Peterbauer et al., *J. Biol. Chem.* 277:194-200 (2002), which is hereby incorporated by reference in its entirety). Collectively, these observations demonstrate substrate specificity of these multi-functional enzymes to be species-specific and product accumulation to be dependent upon the availability of specific cyclitol substrates to the embryo tissues. Clearly, GmGolS can catalyze the biosynthesis of fagopyritol B1, but not galactopinitols, in maturing soybean embryos.

Example 4

Biosynthesis of Fagopyritol B1 and Galactopinitols in Soybean Explants Following Feeding With Free Cyclitols Soybean is a leguminous plant that bears monocarpic fruit only once before death. During maturation, tissues become yellow starting with radical tips, leaf blades, pod walls, hypocotyls, and cotyledons (Benner et al., *Biochemie und Physiologie der Pflanzen* 179:269-275 (1984), which is incorporated herein by reference in its entirety). Yellowing of the seed coat and embryo indicate cessation of dry matter accumulation in the seed (TeKrony et al., *Agronomy Journal* 73:553-556 (1981); VerNooy et al., *Plant Physiology* 82:222-225 (1986), which are hereby incorporated by reference in their entirety). Leaf yellowing, however, is not always a good indicator of when a given soybean seed has stopped growing (Neumann et al., *Plant Physiology* 72:182-185 (1983), which is incorporated herein by reference in its entirety). Because there is transport from the leaves to the pod, seed weight may continue to increase as long as leaves are still alive. Consequently, pod yellowing is the indicator that is often used to determine the time at which maximum dry weight is reached (Benner et al., *Biochemie und Physiologie der Pflanzen* 179: 269-275 (1984), which is incorporated herein by reference in its entirety). The onset of this yellowing/desiccation is what brings about galactosyl cyclitol accumulation in axis and cotyledon tissue (Obendorf et al., *Plant Science* 132:1-12 (1998); Obendorf et al., *Crop Science* 38:78-84 (1998), which are incorporated herein by reference in their entirety).

Soybean seeds accumulate galactosyl cyclitols as opposed to free cyclitols (Horbowicz et al., *Seed Science Research*

4:385-405 (1994), which is incorporated herein by reference in its entirety). These include galactosyl derivatives of D-pinitol, D-chiro-inositol, and myo-inositol in soybean seeds (Obendorf et al., *Crop Science* 38:78-84 (1998), which is incorporated herein by reference in its entirety). Among the fifteen soluble carbohydrates or maturation sugars are sucrose, raffinose and stachyose (raffinose oligosaccharides series), galactopinitol A and galactopinitol B (galactopinitol series), and fagopyritol B1 (fagopyritol series) (Schweizer et al., *Carb. Res.* 95:61-71 (1981); Obendorf et al., *Plant Science* 132:1-12 (1998); Obendorf et al., *Crop Science* 38:78-84 (1998), which are incorporated herein by reference in their entirety). Soluble carbohydrates of this type may have multiple functions in the desiccation tolerance of maturing seeds. They are harmless forms of seed storage products and intracellular osmotic agents contributing to the structural stability of organelles, membranes, enzymes, proteins, and other macromolecules (Obendorf, *Seed Science Research* 7:63-74 (1997), which is hereby incorporated by reference in its entirety).

Upon being fed to soybean, free cyclitols undergo biosynthetic reactions to form galactosyl cyclitols. Several important reactions of myo-inositol, D-chiro-inositol, and D-pinitol will be discussed hereafter. Firstly, myo-inositol is encountered in all living cells and is the primary source for the biosynthesis of various cyclitols. Feeding myo-inositol to soybean promotes the production of galactinol. The three components of the galactinol series are myo-inositol, galactinol, and digalactosyl myo-inositol. Galactinol is far-reaching in its ability to donate galactose for the formation of stachyose, raffinose, and verbascose (Peterbauer et al., *Seed Science Research* 11:185-198 (2001); Taji et al., *Plant Journal* 29:417-426 (2002), which are incorporated herein by reference in their entirety). If galactose is donated to another galactinol molecule, digalactosyl myo-inositol is formed. Secondly, feeding D-pinitol enhances accumulation of galactopinitol A and galactopinitol B common in legume seeds (Odorcic et al., *The Biology of Seeds: Recent Research Advances*. Wallingford, UK, CABI Publishing (2003), which is incorporated herein by reference in its entirety). As stachyose accumulates during soybean seed maturation, galactopinitols also increase (Obendorf et al., *Crop Science* 38:78-84 (1998), which is incorporated herein by reference in its entirety). In addition to this, galactopinitols accumulate during precocious maturation of immature seeds. Lastly, feeding of D-chiro-inositol results in enhanced accumulation of fagopyritol B1 (Odorcic et al., *The Biology of Seeds: Recent Research Advances*. Wallingford, UK, CABI Publishing (2003), which is incorporated herein by reference in its entirety). The fagopyritol B series enhanced through feeding consists of fagopyritol B1 (first identified in soybean seeds), D-chiro-inositol, fagopyritol B2, and fagopyritol B3, which accumulate in buckwheat seeds (Obendorf, *Seed Science Research* 7:63-74 (1997); Horbowicz et al., *Planta* 205:1-11 (1998), which are incorporated herein by reference in their entirety). A novel series of fagopyritols, fagopyritol A1, fagopyritol A2, and fagopyritol A3, also accumulate in buckwheat seeds (Horbowicz et al., *Planta* 205:1-11 (1998); Obendorf et al., *Carbohydrate Research* 328:623-627 (2000); Steadman et al., *Carbohydrate Research* 331:19-25 (2001), which are incorporated herein by reference in their entirety).

Knowledge of the translocation patterns of cyclitols is indispensable in understanding their function (Noodén et al., *Journal of Plant Growth Regulation* 2:265-279 (1984), which is incorporated herein by reference in its entirety). Previous studies used labeled chemicals, hormones, or sugars in order to observe these very translocation patterns within plants of interest. In an experiment done by Noodén and Letham in 1983, for example, $^3$H (ring-labeled) zeatin riboside was used to trace the production of the hormone cytokinin. The hormone was fed to soybean explants and transported via the transpiration stream. This biological marker allowed for the clear observation of transport from the xylem to the leaf and embryo of the explant. This experiment also resulted in leaves retaining their green color longer, which is important in experimentation with soybean explants (Noodén et al., *Journal of Plant Growth Regulation* 2:265-279 (1984), which is incorporated herein by reference in its entirety). A previous study by Quebedeaux and Chollet (Quebedeaux et al., *Plant Physiology* 55:745-748 (1975), which is hereby incorporated by reference in its entirety) used radioactive tracers to demonstrate that the pods (and seeds contained therein) of soybeans are the main sinks for the photosynthetic assimilates from the leaf, indicating that the decrease in the production of photosynthate is therefore due to the decrease in photosynthetic activity of the plant, which accompanies senescence (Benner et al., *Biochemie und Physiologie der Pflanzen* 179: 269-275 (1984), which is incorporated herein by reference in its entirety). In addition to these methods, translocation patterns can also be observed through analysis of products formed following exogenous feeding of large quantities of the compound(s) of interest.

It is known that myo-inositol is biosynthesized in soybean embryos. Johnson and Wang (Johnson et al., *J. Biol. Chem.* 271:17215-17218 (1996), which is hereby incorporated by reference in its entirety) demonstrated that 1L-myo-inositol 1-phosphate synthase (also known as 1D-myo-inositol 3-phosphate synthase, MIPS) catalyzes the transformation of Glc-6-P to 1L-myo-inositol 1-phosphate in embryos of developing legume seeds. However, it remains unknown whether D-pinitol or D-chiro-inositol are biosynthesized in the embryo. In order to understand the function of cyclitols, it is necessary to first understand how they are transported and from where they are transported. Therefore, one objective of this Example was to determine which cyclitols are biosynthesized in soybean embryos and which are transported to the embryo from the leaves.

Several studies provide evidence in support of the hypothesis that D-pinitol and D-chiro-inositol are biosynthesized in the leaves of soybean plants. Labeling studies done by Diettrich and Brandl (Diettrich et al., *Phytochemistry* 26:1925-1926 (1987), which is hereby incorporated by reference in its entirety), for example, showed that myo-inositol goes to D-ononitol (FIG. 20, reaction d) and afterwards to D-pinitol (FIG. 20, reaction e,f), and then presumably to D-chiro-inositol (FIG. 20, reaction g) in legume leaves. Kuo (Kuo et al., *Phytochemistry* 45:29-35 (1997), which is hereby incorporated by reference in its entirety) demonstrated that the concentration of D-pinitol was highest in seed coats and lower in axis and cotyledon tissues, suggesting that D-pinitol is biosynthesized in maternal tissue and transported to soybean embryos. In addition to this, soybean and alfalfa (*Medicago sativa* L.) somatic embryos also appear to be deficient in D-pinitol and galactopinitols (Horbowicz et al., *Plant Science* 109:191-198 (1995); Obendorf et al., *Mol. Cell. Biol. Soybean* 6:40 (1996); Chanprameet al., in *Vitro Cell Developmental Biology—Plant* 34:64-68 (1998), which are incorporated herein by reference in their entirety), and total D-pinitol or total D-chiro-inositol in soybean zygotic embryos matured in vitro did not exceed that present in embryos before culture (Obendorf et al., *Plant Science* 132:1-12 (1998); Obendorf et al., *Crop Science* 38:78-84 (1998), which are incorporated herein by reference in their entirety), indicating a lack of D-pinitol and D-chiro-inositol biosynthesis by embryo tissues. myo-inositol 6-O-methyltransferase (mI6OMT or IMT, S-adenosyl-L-methionine:myo-inositol O-methyltransferase, EC 2.1.1.129) that forms D-ononitol, is located in leaves and stems (Wanek et al., *Physiologia Plantarum* 101:416-424 (1997); Streeter et al., *Plant, Cell and Environment* 24:429-

438 (2001), which are incorporated herein by reference in their entirety). Soybean somatic embryos transformed with a gene for this enzyme form D-ononitol but not D-pinitol indicating that soybean somatic embryos do not express the enzymes that form D-pinitol. Soybean leaves accumulate mostly D-pinitol with small amounts of D-chiro-inositol, myo-inositol and D-ononitol (Streeter, *Crop Sci.* 41:1985-1987 (2001), which is hereby incorporated by reference in its entirety). Using this background information in conjunction with the knowledge that D-pinitol is a proposed precursor to D-chiro-inositol, it was hypothesized that though myo-inositol is biosynthesized in soybean embryos, D-chiro-inositol and D-pinitol are biosynthesized in the leaves and afterwards transported to the seeds. If this hypothesis is correct, then increasing the concentration of D-pinitol and D-chiro-inositol in soybean explants via exogenous feeding should result in a dramatic increase in the accumulation of fagopyritol B1 and galactopinitols in the embryo. However, if D-pinitol and D-chiro-inositol are biosynthesized in the embryo, then exogenous feeding of free cyclitols should have a less pronounced effect on galactosyl cyclitol concentrations in the seed.

Materials and Methods

Soybean plants [*Glycine max* (L.) Merrill cv. Chippewa 64] were grown in a greenhouse at 27° C. days (14 hours) and 22° C. nights (10 hours) with natural light supplemented by 640-$\mu$mol m$^{-2}$ s$^{-1}$ artificial light from Sylvania 1000-watt metal halide lamps.

Plants were excised above the third node from the bottom and below the third node from the top before leaf senescence was evident as was done by Neumann et al. *Plant Physiology* 72:182-185 (1983), which is hereby incorporated by reference in its entirety. Explants were cut mid podfill (about 35 days after flowering), when the pods were still green and approximately 7.2 mm in width, and the seeds weighed about 250 mg fresh weight. Pod number was reduced to one, containing three seeds. Each explant included one node, one leaf, one pod, and one internode. The cut basal end of the internode (stem) of the explants was placed in 50 mM solutions of cyclitols: 50 mM myo-inositol, 50 mM D-pinitol, 50 mM D-chiro-inositol, and a control without cyclitols, all in 1% sucrose by weight, and all containing 10 mM asparagine and kinetin, a cytokinin. These solutions were loaded into the explant through the cut stem and transported to the leaf by the transpiration stream and to the embryo through the phloem. A fourth solution consisting of 10 mM asparagine and kinetin in 1% sucrose (by weight) served as the control. Solutions were fed to explants for one week, and explants were allowed to dry, after which seeds were moved to the desiccators and fully dried (to 6% moisture) during a period of 14 days at 12% relative humidity over a saturated solution of LiCl.

After the seeds had slow dried, extraction and analysis of soluble carbohydrates was performed. Cotyledon and axis tissues were separated, weighed, pulverized in liquid nitrogen with a mortar and pestle, and homogenized in a ground glass homogenizer with 2.2 ml of ethanol:water (1:1, v/v), containing 300 $\mu$g (cots) or 100 $\mu$g (axis) of phenyl $\alpha$-D-glucoside as the internal standard, heated at 80° C. for 45 minutes, and centrifuged at 27,000×g for 20 minutes. Clear supernatants were passed through a 10,000 MW cutoff filter and evaporated to dryness with nitrogen gas. Residues were stored overnight in a desiccator with $P_2O_5$ to remove traces of water and afterwards derivatized with trimethylsilylimidazole:pyridine (1:1, v/v). Analysis of soluble carbohydrates was done using a Hewlett Packard 5890 Series II gas chromatograph equipped with a flame ionization detector and ChemStation software as previously described (Horbowicz et al., *Seed Science Research* 4:385-405 (1994); Obendorf et al., *Crop Science* 38:78-84 (1998), which are incorporated herein by reference in their entirety). The amounts of each soluble carbohydrate present in the samples was determined by regression equations calculated from gas chromatograms of known standards, allowing the relative amounts of cyclitols present in the leaf and embryo as a result of the feeding of excess cyclitols to be determined. Soluble carbohydrate composition is reported as mean±SE of the mean on a dry weight basis for six replicate samples of cotyledons from mature seeds.

Results

Overall, none of the feeding experiments resulted in large changes in sucrose, raffinose, or stachyose except for some low values observed in explants fed with D-chiro-inositol. Results for the experiments were consistent with the results and interpretations of feeding experiments where cyclitols were fed to immature soybean embryos (Odorcic et al., *The Biology of Seeds: Recent Research Advances*. Wallingford, UK, CABI Publishing (2003), which is incorporated herein by reference in its entirety).

myo-inositol

Feeding 50 mM myo-inositol to soybean explants slightly increased free myo-inositol and caused a 50% increase in galactinol in axis and cotyledon tissue (Tables 1 and 2).

TABLE 1

Concentration of soluble carbohydrates in cotyledons of mature soybean seeds after feeding explants 50 mM myo-inositol, D-chiro-inositol, or D-pinitol.

| | A myo-Inositol | B D-chiro-Inositol | C D-Pinitol | D Control |
|---|---|---|---|---|
| D-Pinitol | 7.77 ± 0.92 | 6.00 ± 0.52 | 35.77 ± 2.50 | 8.34 ± 1.12 |
| Galactopinitol A | 2.01 ± 0.16 | 1.89 ± 0.14 | 5.81 ± 0.38 | 1.59 ± 0.15 |
| Galactopinitol B | 1.76 ± 0.21 | 1.62 ± 0.18 | 4.88 ± 3.10 | 1.60 ± 0.22 |
| Ciceritol | 0.63 ± 0.08 | 0.34 ± 0.11 | 1.13 ± 0.16 | 0.85 ± 0.07 |
| D-chiro-Inositol | 5.15 ± 0.77 | 15.59 ± 2.08 | 1.63 ± 0.11 | 1.63 ± 0.26 |
| Fagopyritol B1 | 1.78 ± 0.23 | 21.11 ± 2.06 | 1.77 ± 0.11 | 1.05 ± 0.08 |
| Fagopyritol B2 | 0.25 ± 0.07 | 1.52 ± 0.47 | 0.16 ± 0.02 | 0.15 ± 0.04 |
| Myo-Inositol | 2.35 ± 0.79 | 0.58 ± 0.05 | 0.67 ± 0.07 | 1.69 ± 0.44 |
| Galactinol | 0.35 ± 0.06 | 0.23 ± 0.05 | 0.05 ± 0.01 | 0.25 ± 0.04 |
| Sucrose | 37.73 ± 4.81 | 27.88 ± 4.09 | 32.49 ± 2.05 | 48.76 ± 7.62 |
| Raffinose | 11.22 ± 1.12 | 7.18 ± 0.58 | 9.73 ± 0.46 | 11.00 ± 1.47 |
| Stachyose | 23.10 ± 1.94 | 12.63 ± 1.40 | 14.60 ± 1.06 | 24.51 ± 3.73 |

TABLE 2

Concentration of soluble carbohydrates in axis of mature soybean seeds after feeding explants 50 mM myo-inositol, D-chiro-inositol, or D-pinitol.

| | A myo-Inositol | B D-chiro-Inositol | C D-Pinitol | D Control |
|---|---|---|---|---|
| D-Pinitol | 3.65 ± 0.03 | 4.07 ± 0.38 | 21.40 ± 2.41 | 4.51 ± 0.58 |
| Galactopinitol A | 4.61 ± 0.41 | 4.96 ± 0.30 | 12.14 ± 1.06 | 3.65 ± 0.35 |
| Galactopinitol B | 3.17 ± 0.40 | 3.61 ± 0.30 | 9.42 ± 0.88 | 2.84 ± 0.42 |
| Ciceritol | 0.65 ± 0.12 | 0.37 ± 0.15 | 1.58 ± 0.26 | 0.79 ± 0.23 |
| D-chiro-Inositol | 1.08 ± 0.14 | 12.31 ± 1.44 | 1.28 ± 0.30 | 0.61 ± 0.12 |
| Fagopyritol B1 | 2.81 ± 0.28 | 30.95 ± 2.46 | 2.99 ± 0.22 | 1.79 ± 0.22 |
| Fagopyritol B2 | 0.24 ± 0.09 | 1.62 ± 0.50 | 0.08 ± 0.02 | 0.14 ± 0.06 |
| Myo-Inositol | 1.52 ± 0.15 | 1.37 ± 0.13 | 0.98 ± 0.13 | 1.19 ± 0.20 |
| Galactinol | 0.89 ± 0.10 | 1.00 ± 0.07 | 0.58 ± 0.08 | 0.69 ± 0.08 |

TABLE 2-continued

Concentration of soluble carbohydrates in axis of mature soybean seeds after feeding explants 50 mM myo-inositol, D-chiro-inositol, or D-pinitol.

| | A myo-Inositol | B D-chiro-Inositol | C D-Pinitol | D Control |
|---|---|---|---|---|
| Sucrose | 34.02 ± 3.52 | 32.18 ± 4.31 | 30.86 ± 4.11 | 35.59 ± 5.63 |
| Raffinose | 8.87 ± 0.77 | 6.61 ± 0.81 | 9.81 ± 1.08 | 1.030 ± 0.76 |
| Stachyose | 24.56 ± 2.55 | 17.95 ± 1.79 | 23.16 ± 2.50 | 22.02 ± 2.32 |

No significant changes in the amount of stachyose, raffinose, D-pinitol, or galactopinitols were observed. A 3.15-fold increase in free D-chiro-inositol was also observed in cotyledons and D-chiro-inositol concentrations were doubled in axis tissue. Still, there was no significant increase in concentrations of fagopyritol B1.

D-chiro-inositol

Feeding 50 mM D-chiro-inositol to soybean explants caused a 9.6-fold increase in free D-chiro-inositol, a 20-fold increase in fagopyritol B1, and a 10-fold increase in fagopyritol B2 in cotyledon tissues (Table 1). Free myo-inositol decreased but galactinol in cotyledons remained unchanged. Feeding D-chiro-inositol to soybean explants also resulted in a 20-fold increase in free D-chiro-inositol in axis tissues (Table 2). This corresponded with a 17-fold increase in fagopyritol B1 and an 11-fold increase in fagopyritol B2. All of the D-chiro-inositol fed explants had shriveled seeds, while those explants that were fed myo-inositol, D-pinitol, or the control treatment, had full and round seeds.

D-pinitol

Feeding D-pinitol quadrupled free D-pinitol and tripled galactopinitols in both axis and cotyledon tissues (Tables 1 and 2). Ciceritol concentrations increased 30% in cotyledon tissue and they doubled in axis tissue. myo-Inositol and galactinol were decreased 25%, and free D-chiro-inositol concentrations in axes doubled.

Discussion

Relative amounts of soluble carbohydrates observed can be attributed to biochemical pathways in soybean and the roles that D-pinitol, D-chiro-inositol, and myo-inositol play in these pathways.

Figure 21:
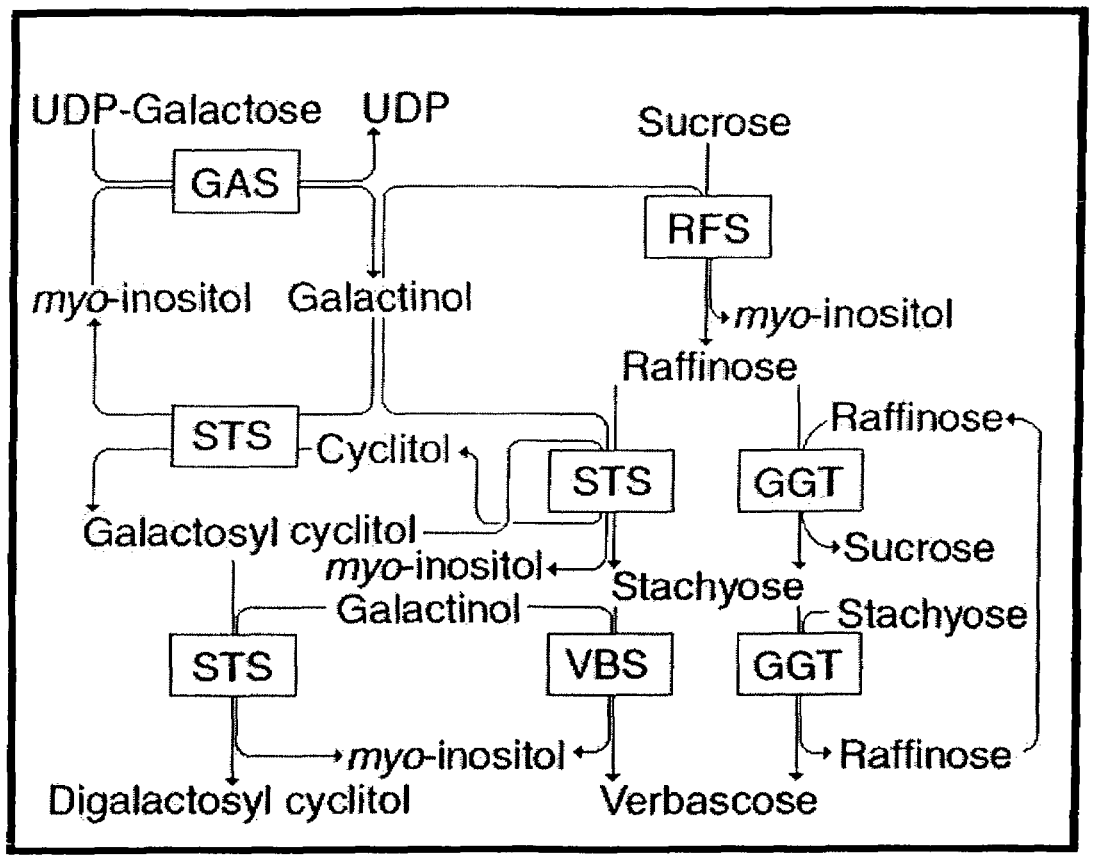
FIG. 21 shows the raffinose family oligosaccharides (RFO) and galactosyl cyclitol biosynthetic pathways. GAS (or GolS), galactinol synthase; RFS, raffinose synthase; STS, stachyose synthase; VBS, verbascose synthase; GGT, galactan:galactan galactosyltransferase. Cyclitol may stand for D-ononitol, D-pinitol, or D-chiro-inositol, respectively. All reactions are reversible (after Peterbauer et al., *Seed Sci. Res.* 11:185-198 (2001), which is hereby incorporated by reference in its entirety).

In soybean explants, galactinol synthase (GolS or GAS) produces galactinol from myo-inositol and UDP-galactose (FIG. 21). Galactinol then undergoes two reactions. In the first reaction, galactinol acts as a galactosyl donor to sucrose, which reacts with raffinose synthase (RFS) to produce raffinose and myo-inositol as a by-product. Raffinose and galactinol then reacts with stachyose synthase (STS) to produce stachyose and myo-inositol as a by-product. In the second reaction, galactinol and D-pinitol react with STS to produce galactopinitol A and galactopinitol B. Subsequent reactions with STS produce ciceritol (a digalactosyl pinitol A) from galactinol and galactopinitol A, and digalactosyl pinitol B from galactinol and galactopinitol B (FIG. 21).

Figure 20:
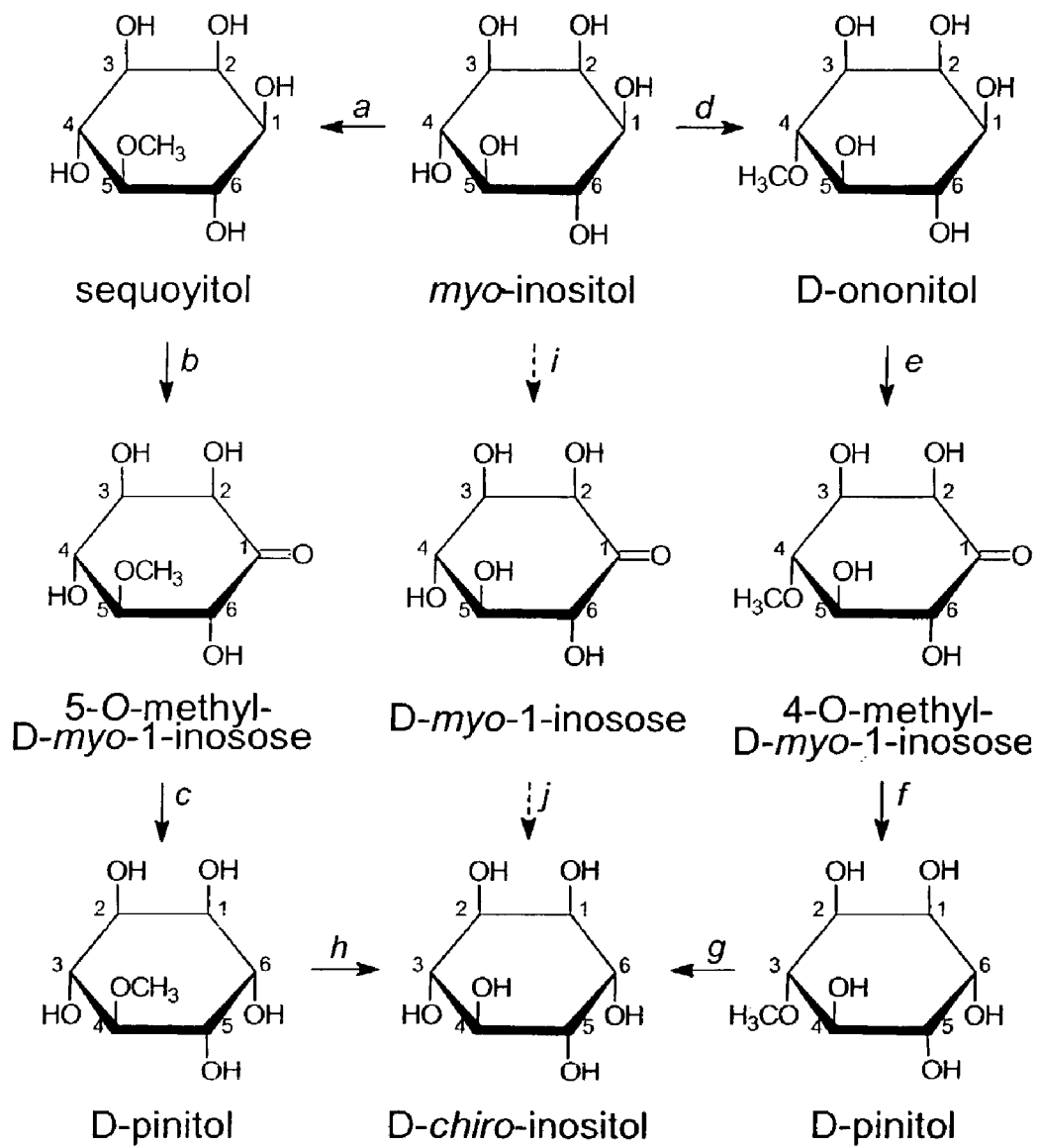
FIG. 20 shows pathways for biosynthesis of D-pinitol and D-chiro-inositol (from Obendorf, *Seed Sci. Res.* 7:63-74 (1997), which is hereby incorporated by reference in its entirety). The D-pinitol biosynthetic pathway converts myo-inositol to D-ononitol to D-pinitol in legume leaves. The illustration of D-pinitol on the bottom left is intentionally incorrectly numbered for clarity. 1L-myo-inositol 6-O-methyltransferase (EC 2.1.1.129; also known as 1D-myo-inositol 4-O-methyltransferase; reaction d) catalyzes the conversion of myo-inositol to D-ononitol. The conversion of D-ononitol to D-pinitol (e,f) may involve a two-step oxidoreductase reaction in soybean and other legumes: step 1, D-ononitol+NAD$^+$→4-O-methyl-1 D-myo-1-inosose+NADH; step 2, 4-O-methyl-1 D-myo-1-inosose+NADPH→D-pinitol+NADP$^+$. It is believed that D-chiro-inositol is formed by demethylation of D-pinitol (g,h), but neither the enzyme nor the gene have been identified. Prokaryotes, algae, insects, and animals appear to make D-chiro-inositol from myo-inositol (i,j). For details see Obendorf, *Seed Sci. Res.* 7:63-74 (1997), which is hereby incorporated by reference in its entirety. Earlier literature proposed that myo-inositol was converted to D-pinitol via sequoyitol (a,b,c) but the identity of sequoyitol is in doubt and may have been D-ononitol.

When feeding 50 mM myo-inositol, there were high levels of galactinol, the galactosyl donor for galactopinitol biosynthesis, present. The lack of increase in accumulation of galactopinitols may have been due to limited levels of D-pinitol in the explant. Biosynthesis of D-chiro-inositol in legumes is believed to be via myo-inositol to D-ononitol to D-pinitol to D-chiro-inositol (FIG. 20, reactions d,e,f,g; Dittrich et al., *Phytochemistry* 26:1925-1926 (1987) which is hereby incorporated by reference in its entirety). If the D-pinitol levels were low, it follows that D-chiro-inositol should also have been low, but this was not the case. High levels of D-chiro-inositol in the cotyledons suggest that myo-inositol, rather than D-pinitol, is a direct precursor to production of D-chiro-inositol in the leaves (FIG. 20, reactions i,j). In the absence of D-pinitol, myo-inositol goes to D-myo-1-inosose, and then to D-chiro-inositol (FIG. 20, reactions i,j). The high levels of myo-inositol present in the soybean explant following feeding with exogenous myo-inositol may limit the accumulation of raffinose and stachyose by feedback inhibition in the cotyledons of the seed. Since myo-inositol is produced as a byproduct, exogenous myo-inositol decreased the progress of the reaction of sucrose and galactinol by RFS, explaining why raffinose and stachyose levels stayed the same with this treatment.

Figure 22:
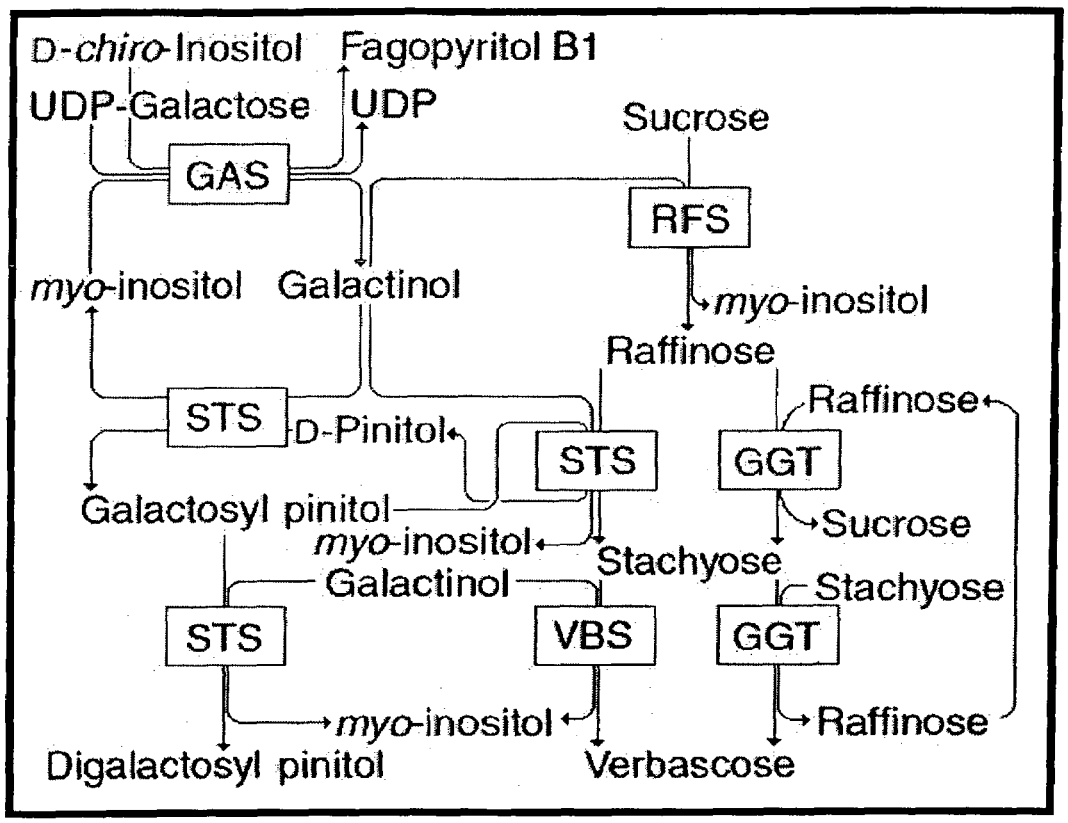
FIG. 22 shows the revised RFO and galactosyl cyclitol biosynthetic pathways. GAS (or GolS), galactinol synthase; RFS, raffinose synthase; STS, stachyose synthase; VBS, verbascose synthase; GGT, galactan:galactan galactosyltransferase. All reactions are reversible (modified from Peterbauer et al., *Seed Sci. Res.* 11:185-198 (2001), which is hereby incorporated by reference in its entirety).

Soybean galactinol synthase (GmGolS or GAS) produces fagopyritol B1 from D-chiro-inositol and UDP-galactose (FIG. 22). When feeding 50 mM D-chiro-inositol to soybean explants, a decrease in myo-inositol and D-pinitol was observed. Because myo-inositol and D-pinitol are precursors to D-chiro-inositol (FIG. 20, reactions d,e,f,g; Dittrich et al., *Phytochemistry* 26:1925-1926 (1987), which is hereby incorporated by reference in its entirety), they may not have been needed to produce D-chiro-inositol because it was fed to the explant in excess. The reason for decreased production of raffinose and stachyose is unknown. Decreases in galactosyl and digalactosyl pinitols are due to decreases in their precursor, D-pinitol. Increased levels of D-chiro-inositol caused fagopyritol B1 and fagopyritol B2 to increase as expected.

In this experiment, feeding D-pinitol increased levels of free D-pinitol in the seed. This increase served to increase the amount of galactosyl pinitols and, after reaction with STS, production of digalactosyl pinitol B. High levels of D-pinitol may have also temporarily increased D-chiro-inositol levels (FIG. 20, reaction g), which subsequently went towards increasing fagopyritol B1 production. The increased level of digalactosyl myo-inositol accounts for the decreased levels of galactinol and myo-inositol.

myo-Inositol is biosynthesized in embryo tissues of developing legume seeds (Johnson et al., *Journal of Biological Chemistry* 271, 17215-17218 (1996); Hegeman et al., *Plant Physiology* 125:1941-1948 (2001); Hitz et al., *Plant Physiology* 128:650-660 (2002), which are incorporated by reference in their entirety). D-Pinitol is biosynthesized in leaves from myo-inositol through D-ononitol as precursor (FIG. 20, reactions d,e,f; Dittrich et al., *Phytochemistry*, 26:1925-1926 (1987), which is hereby incorporated by reference in its entirety) and D-chiro-inositol is believed to be biosynthesized by demethylation of D-pinitol (FIG. 20, reaction g; see review by Obendorf, *Seed Sci. Res.* 7:63-74 (1997), which is hereby incorporated by reference in its entirety). It is not known if D-pinitol and D-chiro-inositol are biosynthesized in cotyledons of seeds. Further, the enzymes and genes responsible for the biosynthesis of D-pinitol (FIG. 20, reactions e,f) and D-chiro-inositol (FIG. 20, reaction g or FIG. 20, reactions i,j) are unknown (Obendorf, *Seed Science Research* 7:63-74 (1997), which is hereby incorporated by reference in its entirety). The results herein are consistent with the interpretation that both of D-pinitol and D-chiro-inositol are biosynthesized in leaves and transported to seeds. Of special interest is the evidence presented herein that D-chiro-inositol may be biosynthesized directly from myo-inositol, either instead of or in addition to demethylation of D-pinitol.

The results in this Example are consistent with the following interpretations: myo-inositol is formed in maternal tissues and in embryos of seeds, D-pinitol and D-chiro-inositol are biosynthesized in maternal tissues (leaves) and transported to seeds, D-chiro-inositol may be biosynthesized directly from myo-inositol, galactinol synthase utilizes D-chiro-inositol to form fagopyritol B1, stachyose synthase utilizes D-pinitol to form galactopinitols, and feeding free cyclitols to soybean explants does not increase raffinose and stachyose accumulation in cotyledons of soybean seeds.

Example 5

Soybean Explant Feeding Experiments

Soybean explants, consisting of a stem segment with attached leaf and pod, were cultured as the soybean explants described in Example 4. In this example, the soybean explant system was used to study the timing of transport of cyclitols, fed through the stem, to the developing soybean seed and the timing of their incorporation into galactosyl cyclitols in axis, cotyledons, and seed coat of developing and maturing soybean seeds. myo-inositol, D-pinitol and D-chiro-inositol were fed to soybean explants as described in Example 4, except that 50 mM cyclitol in 1% sucrose solution was fed to stems of soybean explants for three days followed by slow drying. Soluble carbohydrates were extracted and assayed by high resolution gas chromatography after slow drying of seeds (as described in Example 4).

TABLE 3

Accumulation of soluble carbohydrates in soybean axis (μg/axis) after 3 days transport of sucrose (1% solution) and myo-inositol (50 mM) into the stem of soybean explants and after slow drying of seeds for 2, 4, or 14 days (micrograms/1 axis)

| Soluble Carbohydrate | Before slow drying | | After 2 days slow drying | | After 4 days slow drying | | After 14 days slow drying | |
|---|---|---|---|---|---|---|---|---|
| | Rep 1 | Rep 2 | Rep 1 | Rep 2 | Rep 1 | Rep 2 | Rep 1 | Rep 2 |
| D-Pinitol | 5.89 | 5.97 | 5.05 | 5.72 | 2.74 | 2.86 | 6.70 | 5.72 |
| Unknown | 0.91 | 0.67 | 0.57 | 0.49 | 0.52 | 0.38 | 1.25 | 1.46 |
| D-chiro-Inositol | 1.98 | 2.17 | 3.65 | 4.69 | 3.40 | 1.75 | 9.39 | 5.12 |
| myo-Inositol | 37.08 | 37.50 | 3.34 | 1.96 | 1.74 | 1.69 | 4.22 | 3.84 |
| Sucrose | 143.88 | 139.88 | 38.38 | 76.58 | 50.48 | 82.93 | 77.01 | 63.96 |
| Galactopinitol A | 4.31 | 0 | 5.86 | 8.20 | 9.93 | 11.97 | 13.99 | 10.23 |
| Galactopinitol B | 0.72 | 0 | 1.29 | 2.20 | 3.06 | 4.60 | 5.50 | 3.91 |
| Fagopyritol B1 | 0 | 0 | 3.15 | 5.91 | 6.25 | 7.43 | 11.14 | 6.13 |
| Galactinol | 3.01 | 3.59 | 12.80 | 10.83 | 7.31 | 4.07 | 6.76 | 4.14 |
| Raffinose | Tr | 0 | 5.44 | 1.83 | 6.37 | 7.57 | 14.51 | 11.98 |
| Ciceritol | Tr | 0 | 0 | 0 | 0.39 | 0.42 | 0.56 | 0.29 |
| Fagopyritol B2 | 0 | 0 | 0 | 0 | 0 | 0 | 0 | 0 |
| Stachyose | 0 | 0 | 9.92 | 6.33 | 62.18 | 55.60 | 89.46 | 57.18 |

TABLE 4

Accumulation of soluble carbohydrates in soybean axis (μg/axis) after 3 days transport of sucrose (1% solution) and D-chiro-inositol (50 mM) into the stem of soybean explants and after slow drying of seeds for 2, 4, or 14 days (micrograms/1 axis)

| Soluble Carbohydrate | Before slow drying | | After 2 days slow drying | | After 4 days slow drying | | After 14 days slow drying | |
|---|---|---|---|---|---|---|---|---|
| | Rep 1 | Rep 2 | Rep 1 | Rep 2 | Rep 1 | Rep 2 | Rep 1 | Rep 2 |
| D-Pinitol | 6.94 | 6.11 | 6.18 | 7.87 | 6.21 | 3.86 | 7.68 | 4.13 |
| Unknown | 0.47 | 0 | 0.39 | 0.46 | 0.65 | 0.42 | 0 | 0.92 |
| D-chiro-Inositol | 25.26 | 22.53 | 20.29 | 25.33 | 11.74 | 7.67 | 39.99 | 26.32 |
| myo-Inositol | 18.22 | 16.89 | 1.93 | 2.75 | 1.27 | 1.03 | 0.92 | 1.01 |
| Sucrose | 111.55 | 149.75 | 22.44 | 28.32 | 35.75 | 23.35 | 59.50 | 30.63 |
| Galactopinitol A | 0 | 0 | 6.35 | 6.24 | 13.54 | 12.18 | 15.50 | 10.18 |
| Galactopinitol B | 0 | 0 | 1.47 | 1.56 | 6.35 | 4.73 | 9.35 | 5.03 |
| Fagopyritol B1 | 2.04 | 0 | 32.08 | 25.93 | 81.94 | 73.53 | 78.96 | 55.76 |
| Galactinol | 0 | 2.71 | 6.29 | 10.19 | 3.46 | 2.25 | 4.23 | 2.27 |
| Raffinose | 0.23 | 0 | 2.57 | 3.37 | 2.61 | 3.24 | 6.68 | 5.73 |
| Ciceritol | 0 | 0 | 0 | 0 | 0 | 0.27 | 0 | 2.69 |
| Fagopyritol B2 | 0 | 0 | 0 | 0 | 0 | 1.72 | 2.07 | 0 |
| Stachyose | 0 | 0 | 11.56 | 8.94 | 49.55 | 22.07 | 47.82 | 39.47 |

TABLE 5

Accumulation of soluble carbohydrates in soybean axis (μg/axis) after 3 days transport of sucrose (1% solution) and D-pinitol (50 mM) into the stem of soybean explants and after slow drying of seeds for 2, 4, or 14 days (micrograms/1 axis)

| Soluble Carbohydrate | Before slow drying | | After 2 days slow drying | | After 4 days slow drying | | After 14 days slow drying | |
|---|---|---|---|---|---|---|---|---|
| | Rep 1 | Rep 2 | Rep 1 | Rep 2 | Rep 1 | Rep 2 | Rep 1 | Rep 2 |
| D-Pinitol | 16.89 | 18.34 | 22.93 | 20.86 | 14.00 | 20.05 | 26.07 | 56.18 |
| Unknown | 1.30 | 1.47 | 0 | 0 | 0.69 | 0.45 | 0.95 | 1.53 |
| D-chiro-Inositol | 1.30 | 2.20 | 2.40 | 1.39 | 0.59 | 0.48 | 1.83 | 1.32 |
| myo-Inositol | 13.58 | 15.43 | 1.58 | 2.01 | 1.12 | 0 | 2.22 | 3.62 |
| Sucrose | 130.10 | 160.58 | 32.16 | 37.53 | 66.76 | 27.38 | 48.95 | 56.62 |
| Galactopinitol A | 0 | 0 | 7.62 | 9.41 | 25.04 | 19.32 | 24.72 | 32.49 |
| Galactopinitol B | 0 | 0 | 3.09 | 3.49 | 9.62 | 7.25 | 10.61 | 12.71 |
| Fagopyritol B1 | 0 | 0 | 4.30 | 2.75 | 5.79 | 4.01 | 6.41 | 8.76 |
| Galactinol | 2.27 | 2.97 | 6.40 | 10.37 | 5.46 | 2.87 | 3.92 | 4.18 |
| Raffinose | 0 | 0 | 6.33 | 3.86 | 7.49 | 3.46 | 7.60 | 11.19 |
| Ciceritol | 0 | 0 | 0 | 0.80 | 0.89 | 0.56 | 1.42 | 1.43 |
| Fagopyritol B2 | 0 | 0 | 0 | 0 | 0 | 0 | 0 | 1.26 |
| Stachyose | 0 | 0 | 11.91 | 7.69 | 79.54 | 28.64 | 54.54 | 78.56 |

TABLE 6

Accumulation of soluble carbohydrates in soybean axis (μg/axis) after 3 days transport of sucrose (1% solution) without cyclitols into the stem of soybean explants and after slow drying of seeds for 2, 4, or 14 days (micrograms/1 axis)

| Soluble Carbohydrate | Before slow drying | | After 2 days slow drying | | After 4 days slow drying | | After 14 days slow drying | |
|---|---|---|---|---|---|---|---|---|
| | Rep 1 | Rep 2 | Rep 1 | Rep 2 | Rep 1 | Rep 2 | Rep 1 | Rep 2 |
| D-Pinitol | 10.61 | 11.12 | 7.28 | 10.54 | 4.24 | 4.89 | 8.64 | 4.32 |
| Unknown | 0.32 | 0.98 | 0.85 | 0.48 | 0.69 | 0.41 | 1.58 | 1.68 |
| D-chiro-Inositol | 1.96 | 2.03 | 0.89 | 0.94 | 0.39 | 0.30 | 1.92 | 0.62 |
| myo-Inositol | 16.11 | 20.11 | 2.42 | 2.14 | 1.49 | 1.66 | 2.62 | 2.36 |
| Sucrose | 230.72 | 282.09 | 48.81 | 84.07 | 87.13 | 159.22 | 115.27 | 91.58 |
| Galactopinitol A | 0 | 0 | 7.55 | 9.97 | 17.42 | 16.07 | 16.14 | 12.28 |
| Galactopinitol B | 0 | 0 | 1.81 | 2.60 | 7.11 | 7.06 | 7.78 | 5.09 |
| Fagopyritol B1 | 1.70 | 0 | 3.51 | 5.52 | 7.09 | 6.40 | 8.41 | 4.98 |
| Galactinol | 1.20 | 5.49 | 11.09 | 13.41 | 5.60 | 4.29 | 4.38 | 4.27 |
| Raffinose | 0.62 | 2.65 | 5.83 | 8.95 | 8.58 | 12.44 | 13.14 | 8.02 |
| Ciceritol | 0 | 0 | 0.01 | 0.07 | 0.80 | 0.71 | 0.94 | 0.63 |
| Fagopyritol B2 | 0 | 0 | 5.67 | 0 | 0 | 0 | 0 | 0 |
| Stachyose | 0 | 7.83 | 0 | 27.73 | 96.03 | 118.05 | 101.39 | 69.71 |

TABLE 7

Accumulation of soluble carbohydrates in soybean cotyledons (μg/cotyledon) after 3 days transport of sucrose (1% solution) and myo-inositol (50 mM) into the stem of soybean explants and after slow drying of seeds for 2, 4, or 14 days (micrograms/1 cot)

| Soluble Carbohydrate | Before slow drying | | After 2 days slow drying | | After 4 days slow drying | | After 14 days slow drying | |
|---|---|---|---|---|---|---|---|---|
| | Rep 1 | Rep 2 | Rep 1 | Rep 2 | Rep 1 | Rep 2 | Rep 1 | Rep 2 |
| D-Pinitol | 99.88 | 127.21 | 121.52 | 132.23 | 101.97 | 128.68 | 61.67 | 95.93 |
| Unknown | 4.53 | 8.94 | 53.99 | 63.64 | 86.25 | 85.24 | 62.60 | 111.06 |
| D-chiro-Inositol | 52.20 | 55.90 | 133.52 | 129.44 | 150.98 | 192.49 | 95.36 | 137.86 |
| myo-Inositol | 257.87 | 275.47 | 67.54 | 29.93 | 21.34 | 12.69 | 7.82 | 11.96 |
| Sucrose | 1429.70 | 1496.60 | 635.91 | 995.62 | 921.47 | 1952.20 | 717.30 | 1228.20 |
| Galactopinitol A | 9.46 | 10.00 | 12.84 | 10.98 | 28.27 | 54.91 | 34.57 | 28.69 |
| Galactopinitol B | 0 | 0 | 6.27 | 3.19 | 11.92 | 28.11 | 15.29 | 9.70 |
| Fagopyritol B1 | 0 | 0 | 7.36 | 14.06 | 29.15 | 86.71 | 50.31 | 49.29 |
| Galactinol | 0 | 0 | 85.06 | 104.07 | 57.03 | 25.34 | 14.65 | 14.10 |
| Raffinose | 0 | 0 | 29.20 | 89.65 | 122.10 | 351.33 | 165.12 | 218.44 |
| Ciceritol | 0 | 0 | 0 | 0 | 0 | 0 | 2.01 | 0 |
| Fagopyritol B2 | 0 | 0 | 0 | 0 | 0 | 0 | 1.29 | 5.27 |
| Stachyose | 0 | 0 | 0 | 50.41 | 224.95 | 774.04 | 399.25 | 323.00 |

TABLE 8

Accumulation of soluble carbohydrates in soybean cotyledon (μg/cotyledon) after 3 days transport of sucrose (1% solution) and D-chiro-inositol (50 mM) into the stem of soybean explants and after slow drying of seeds for 2, 4, or 14 days (micrograms/1 cot)

| Soluble Carbohydrate | Before slow drying | | After 2 days slow drying | | After 4 days slow drying | | After 14 days slow drying | |
|---|---|---|---|---|---|---|---|---|
| | Rep 1 | Rep 2 | Rep 1 | Rep 2 | Rep 1 | Rep 2 | Rep 1 | Rep 2 |
| D-Pinitol | 175.37 | 149.51 | 140.00 | 177.82 | 131.32 | 171.09 | 91.50 | 90.76 |
| Unknown | 49.44 | 36.70 | 65.35 | 59.28 | 74.11 | 69.17 | 39.34 | 56.75 |
| D-chiro-Inositol | 518.30 | 476.04 | 635.01 | 719.52 | 388.25 | 589.84 | 335.21 | 286.00 |
| myo-Inositol | 138.61 | 142.47 | 21.83 | 55.39 | 4.25 | 10.39 | 5.77 | 3.80 |
| Sucrose | 1978.90 | 2102.30 | 360.00 | 363.10 | 395.07 | 579.04 | 580.31 | 736.23 |
| Galactopinitol A | 15.98 | 0 | 12.41 | 16.08 | 47.20 | 42.69 | 48.41 | 47.44 |
| Galactopinitol B | 0 | 0 | 0 | 0 | 22.34 | 20.06 | 25.58 | 23.82 |
| Fagopyritol B1 | 10.55 | 0 | 45.25 | 25.67 | 711.00 | 535.23 | 612.60 | 626.65 |
| Galactinol | 14.29 | 0 | 42.99 | 42.35 | 15.89 | 32.53 | 11.02 | 9.34 |
| Raffinose | 7.28 | 10.73 | 21.08 | 15.23 | 122.16 | 124.39 | 198.46 | 211.32 |
| Ciceritol | 0 | 6.06 | 13.35 | 0 | 12.69 | 0 | 3.82 | 2.83 |
| Fagopyritol B2 | 0 | 0 | 0 | 4.57 | 12.10 | 11.12 | 23.98 | 22.70 |
| Stachyose | 0 | 0 | 44.86 | 0 | 308.62 | 277.15 | 357.02 | 349.60 |

TABLE 9

Accumulation of soluble carbohydrates in soybean cotyledon (μg/cotyledon) after 3 days transport of sucrose (1% solution) and D-pinitol (50 mM) into the stem of soybean explants and after slow drying of seeds for 2, 4, or 14 days (micrograms/1 cot)

| Soluble Carbohydrate | Before slow drying | | After 2 days slow drying | | After 4 days slow drying | | After 14 days slow drying | |
|---|---|---|---|---|---|---|---|---|
| | Rep 1 | Rep 2 | Rep 1 | Rep 2 | Rep 1 | Rep 2 | Rep 1 | Rep 2 |
| D-Pinitol | 351.23 | 497.66 | 428.40 | 431.73 | 472.26 | 438.53 | 160.89 | 303.14 |
| Unknown | 62.38 | 62.50 | 46.56 | 38.08 | 76.63 | 85.85 | 24.57 | 45.01 |
| D-chiro-Inositol | 33.59 | 27.90 | 46.09 | 46.18 | 25.69 | 68.75 | 14.91 | 32.16 |
| myo-Inositol | 116.75 | 167.27 | 20.25 | 28.65 | 2.77 | 7.67 | 4.02 | 6.03 |
| Sucrose | 1364.90 | 2193.00 | 322.30 | 431.68 | 463.59 | 849.80 | 369.28 | 614.41 |
| Galactopinitol A | 9.09 | 9.60 | 12.29 | 8.49 | 94.29 | 117.43 | 86.03 | 104.22 |
| Galactopinitol B | 0 | 0 | 0 | 1.48 | 41.39 | 50.76 | 29.37 | 40.39 |
| Fagopyritol B1 | 0 | 3.39 | 4.99 | 4.57 | 51.96 | 69.76 | 29.66 | 51.85 |
| Galactinol | 0 | 0 | 28.42 | 40.81 | 20.87 | 37.07 | 11.23 | 10.39 |
| Raffinose | 0 | 4.09 | 10.85 | 15.22 | 72.18 | 187.91 | 77.60 | 162.90 |
| Ciceritol | 0 | 0 | 0 | 2.47 | 0 | 3.32 | 4.88 | 4.85 |
| Fagopyritol B2 | 0 | 0 | 4.91 | 0 | 15.04 | 11.92 | 1.77 | 0 |
| Stachyose | 0 | 0 | 0 | 0 | 211.21 | 552.89 | 268.51 | 427.70 |

TABLE 10

Accumulation of soluble carbohydrates in soybean cotyledon (μg/cotyledon) after 3 days transport of sucrose (1% solution) without cyclitols into the stem of soybean explants and after slow drying of seeds for 2, 4, or 14 days (micrograms/1 cot)

| Soluble Carbohydrate | Before slow drying | | After 2 days slow drying | | After 4 days slow drying | | After 14 days slow drying | |
|---|---|---|---|---|---|---|---|---|
| | Rep 1 | Rep 2 | Rep 1 | Rep 2 | Rep 1 | Rep 2 | Rep 1 | Rep 2 |
| D-Pinitol | 199.64 | 176.34 | 162.30 | 222.80 | 187.65 | 166.14 | 98.90 | 153.50 |
| Unknown | 11.90 | 12.07 | 22.73 | 20.87 | 60.13 | 5840 | 14.10 | 8.01 |
| D-chiro-Inositol | 45.57 | 37.40 | 50.36 | 57.42 | 69.00 | 73.60 | 54.07 | 46.46 |
| myo-Inositol | 127.35 | 113.66 | 23.50 | 29.70 | 12.71 | 15.03 | 7.16 | 16.01 |
| Sucrose | 2188.80 | 2395.60 | 731.21 | 923.69 | 1035.10 | 2211.00 | 1281.70 | 1787.10 |
| Galactopinitol A | 9.90 | 9.21 | 9.17 | 9.30 | 114.04 | 84.24 | 102.80 | 68.60 |
| Galactopinitol B | 4.55 | 1.73 | 1.56 | 1.54 | 40.67 | 36.28 | 49.91 | 30.24 |
| Fagopyritol B1 | 1.89 | 2.10 | 4.72 | 13.12 | 72.21 | 62.04 | 83.93 | 57.10 |
| Galactinol | 1.88 | 2.16 | 83.71 | 166.27 | 52.22 | 25.06 | 28.60 | 26.57 |
| Raffinose | 4.97 | 2.41 | 34.55 | 85.98 | 200.22 | 312.69 | 273.49 | 444.34 |
| Ciceritol | 0 | 0 | 1.63 | 0 | 1.79 | 2.22 | 10.22 | 4.63 |
| Fagopyritol B2 | 0 | 0 | 2.69 | 0 | 11.94 | 2.08 | 4.52 | 4.65 |
| Stachyose | 0 | 0 | 12.20 | 18.15 | 773.51 | 516.66 | 1331.00 | 904.20 |

TABLE 11

Accumulation of soluble carbohydrates in soybean seed coats (μg/seed coat) after 3 days transport of sucrose (1% solution) and myo-inositol (50 mM) into stem of soybean explants and after slow drying of seeds for 2, 4, or 14 days (micrograms/1 seed coat)

| Soluble Carbohydrate | After 2 days slow drying | | After 4 days slow drying | | After 14 days slow drying | |
|---|---|---|---|---|---|---|
| | Rep 1 | Rep 2 | Rep 1 | Rep 2 | Rep 1 | Rep 2 |
| D-Pinitol | 11.24 | 9.35 | | 6.81 | 12.13 | 15.41 |
| D-chiro-Inositol | 15.00 | 17.15 | | 7.20 | 13.32 | 22.63 |
| myo-Inositol | 38.71 | 30.23 | | 4.83 | 6.94 | 9.10 |
| Sucrose | 21.35 | 23.43 | | 14.28 | 78.62 | 138.83 |
| Galactopinitol A | 0 | 0 | 4.87 | 6.98 | 7.08 | |
| Galactopinitol B | 0 | 0 | 1.07 | 0 | 2.22 | |
| Fagopyritol B1 | 3.04 | 1.97 | 1.90 | 5.51 | 6.47 | |
| Galactinol | 0 | 0 | 0 | 2.61 | 2.91 | |
| Raffinose | 1.58 | 0 | 0 | 7.44 | 24.24 | |
| Ciceritol | 0 | 0 | 0 | 0 | 0 | |
| Fagopyritol B2 | 0 | 0 | 0 | 0 | 0 | |
| Stachyose | 0 | 0 | 0 | 20.21 | 35.12 | |

TABLE 12

Accumulation of soluble carbohydrates in soybean seed coat (μg/seed coat) after 3 days transport of sucrose (1% solution) and D-chiro-inositol (50 mM) into the stem of soybean explants and after slow drying of seeds for 2, 4, or 14 days (micrograms/1 seed coat)

| Soluble Carbohydrate | After 2 days slow drying | | After 4 days slow drying | | After 14 days slow drying | |
|---|---|---|---|---|---|---|
| | Rep 1 | Rep 2 | Rep 1 | Rep 2 | Rep 1 | Rep 2 |
| D-Pinitol | 6.55 | 5.97 | 14.69 | 10.95 | 12.79 | 16.30 |
| D-chiro-Inositol | 193.33 | 173.15 | 169.87 | 149.60 | 87.18 | 134.18 |
| myo-Inositol | 12.32 | 11.96 | 5.53 | 5.38 | 3.76 | 4.51 |
| Sucrose | 16.60 | 17.20 | 2.65 | 2.33 | 9.81 | 59.33 |
| Galactopinitol A | 0 | 4.13 | 4.72 | 4.29 | 0 | 7.33 |
| Galactopinitol B | 0 | 0.79 | 1.76 | 0.78 | 0 | 3.14 |
| Fagopyritol B1 | 3.52 | 4.88 | 9.14 | 8.69 | 14.54 | 51.81 |
| Galactinol | 0 | 1.30 | 0 | 1.19 | 0 | 1.60 |
| Raffinose | 0 | 0 | 0.36 | 0.18 | 0 | 10.08 |
| Ciceritol | 0 | 0 | 0 | 0 | 0 | 0 |
| Fagopyritol B2 | 0 | 0 | 0 | 0 | 0 | 1.35 |
| Stachyose | 0 | 0 | 0 | 0 | 0 | 15.45 |

TABLE 13

Accumulation of soluble carbohydrates in soybean seed coat (μg/seed coat) after 3 days transport of sucrose (1% solution) and D-pinitol (50 mM) into the stem of soybean explants and after slow drying of seeds for 2, 4, or 14 days (micrograms/1 seed coat)

| Soluble Carbohydrate | After 2 days slow drying | | After 4 days slow drying | | After 14 days slow drying | |
|---|---|---|---|---|---|---|
| | Rep 1 | Rep 2 | Rep 1 | Rep 2 | Rep 1 | Rep 2 |
| D-Pinitol | 78.06 | 73.32 | 58.50 | 90.19 | 50.78 | 96.60 |
| D-chiro-Inositol | 4.66 | 4.29 | 4.05 | 5.81 | 4.52 | 8.11 |
| myo-Inositol | 10.61 | 14.11 | 2.68 | 2.62 | 4.13 | 3.58 |
| Sucrose | 15.56 | 23.40 | 2.73 | 4.47 | 33.23 | 78.92 |
| Galactopinitol A | 0 | 5.55 | 4.81 | 5.72 | 10.65 | 19.70 |
| Galactopinitol B | 0 | 3.09 | 1.44 | 2.10 | 3.57 | 6.98 |
| Fagopyritol B1 | 0 | 2.10 | 1.66 | 1.66 | 4.07 | 10.12 |
| Galactinol | 0 | 0 | 0 | 0 | 0 | 2.77 |
| Raffinose | 0 | 0 | 0 | 0.54 | 0 | 18.53 |
| Ciceritol | 0 | 0 | 0 | 0 | 0 | 0 |
| Fagopyritol B2 | 0 | 0 | 0 | 0 | 0 | 0 |
| Stachyose | 0 | 0 | 0 | 0 | 0 | 64.19 |

TABLE 14

Accumulation of soluble carbohydrates in soybean seed coats (μg/seed coat) after 3 days transport of sucrose (1% solution) without cyclitols into the stem of soybean explants and after slow drying of seeds for 2, 4, or 14 days (micrograms/1 seed coat)

| Soluble Carbohydrate | After 2 days slow drying | | After 4 days slow drying | | After 14 days slow drying | |
|---|---|---|---|---|---|---|
| | Rep 1 | Rep 2 | Rep 1 | Rep 2 | Rep 1 | Rep 2 |
| D-Pinitol | 16.22 | 12.15 | 20.16 | 19.36 | 25.66 | 16.34 |
| D-chiro-Inositol | 3.27 | 3.10 | 3.77 | 1.74 | 3.38 | 2.68 |
| myo-Inositol | 12.27 | 12.84 | 5.67 | 5.65 | 3.88 | 4.63 |
| Sucrose | 21.74 | 31.93 | 8.26 | 15.33 | 19.35 | 82.18 |
| Galactopinitol A | 0 | 4.95 | 5.54 | 8.05 | 5.79 | 6.14 |
| Galactopinitol B | 0 | 1.22 | 1.45 | 0 | 0 | 2.18 |
| Fagopyritol B1 | 3.43 | 3.27 | 1.69 | 5.41 | 2.54 | 3.44 |
| Galactinol | 0 | 0 | 1.50 | 0 | 0 | 1.66 |
| Raffinose | 3.50 | 5.06 | 1.08 | 0 | 0 | 8.44 |
| Ciceritol | 0 | 0 | 0 | 0 | 0 | 0 |
| Fagopyritol B2 | 0 | 0 | 0 | 0 | 0 | 0 |
| Stachyose | 0 | 0 | 0 | 0 | 0 | 16.46 |

TABLE 15

Accumulation of soluble carbohydrates (μg/cm$^2$) in soybean leaves (1 cm$^2$ leaf disks) at 24 hours after feeding 50 mM myo-inositol, D-chiro-inositol, or D-pinitol, each in 1% sucrose solution, or 1% sucrose solution alone to stems of soybean explants

| Soluble Carbohydrate | 24 hours after feeding 50 mM cyclitol in 1% sucrose solution to explants | | | |
|---|---|---|---|---|
| | myo-Inositol | D-chiro-Inositol | D-Pinitol | Sucrose only |
| | μg/cm$^2$ leaf area | | | |
| Fructose | 88.82 | 121.03 | 62.53 | 24.85 |
| Glucose | 50.75 | 115.12 | 69.82 | 21.14 |
| D-Pinitol | 147.24 | 124.80 | 757.97 | 133.76 |
| D-chiro-Inositol | 18.98 | 439.69 | 23.29 | 12.21 |
| myo-Inositol | 296.44 | 10.15 | 5.60 | 25.31 |
| Sucrose | 46.10 | 29.51 | 28.89 | 29.90 |
| Maltose | 9.34 | 9.85 | 4.11 | 11.59 |
| Galactopinitol A | 0 | 0 | 0 | 0 |
| Galactopinitol B | 0 | 0 | 0 | 0 |
| Fagopyritol B1 | 0 | 0 | 0 | 0 |
| Galactinol | 0 | 0 | 0 | 0 |
| Raffinose | 0 | 0 | 0 | 0 |
| Ciceritol | 0 | 0 | 0 | 0 |
| Fagopyritol B2 | 0 | 0 | 0 | 0 |
| Stachyose | 0 | 0 | 0 | 0 |

Some results and conclusions drawn from this series of experiments are as follows. Feeding myo-inositol, D-chiroinositol, or D-pinitol to soybean explants increased free myo-inositol 10 fold, free D-chiro-inositol 35 fold, or D-pinitol 5 fold, respectively, in leaf tissues at 24 hours after the start of feeding explants demonstrating the uptake of cyclitols through the stem to the leaf via the transpiration stream. Free D-chiro-inositol in leaf tissues was increased slightly after feeding myo-inositol or D-pinitol, but there was no detection of galactosyl cyclitols, raffinose, or stachyose in leaf tissues indicating the absence of accumulation of these compounds in leaves.

Feeding myo-inositol, D-chiro-inositol, or D-pinitol to soybean explants increased free myo-inositol 2 fold, free D-chiro-inositol 20 to 40 fold, or D-pinitol 2 to 4 fold, respectively, in seed coat tissues of dry seeds (14 days slow drying) demonstrating the movement of cyclitols to the seed coat, presumably via the phloem. Feeding myo-inositol increased D-chiro-inositol 5 to 10 fold and doubled raffinose and stachyose, with no increase in D-pinitol or galactopinitols in the seed coat, suggesting that myo-inositol may directly serve as precursor for biosynthesis of D-chiro-inositol or through D-pinitol as intermediate. Feeding D-chiro-inositol also increased fagopyritol B1 5 to 15 fold in seed coats, but not other cyclitols, galactosyl cyclitols, or raffinose and stachyose. Feeding D-pinitol doubled galactopinitols and increased D-chiro-inositol, fagopyritol B1, raffinose, and stachyose indicating that D-pinitol may serve as precursor to D-chiro-inositol biosynthesis and that galactopinitols may serve as a galactosyl donor for the biosynthesis of stachyose.

Feeding myo-inositol, D-chiro-inositol, or D-pinitol to soybean explants increased free myo-inositol slightly, free D-chiro-inositol 15 to 40 fold, or D-pinitol 4 to 15 fold, respectively, in axis tissues of dry seeds (14 days slow drying) demonstrating the downloading of cyclitols from the seed coat to the embryonic axis. Feeding myo-inositol had little effect on the accumulation of other soluble carbohydrates in the embryonic axis. Feeding D-chiro-inositol also increased fagopyritol B1 10 fold in seed coats, but not other cyclitols, galactosyl cyclitols, or raffinose and stachyose. Feeding D-pinitol doubled galactopinitols in the embryonic axis, but not other cyclitols, galactosyl cyclitols, or raffinose and stachyose. These results suggest that galactopinitols and fagopyritols are biosynthesized by different pathways.

Feeding myo-inositol, D-chiro-inositol, or D-pinitol to soybean explants did not increase free myo-inositol, but increased free D-chiro-inositol 5 to 6 fold, or D-pinitol 2 fold, respectively, in cotyledon tissues of dry seeds (14 days slow drying) demonstrating the downloading of cyclitols from the seed coat to the soybean embryo. Feeding myo-inositol doubled free D-chiro-inositol but had little effect (or decreased) other soluble carbohydrates consistent with myo-inositol being a precursor for the biosynthesis of D-chiro-inositol. Feeding D-chiro-inositol also increased fagopyritol B1 6 to 10 fold in cotyledons, but not other cyclitols, galactosyl cyclitols, or raffinose and stachyose, indicating that fagopyritols do not serve as galactosyl donors for stachyose biosynthesis. Feeding D-pinitol did not increase accumulation of cyclitols (other than D-pinitol), galactosyl cyclitols, raffinose, or stachyose in cotyledons.

These results are in general agreement with the those of Examples 2 and 3.

Example 6

Buckwheat Plant Temperature Experiments

Common buckwheat (*Fagopyrum esculentum* Moench) belongs to *Polygonoceae* family. Originating in northeast Asia, southern Siberia and northern China, there are 18 recognized natural species in *Fagopyrum*. Among them, common buckwheat is most important from economical, agricultural, and nutritional points of view. In buckwheat, the triangular fruit (achene) forms a single seed. The buckwheat embryo is rich in lipids (Horbowicz et al., *J. Agric. Food Chem*. 40:745-750 (1992), which is hereby incorporated by reference in its entirety), and high quality proteins (Elpidina et al., *J. Exp. Bot*. 41:969-977 (1990), which is hereby incorporated by reference in its entirety), and is embedded in a starchy endosperm (Marshall et al., *Adv. Cereal Sci. Tech*. 5:157-210 (1982); Steadman et al., *J. Cereal Sci*. 33:271-278 (2001), which are hereby incorporated by reference in their entirety).

Common buckwheat plants are dimorphic and heterostylous. One-half of the plants have pin-type flowers with long styles and short stamens, and one-half of the plants have thrum-type flowers with short styles and long stamens (Marshall et al., *Adv. Cereal Sci. Tech*. 5:157-210 (1982), which is hereby incorporated by reference in its entirety). Each type is self-incompatible and cross-incompatible among plants with the same flower type. Seed set requires legitimate cross pollination, pin by thrum and thrum by pin, by insects under field conditions or by hand pollination in the greenhouse as in the present study (Horbowicz et al., *J. Agric. Food Chem*. 40:745-750 (1992), which is hereby incorporated by reference in its entirety).

Buckwheat plants grow best in cool, moist climates. Daytime air temperatures of 17° C. to 19° C. are optimal during flowering and seed maturation of this plant (Marshall et al., *Adv. Cereal Sci. Tech*. 5:157-210 (1982), which is hereby incorporated by reference in its entirety). Because the crop matures in 10 to 12 weeks, it can be grown in temperate regions and higher altitude areas. The crop is sensitive to high temperatures and dry weather, especially when the plants are flowering (Slawinska et al., *Seed Sci. Res*. 11:223-233 (2001); Taylor et al., *Crop Sci*. 41:1792-1799 (2001), which are hereby incorporated by reference in their entirety).

Recent evidence points to the importance of special types of carbohydrates in development of seed desiccation tolerance and storability (Koster et al., *Plant Physiol*. 88:829-832 (1998); Blackman et al., *Plant Physiol*. 100:225-230 (1992); Horbowicz et al., *Seed Sci. Res*. 4:385-405 (1994); Obendorf et al., *Seed Sci. Res*. 7:63-74 (1997); Obendorf et al., *Crop Sci*. 38:78-84 (1998), which are hereby incorporated by reference in their entirety). During development of legume seeds mainly sucrose and α-galactosides of sucrose are accumulated (Horbowicz et al., *Seed Sci. Res*. 4:385-405 (1994); Obendorf et al., *Seed Sci. Res*. 7:63-74 (1997); Brenac et al., *J. Plant Physiol*. 150:481-488 (1997), which are hereby incorporated by reference in their entirety). Instead, buckwheat seeds contains sucrose and α-galactosides of D-chiro-inositol (Horbowicz et al., *Planta* 205:1-11 (1998), which is hereby incorporated by reference in its entirety).

Six fagopyritols (galactosyl cyclitols), representing two distinct series differing in bonding positions, were found in buckwheat seeds (Horbowicz et al., Planta 205:1-11 (1998); Steadman et al., *J. Cereal Sci*. 33:271-278 (2001); Steadman et al., *Carbohydr. Res*. 331:19-25 (2001); Szczecinski et al., *Bull. Pol. Acad. Sci*. 46:9-13 (1998), which are hereby incorporated by reference in their entirety). Fagopyritol B1 and fagopyritol A1 are the major galactosides accumulated, and correlated to desiccation tolerance in buckwheat seeds (Horbowicz et al., *Planta* 205:1-11 (1998); Obendorf et al., *Carbohydr. Res*. 328:623-627 (2000), which are hereby incorporated by reference in their entirety). Structures of di- and trigalactosides of D-chiro-inositol have been confirmed as well (Steadman et al., *Carbohydr. Res.* 331:19-25 (2001), which is hereby incorporated by reference in its entirety). All fagopyritols accumulate mainly in the embryo of buckwheat seeds, and much lower amounts in endosperm (Horbowicz et al., *Planta* 205:1-11 (1998), which is hereby incorporated by reference in its entirety).

chiro-inositol plays a role in the biosynthesis of galactosamine-D-chiro-inositol, an insulin mediator in type II diabetes (Lamer et al., *Biochem. Biophys. Res. Commun.* 151: 1416-1426 (1988); Romero et al., *Adv. Pharmacology* 24:21-50 (1993), which are hereby incorporated by reference in their entirety). In Type II (non-insulin dependent diabetes mellitus) diabetic patients have deficiency of an insulin mediator containing galactosamine-D-chiro-inositol phosphate (Asplin et al., *Proc. Nat. Acad. Sci.* 90:5924-5928 (1993), which is hereby incorporated by reference in its entirety). Adding D-chiro-inositol as a dietary supplement appeared to be effective in lowering symptoms of diabetes (Ortmeyer et al., *Endocrinology* 132:640-645 (1993), which is hereby incorporated by reference in its entirety). Several research groups are developing sources for natural and synthetic supplies of D-chiro-inositol (U.S. Pat. No. 5,091,596 to Kennigton et al; Mandel et al., *J. Org. Chem.* 58:2331-2333 (1993), which are hereby incorporated by reference in their entirety). One natural source of D-chiro-inositol (in free form and as galactosides) is buckwheat seed, and the bran milling fraction from buckwheat seed can be used for isolation and production of fagopyritols and free D-chiro-inositol preparations for medical purposes (Obendorf et al., *Carbohydr. Res.* 328:623-627 (2000); Steadman et al., *J. Agric. Food Chem.* 48:2843-2847 (2000); Horbowicz et al., *J. Agric. Food Chem.* 40:745-750 (1992), which are hereby incorporated by reference in their entirety).

Temperature during development of legume seeds had only minor effects on soluble carbohydrate biosynthesis and accumulation (Gorecki et al., *Crop Sci.* 36:1277-1282 (1996); Obendorf et al., *Crop Sci.* 38:78-84 (1998), which are hereby incorporated by reference in their entirety). However during our preliminary studies, temperature during seed maturation affected soluble carbohydrate content and composition of buckwheat embryos (Horbowicz et al., *Planta* 205:1-11 (1998), which is hereby incorporated by reference in its entirety). Warm temperature (25° C.) favored biosynthesis of sucrose, and embryos matured at cool temperature (18° C.) accumulated higher quantities of fagopyritol A1 and fagopyritol B1. During maturation of soybean embryos, warm temperature (25° C.) favors biosynthesis of fagopyritol B1, as well as sucrose, raffinose, D-chiro-inositol and D-pinitol (Obendorf et al., *Crop Sci.* 38:78-84 (1998), which is hereby incorporated by reference in its entirety). The objective of this Example was to determine if temperature (15, 22 and 30° C.) during buckwheat seed maturation in plants affects accumulation of soluble carbohydrates, dry and fresh mass, and germination of buckwheat embryos and seeds.

Materials and Methods

Buckwheat plants (cv. Mancan) were grown in the greenhouse at 24° C. day (14 hours) and 18° C. night (10 hours). Natural sunlight was supplemented 14 hours daily with 740 µmol $m^2 s^{-1}$ light from 1000 W Sylvania metal halide lamps. After opening first flowers, plants were separated into pin and thrum types and placed in separate growth chambers at 18° C. All plants received 14 hours of fluorescent light daily at about 300 µmol $m^2 s^{-1}$. After 7 to 10 days, plants were hand pollinated by legitimate cross-pollination, pin×thrum and thrum× pin. Eight days after pollination the temperature in three growth chambers was changed from 18° C. to 15° C., 22° C., and 30° C., respectively. Seeds were harvested at 8, 12, 16, 20, and 28 days after pollination (DAP) and analyzed for soluble carbohydrates. After the last harvest (28 DAP) seeds were placed in a desiccator over saturated LiCl solution (RH=12%), and dried for 14 days before analysis. Weight of each groat was measured. After drying over LiCl, seeds (four replications of 10 groats each) were germinated on wet germination papers at 25° C. in darkness. After 2, 4, and 6 days the germination rate (in %) was measured, as well as hypocotyl length.

Carbohydrates in buckwheat embryo were analyzed by high resolution gas chromatography as previously described (Horbowicz et al., *Seed Sci. Res.* 4:385-405 (1994); Horbowicz et al., *Planta* 205:1-11 (1998), which are incorporated herein by reference in their entirety). Carbohydrate standards (sucrose, myo-inositol, fructose, glucose, raffinose and stachyose), internal standard (phenyl α-D-glucoside), pyridine and trimethylsilylimidazole (TMSI) were purchased from Sigma. Fagopyritol standards were purified from buckwheat (Horbowicz et al., *Planta* 205:1-11 (1998); Steadman et al., *Carbohydr. Res.* 331:19-25 (2001), which are incorporated herein by reference in their entirety). Galactinol and D-chiro-inositol standards were a gift.

Results

Buckwheat embryos accumulated maximum fresh weight by 20 days after pollination (DAP) when matured at 15° C., by 16 DAP when matured at 22° C., and by 12 DAP when matured at 30° C. (Table 16).

TABLE 16

Dry weight (DW) and fresh weight (FW) of buckwheat embryos (mg/embryo) from seeds matured at 15, 22, or 30° C. as a function of days after pollination (DAP). Values are mean ± SE for three replicate samples.

| DAP | Maturation at 15° C. | | Maturation at 22° C. | | Maturation at 30° C. | |
| --- | --- | --- | --- | --- | --- | --- |
| | FW (mg) | DW (mg) | FW (mg) | DW (mg) | FW (mg) | DW (mg) |
| 8 | 0.99 ± 0.08 | 0.24 ± 0.12 | 0.99 ± 0.08 | 0.24 ± 0.07 | 0.99 ± 0.08 | 0.24 ± 0.07 |
| 12 | 3.00 ± 0.71 | 0.70 ± 0.27 | 6.77 ± 1.41 | 1.47 ± 0.14 | 11.17 ± 0.95 | 4.43 ± 0.43 |
| 16 | 11.50 ± 1.25 | 4.23 ± 1.07 | 14.13 ± 3.06 | 5.77 ± 1.62 | 10.57 ± 0.20 | 5.17 ± 0.23 |
| 20 | 17.37 ± 0.64 | 8.67 ± 0.32 | 13.43 ± 0.67 | 6.97 ± 0.61 | 9.90 ± 0.52 | 7.63 ± 0.26 |
| 28 | 14.43 ± 1.07 | 8.03 ± 0.26 | 8.60 ± 0.38 | 6.37 ± 0.13 | 6.67 ± 0.87 | 6.83 ± 0.65 |
| 28 DAP + 2 wk 12% RH | 7.80 ± 0.72 | 7.07 ± 0.64 | 7.40 ± 0.98 | 6.50 ± 0.86 | 9.73 ± 0.59 | 6.93 ± 0.54 |

Highest daily increase in fresh weight occurred between 12 and 16 DAP when matured at 15 and 22° C. and between 8 and 12 DAP when matured at 30° C.

Independently of maturation temperature, the dry weight of embryos reached maximal values after 20 DAP, but fastest daily increase of DW occurred between 8 and 12 DAP at 30° C., between 12 and 16 DAP at 22° C., and at 15° C. between 16 and 20 DAP (Table 16). Although differences in the rates of dry matter accumulation occurred between all temperatures, the final dry weight of embryos matured at 15, 22 and 30° C. was similar. The slight decrease of dry weight in embryos matured at 15° C. noted after 2 weeks of drying over LiCl solution probably was the effect of difficulty in removing all remnants of cotyledons surrounded by endosperm tissue. Equal accumulation of embryo dry weight was also noted in our previous experiments, where seeds were matured in 18 and 25° C. (Horbowicz et al., Planta 205:1-11 (1998), which is hereby incorporated by reference).

Mean dry weight of groats gradually declined when maturation temperature increased. Mean dry weight of buckwheat groats matured at 15° C. was 48.17±1.75 mg, at 22° C.- 41.27±1.48 mg, and at 30° C.- 35.20±1.31 mg. Data presented here are the groat mean (±SE) dry weights from 50 seeds. Calculated average decline of buckwheat groat weight with increasing temperature was −0.86 mg/1° C.

Maturation temperature had no effect on the total amount of soluble carbohydrates in buckwheat embryos (Table 17).

TABLE 17

Soluble carbohydrates (µg/embryo) in buckwheat embryos from seeds matured at 15, 22, or 30° C. All seed harvested at 28 days after pollination (DAP) and dried 2 weeks at 12% RH. Values are mean ± SE for three replicate samples.

| Sol. carbohydrate | Maturation at 15° C. | Maturation at 22° C. | Maturation at 30° C. |
|---|---|---|---|
| D-chiro-Inositol | 9.76 ± 2.86 | 6.81 ± 1.07 | 3.49 ± 0.66 |
| Fagopyritol A1 | 45.59 ± 5.24 | 34.15 ± 10.02 | 21.78 ± 1.55 |
| Fagopyritol B1 | 256.00 ± 38.30 | 219.15 ± 24.20 | 159.60 ± 7.70 |
| Fagopyritol A2 | 3.66 ± 0.84 | 11.12 ± 3.04 | 15.52 ± 0.68 |
| Fagopyritol B2 | 2.47 ± 0.74 | 12.98 ± 3.59 | 19.70 ± 1.74 |
| Sub total | 317.50 ± 48.00 | 284.60 ± 42.00 | 220.10 ± 12.30 |
| myo-Inositol | 2.91 ± 0.54 | 5.03 ± 0.74 | 3.25 ± 0.64 |
| Galactinol | 0 | 1.57 ± 0.79 | 1.60 ± 0.04 |
| Digalactosyl myo-inositol | 0.25 ± 0.25 | 0.55 ± 0.55 | 1.69 ± 0.73 |
| Sub total | 3.16 ± 0.79 | 7.15 ± 2.08 | 6.54 ± 1.41 |
| Sucrose | 225.00 ± 14.90 | 250.20 ± 22.70 | 376.40 ± 59.20 |
| Total soluble carbohydrates | 545.70 ± 63.70 | 542.00 ± 66.80 | 603.00 ± 72.90 |

Figure 23:
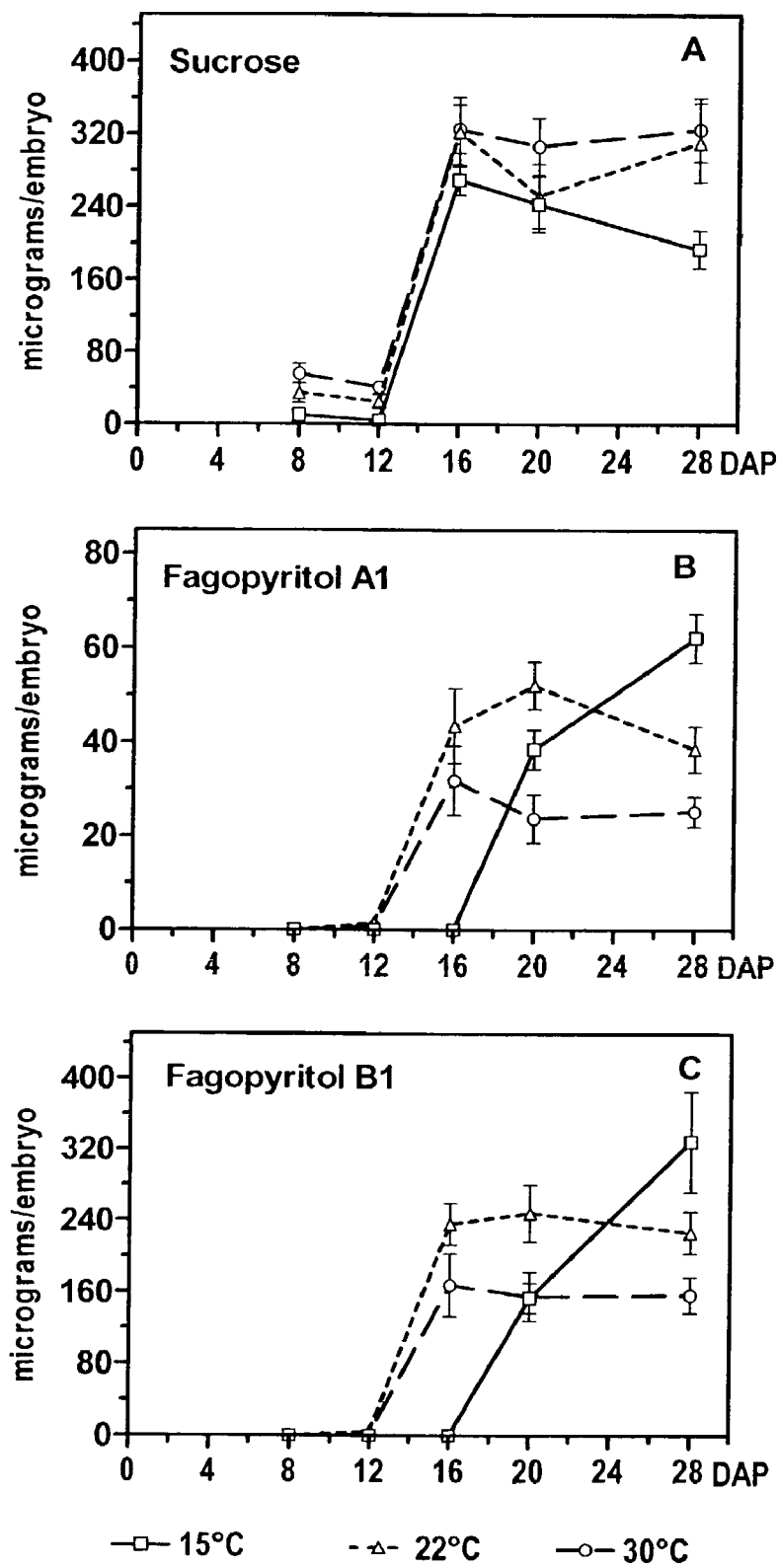
FIGS. 23A-C are graphs showing accumulation of major carbohydrates during maturation of buckwheat embryos at 15, 22, and 30° C. Values (μg/embryo) are the mean±SE of the mean for three replicate samples. DAP=days after pollination.

Reducing sugars, fructose and glucose were present only in early stages of embryo development (8 and 12 DAP). Sucrose slightly decreased between 8 and 12 DAP, probably due to temperature and pollination shocks, and then during next 4 days increased dramatically reached maximal values 16 DAP (FIG. 23A). This increase was due to a rapid increase of embryo fresh weight during maturation at 15 and 22° C., but not at 30° C. (FIG. 23A and Table 16). During maturation at 30° C., the highest daily increase of fresh weight occurred between 8 and 12 DAP, but in the same time sucrose level slightly declined. After 16 DAP sucrose level in embryos matured at 15 and 22° C. decreased, and finally after drying over LiCl solution, the embryo sucrose content was 225.0 and 250.2 µg/embryo, respectively. Maturation at 30° C. and further drying over LiCl solution of buckwheat embryos did not change the level of sucrose, which remained much higher at 376.4 µg (Table 17).

Monogalactosides of D-chiro-inositol (isomers fagopyritol A1 and fagopyritol B1) were the dominant soluble carbohydrates in embryos of buckwheat seeds matured in 15° C., but not when matured at 22 or 30° C. (FIGS. 23B and C). After drying of harvested buckwheat seeds at 12% relative humidity (RH) over LiCl solution, the ratio of fagopyritol B1 to sucrose was 1.14:1 when embryos were matured at 15° C., 0.88:1 in embryos matured at 22° C., and only 0.43:1 in embryos matured at 30° C. (Table 17). A similar situation, a clear decline of sucrose in relation to increased temperature, occurred in the case of positional isomer fagopyritol A1, although level of fagopyritol B1 was 5 to 7 times higher than fagopyritol A1 (FIGS. 23B and C and Table 17).

Figure 24:
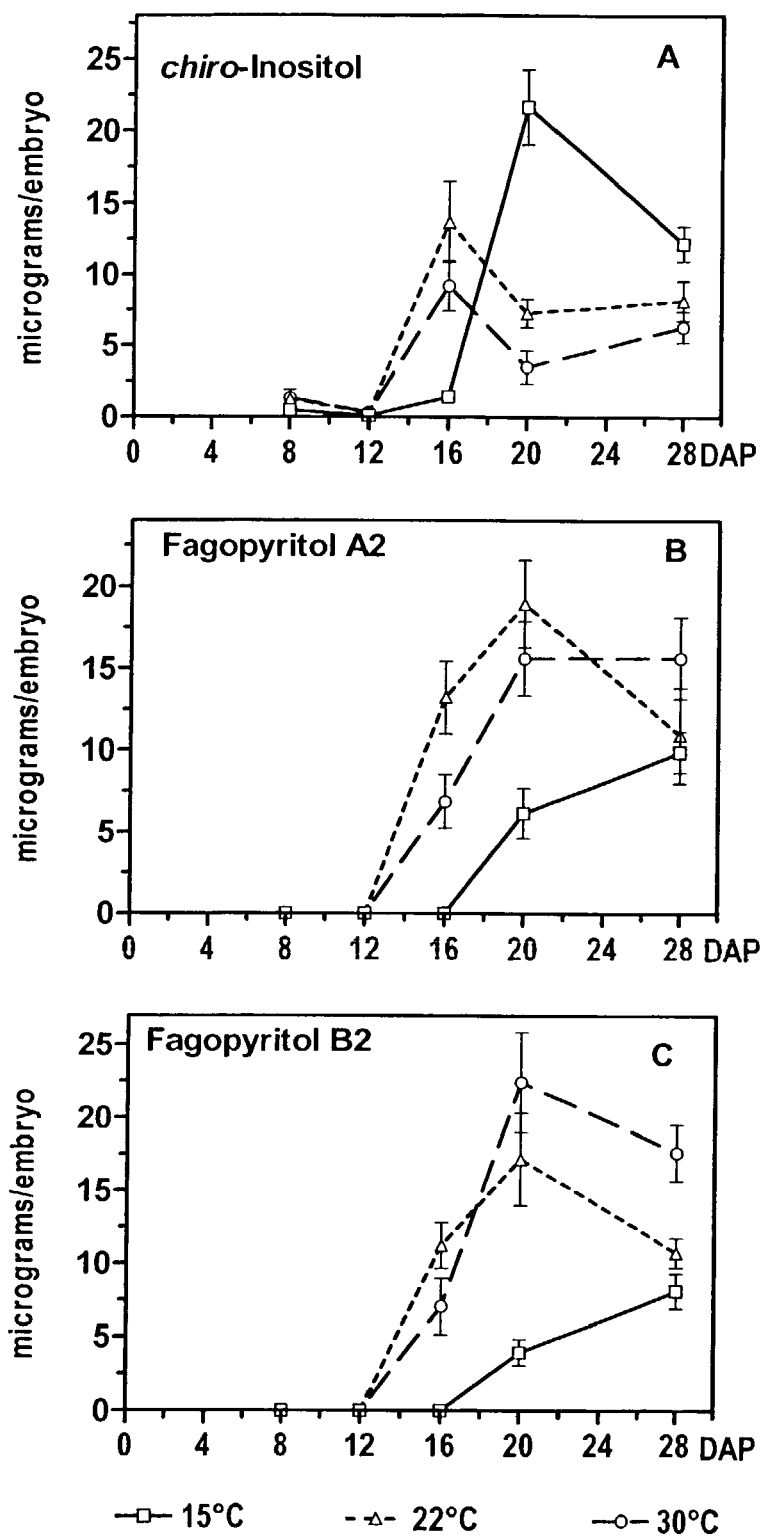
FIGS. 24A-C are graphs showing the accumulation of D-chiro-inositol and its digalactosides, fagopyritol A2 and fagopyritol B2, during maturation of buckwheat embryos at 15, 22, and 30° C. Values (μg/embryo) are the mean±SE of the mean for three replicate samples. DAP=days after pollination.
Figure 25:
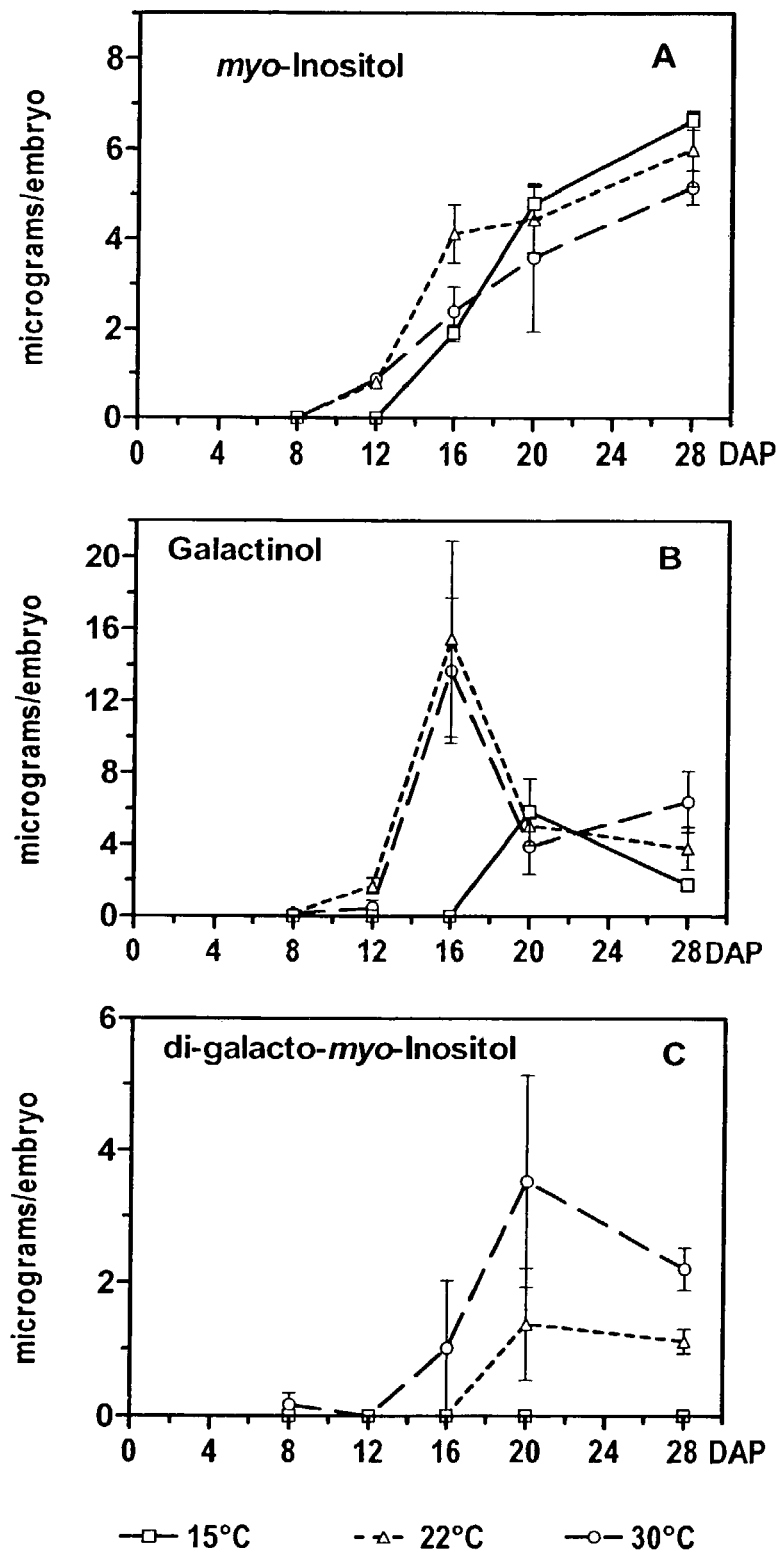
FIGS. 25A-C are graphs showing the accumulation of myo-inositol and its galactosides, galactinol and digalactosyl myo-inositol, during maturation of buckwheat embryos at 15, 22, and 30° C. Values (μg/embryo) are the mean±SE of the mean for three replicate samples. DAP=days after pollination.

An opposite situation occurred in the case of D-chiro-inositol digalactosides, fagopyritol A2 and fagopyritol B2 (FIGS. 24A-C); higher amounts accumulated in embryos matured at higher temperatures (22 and 30° C.) than at 15° C. After 2 weeks of drying of buckwheat seeds, embryos of seeds matured at 30° C. contained about 4 times more fagopyritol A2, and almost 8 times more fagopyritol B2 than embryos of seeds matured at 15° C. (Table 17). Similar effect of maturation temperature was found in case galactosides of myo-inositol (FIGS. 25A-C). Accumulation of myo-inositol in embryo was similar at all temperatures of buckwheat seed maturation, however the amount of its galactosides (galactinol and digalactosyl myo-inositol (DGMI)) was much less in embryos of seeds matured at 15° C. than in embryos of seeds matured at 22° C. and especially in seeds matured at 30° C. (Table 18).

TABLE 18

Minor soluble carbohydrates (µg/embryo) in buckwheat embryos from seeds matured at 15, 22, or 30° C. as a function of days after pollination (DAP). Values are mean ± SE for three replicate samples.

| Soluble Carbohydrate | Maturation temperature | 16 DAP | 20 DAP | 28 DAP | 28 DAP + 2 wk 12% RH |
|---|---|---|---|---|---|
| Digalactosyl myo-inositol | 15° C. | 0 | 0 | 0 | 0.25 ± 0.25 |
|  | 22° C. | 0 | 1.38 ± 0.84 | 1.12 ± 0.18 | 0.55 ± 0.55 |
|  | 30° C. | 1.02 ± 1.02 | 3.54 ± 2.51 | 2.21 ± 0.32 | 1.69 ± 0.73 |
| Fagopyritol A3 | 15° C. | 0 | 0 | 0 | 0 |
|  | 22° C. |  | 0 | 0 |  |
|  | 30° C. |  | 9.80 ± 5.47 | 4.41 ± 4.41 |  |

TABLE 18-continued

Minor soluble carbohydrates (µg/embryo) in buckwheat embryos
from seeds matured at 15, 22, or 30° C. as a function of days after
pollination (DAP). Values are mean ± SE for three replicate samples.

| Soluble Carbohydrate | Maturation temperature | 16 DAP | 20 DAP | 28 DAP | 28 DAP + 2 wk 12% RH |
|---|---|---|---|---|---|
| Raffinose | 15° C. | 0 | 0 | 0 | 0 |
| | 22° C. | | 0 | 0.78 ± 0.45 | |
| | 30° C. | | 0.70 ± 0.12 | 1.21 ± 0.95 | |
| Stachyose | 15° C. | 0 | 0 | 0 | 0 |
| | 22° C. | | 0 | 3.04 ± 3.04 | |
| | 30° C. | | 2.71 ± 2.71 | 5.07 ± 2.53 | |

During later stages of buckwheat embryo development (after 20 DAP and 28 DAP) at 22 and 30° C., small amounts of raffinose and stachyose were found (Table 18). In embryos matured in 30° C., fagopyritol A3 (a trigalactoside of D-chiro-inositol) was present as well. Embryos matured in 15° C. did not contain these carbohydrates in measurable quantities (Table 18). After 2 weeks dehydration of buckwheat seeds, analyzed embryo raffinose, stachyose, and fagopyritol A3 declined to levels below the limit of detection.

Figure 26:
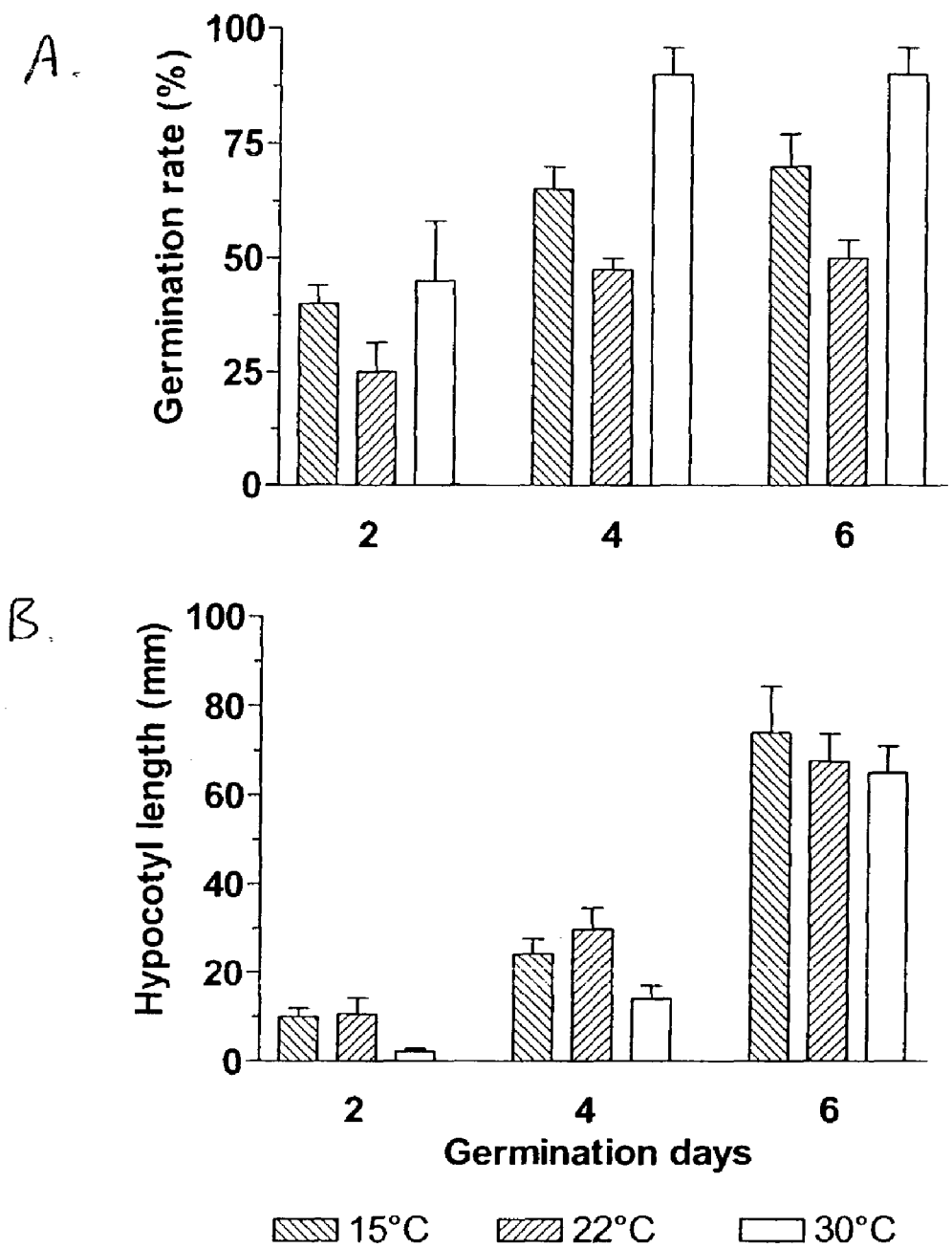
FIGS. 26A-B are graphs showing seed germination rate (%) and seedling hypocotyls length (mm) of buckwheat seeds matured at 15, 22, and 30° C. Values are the mean±SE of the mean for three replicate samples.

The germination rate of seeds matured in low temperatures (15 or 22° C.) was lower than for seeds matured at 30° C. (FIG. 26A). Differences were quite clear after 4 and 6 days of germination on moist germination paper in darkness and 25° C. Germination rate of seeds matured in 22° C. was 14, 18, and 20% lower after 2, 4, and 6 days respectively, than for seeds matured at 15° C. When compared to seeds matured at 30° C., the germination rate of seeds matured in 22° C. was 20%, 44%, and 41% lower. Germination rate of seeds matured in 30° C. was similar to those matured in 15° C. after 2 days of germination, however after 4 and 6 days, seeds matured at 30° C. germinated 90%, and seeds matured at 15° C. germinated only 66% and 71% (FIG. 26A).

Growth of hypocotyls in germinating buckwheat seeds was faster in seeds matured at 15 and 22° C., than for seeds matured at 30° C. (FIG. 26B). Such a situation occurred after 2 and 4 days of germination process, but after 6 days the differences in hypocotyl length were not significant.

Discussion

The response of plants to stress involves complex physiological and biochemical responses. Conditions during seed development and maturation can have an impact on subsequent seed quality. Soil moisture and temperature stress in that time has been suggested to have an influence on seed and seedling vigor. Factors during seed maturation such as environmental conditions also have an impact on seed viability (Baskin et al., *Seeds: Ecology, Biogeography, and Evolution of Dormancy and Germination*, Academic Press, New York, pp. 41-43 (1998), which is hereby incorporated by reference in its entirety). High temperatures during growth can increase biochemical reactions in plants, but it might not always be transferred to higher productivity because of heat stress constraints such as limited water supply, increase in leaf temperature, increased respiration, decline of the synthesis and/or activity of photosynthetic enzymes. In buckwheat groats matured in high temperatures (22 or 30° C.), reduced mean weight was noted, than when produced in low temperature (15° C.). Although high temperature maturation (30° C.) can change physiological reactions the buckwheat embryos obtained in such conditions have similar dry weight to those from matured in lower temperatures (15 or 22° C.). Dry weight of whole seed was lower, mainly due to decrease of endosperm deposition (Horbowicz et al., *Planta* 205:1-11 (1998), which is hereby incorporated by reference in its entirety). Additionally, plants growing at 25° C. produced only half as many seeds as plants at 18° C. (Slawinska et al., *Seed Sci. Res.* 11:223-233 (2001), which is hereby incorporated by reference in its entirety). All mentioned facts can have huge impact on buckwheat seed yield. Probably, the difference in temperature during buckwheat flowering and seed filling is the main factor influencing the large variability in seed set and seed yield among years (Slawinska et al., *Seed Sci. Res.* 11:223-233 (2001); Taylor et al., *Crop Sci.* 41:1792-1799 (2001), which is hereby incorporated by reference in its entirety).

During high temperature stressed plants make a special proteins called heat shock proteins (HSPs). Among the different HSPs produced by plants, the small (sm) HSPs appear to be particularly important because of their abundance. In addition, smHSPs are expressed during specific stages of plant development including seed maturation, indicating they also function in the absence of stress to protect components essential for seed development (Schoffl et al., *Plant Physiol.* 117:1135-1141 (1998), which is hereby incorporated by reference in its entirety). HSPs showing a reversible interaction with other proteins and preventing either complete denaturation or supporting proper folding of enzymes under or after protein denaturing conditions. Some HSP-like proteins are involved in the processes of targeting other proteins to organelles or to their suborganellar localization and a number of HSPs are expressed in the absence of external stressors, during embryogenesis and seed maturation in many plant species (Schoffl et al., *Acta Physiol. Plantarum* 19:549-556 (1997), which is hereby incorporated by reference in its entirety).

It is possible that HSPs might have an influence on biosynthesis of carbohydrates during maturation of buckwheat embryos. In buckwheat embryos matured in higher temperatures biosynthesis of fagopyritols B1 and its positional isomer fagopyritol A1 was partly inhibited (Horbowicz et al., *Planta* 205:1-11 (1998), which is hereby incorporated by reference in its entirety). In present studies total amounts of both fagopyritols in embryos matured at 15° C. is about twice as high as those matured at 30° C. However, sucrose level is much higher in buckwheat embryos matured at high temperatures. This observation differs from soybean embryos, where maturation at 25° C. enhanced the amount of fagopyritol B1 when compared to embryos matured at 18° C. (Obendorf et al., *Crop Sci.* 38:78-84 (1998), which is hereby incorporated by reference in its entirety).

D-chiro-inositol and its galactosides (fagopyritols) have potential medical importance in lowering symptoms of non-insulin dependent diabetes mellitus (Asplin et al., *PNAS USA*

90:5924-5928 (1993); Lamer et al., *Biochem. Biophys. Res. Commun.* 151:1416-1426 (1988); Ortmeyer et al., *Endocrinology* 132:640-645 (1993); Romero et al., *Adv. Pharmacology* 24:21-50 (1993), which are hereby incorporated by reference in their entirety). Buckwheat flour produced from seeds matured at low temperature (15 or 18° C.) is therefore more valuable than from seeds matured at 22 or 30° C. Buckwheat seeds can be an excellent and natural source for production of medicines used by diabetes patients (U.S. Pat. No. 6,162,795 to Obendorf et al; U.S. Pat. No. 6,492,341 to Obendorf et al., which are hereby incorporated by reference in their entirety).

High temperature during buckwheat seed maturation enhanced the biosynthesis of di-a-galactosides of D-chiro-inositol (fagopyritol A2 and fagopyritol B2) and a-galactosides of sucrose (raffinose and stachyose). This observation is opposite to our earlier results, where increased level of sucrose galactosides was noted in buckwheat embryos of seeds matured at 18° C. in comparison to embryos from seeds matured at 25° C. (Horbowicz at al., *Planta* 205:1-11 (1998), which is hereby incorporated by reference in its entirety). Similarly, in the present study, a higher level of galactinol, the substrate for biosynthesis of raffinose and stachyose, was found in buckwheat embryos matured at higher temperatures. Galactinol is the galactosyl donor for both raffinose and stachyose biosynthesis, as well as the digalactoside of myo-inositol. According to Castillo et al., *J. Agric. Food Chem.* 38:351-355 (1990), which is hereby incorporated by reference in its entirety, low temperature during soybean seed maturation promotes galactinol biosynthesis. In buckwheat is the opposite situation—high temperature promotes accumulation of galactinol, raffinose, and stachyose. Based on that it was concluded that physiological response to temperature stress during seed maturation in buckwheat is different than what occurs in legumes (Castillo et al., *J. Agric. Food Chem.* 38:351-355 (1990); Gorecki et al., *Crop Sci.* 36:1277-1282 (1996), which are hereby incorporated by reference in their entirety). In fact, for growing of legumes, high temperatures are needed, whereas for buckwheat, daily temperatures 17 to 19° C. are optimal.

Surprisingly, germination was higher in case of buckwheat seeds matured at 30° C. than for those matured at 15 or 22° C. Lowest germination rate was found in seeds matured at 22° C. Possibly during maturation of buckwheat seeds at 22° C. germination inhibitors are biosynthesized in higher concentration and they affect the proteolytic enzymes during germination (Belozersky et al., *J. Plant Physiol.* 46(3):330-339 (1999), which is hereby incorporated by reference in its entirety). Seeds matured at 15° C. have delayed maturation, and therefore inhibitors are probably absent or in low, insufficient quantities. At 30° C. seeds mature very fast and it is quite possible that these seeds have lower levels of germination inhibitors, due to the shorter time of maturation.

Example 7

Buckwheat Explant Feeding Experiments

Buckwheat explants, consisting of a stem segment with attached leaf and terminal floral cluster, were patterned after the soybean explants described in Example 4. This example uses the buckwheat explant system to study the transport of cyclitols, fed through the stem, to the developing buckwheat seed and their incorporation into fagopyritols. D-chiro-inositol, D-pinitol, or myo-inositol (100 mM in 1% sucrose) or 1% sucrose (without cyclitols) were fed to buckwheat explants through the stem for 5 days and then the seeds were slow dried. Soluble carbohydrates were extracted and analyzed from embryos of the seeds and from leaf disks. The results are shown in Tables 19-25, below.

TABLE 19

Soluble carbohydrates (μg/embryo) in embryos of seeds from buckwheat explants fed 100 mM D-chiro-inositol in 1% sucrose solution - feeding 5 days before slow drying (micrograms/embryo)

| Soluble Carbohydrate | After 1 day feeding | After 5 days feeding | 2 days slow drying | 4 days slow drying | 7 days slow drying |
|---|---|---|---|---|---|
| D-Pinitol | 0 | 0 | 0 | 0 | 0 |
|  | 0 | 0 | 0 | 0 | 0 |
| D-chiro-Inositol | 2.28 | 93.10 | 1.32 | 2.20 | 56.97 |
|  | 14.89 | 87.78 | 25.03 | 44.55 | 41.29 |
|  |  | 122.37 |  | 138.86 | 55.10 |
| myo-Inositol | 1.63 | 2.03 | 1.84 | 3.29 | 2.20 |
|  | 1.71 | 4.59 | 1.88 | 2.64 | 1.20 |
|  |  | 2.74 |  | 2.19 | 1.10 |
| Sucrose | 66.64 | 268.14 | 124.83 | 202.99 | 162.68 |
|  | 232.10 | 90.04 | 185.14 | 147.00 | 121.44 |
|  |  | 202.20 |  | 118.11 | 121.99 |
| Galactopinitol A | 0 | 0 | 0 | 0 | 0 |
|  | 0 | 0 | 0 | 0 | 0 |
|  |  | 0 |  | 0 | 0 |
| Galactopinitol B | 0 | 0 | 0 | 0 | 0 |
|  | 0 | 0 | 0 | 0 | 0 |
|  |  | 0 |  | 0 | 0 |
| Fagopyritol A1 | 0 | 10.71 | 25.53 | 27.38 | 41.11 |
|  | 0 | 133.47 | 117.32 | 42.86 | 21.71 |
|  |  | 69.49 |  | 52.16 | 27.96 |
| Fagopyritol B1 | 0 | 33.64 | 127.23 | 125.16 | 298.43 |
|  | 0 | 623.00 | 635.89 | 388.66 | 190.64 |
|  |  | 322.50 |  | 270.67 | 208.33 |
| Galactinol | 0 | 3.15 | 9.84 | 6.82 | 7.21 |
|  | 0 | 3.75 | 3.63 | 3.90 | 1.71 |
|  |  | 2.62 |  | 2.70 | 0 |
| Fagopyritol A2 | 0 | 0 | 6.43 | 4.19 | 2.57 |
|  | 0 | 10.11 | 4.91 | 2.04 | 1.19 |
|  |  | 1.93 |  | 4.42 | 1.33 |
| Fagopyritol B2 | 0 | 0 | 5.51 | 3.95 | 2.28 |
|  | 0 | 5.48 | 3.45 | 2.83 | 0.91 |
|  |  | 1.72 |  | 1.57 | 1.99 |
| Digalactosyl myo-inositol | 0 | 0 | 0 | 0 | 0 |
|  | 0 | 0 | 0 | 0 | 0 |
|  |  | 0 |  | 0 | 0 |

TABLE 20

Soluble carbohydrates (μg/embryo) in embryos of seeds from buckwheat explants fed 100 mM D-pinitol in 1% sucrose solution - feeding 5 days before slow drying (micrograms/embryo)

| Soluble Carbohydrate | After 1 day feeding | After 5 days feeding | 2 days slow drying | 4 days slow drying | 7 days slow drying |
|---|---|---|---|---|---|
| D-Pinitol | 35.53 | 204.10 | 230.83 | 134.07 | 148.04 |
|  | | 263.02 | 163.47 | 162.97 | 85.34 |
|  | | 328.27 | 56.90 | 173.51 | 129.52 |
| D-chiro-Inositol | 4.50 | 1.32 | 1.51 | 2.19 | 1.97 |
|  | | 28.25 | 0.70 | 4.78 | 1.01 |
|  | | 9.41 | 0.94 | 1.11 | 7.71 |
| myo-Inositol | 1.00 | 1.38 | 6.63 | 5.34 | 2.78 |
|  | | 4.60 | 3.07 | 4.92 | 3.38 |
|  | | 3.43 | 1.37 | 4.81 | 3.33 |
| Sucrose | 212.67 | 89.73 | 106.43 | 87.98 | 84.50 |
|  | | 86.41 | 167.61 | 229.72 | 122.05 |
|  | | 147.85 | 84.96 | 104.05 | 177.42 |
| Galactopinitol A | 0 | 0 | 0 | 3.39 | 6.41 |
|  | | 6.18 | 12.91 | 0 | 9.09 |
|  | | 5.84 | 6.68 | 0 | 0 |
| Galactopinitol B | 0 | 1.61 | 4.39 | 5.88 | 0 |
|  | | 1.10 | 0 | 0 | 1.81 |
|  | | 1.90 | 0 | 0 | 0 |
| Fagopyritol A1 | 0 | 0 | 2.38 | 16.78 | 10.82 |
|  | | 21.43 | 29.81 | 39.10 | 12.44 |
|  | | 22.91 | 23.96 | 15.80 | 20.01 |

TABLE 20-continued

Soluble carbohydrates (μg/embryo) in embryos of seeds from buckwheat explants fed 100 mM D-pinitol in 1% sucrose solution - feeding 5 days before slow drying (micrograms/embryo)

| Soluble Carbohydrate | After 1 day feeding | After 5 days feeding | 2 days slow drying | 4 days slow drying | 7 days slow drying |
|---|---|---|---|---|---|
| Fagopyritol B1 | 1.44 | 0.98 | 7.29 | 116.5 | 64.64 |
|  |  | 90.76 | 165.96 | 165.56 | 77.20 |
|  |  | 75.14 | 111.41 | 77.90 | 119.44 |
| Galactinol | 2.51 | 0 | 10.69 | 2.68 | 0 |
|  |  | 3.26 | 7.75 | 4.14 | 1.24 |
|  |  | 3.40 | 2.79 | 3.31 | 0 |
| Fagopyritol A2 | 0 | 0 | 0 | 6.18 | 1.30 |
|  |  | 0 | 9.52 | 6.64 | 0.71 |
|  |  | 4.65 | 6.89 | 4.73 | 2.21 |
| Fagopyritol B2 | 0 | 0 | 0 | 5.70 | 1.60 |
|  |  | 0 | 6.69 | 4.29 | 0.48 |
|  |  | 4.98 | 4.46 | 2.47 |  |
| Digalactosyl myo-inositol | 0 | 0 | 0 | 0 | 0 |
|  |  | 0 | 0 | 1.05 | 0 |
|  |  | 0 | 0 | 0 | 0 |

TABLE 21

Soluble carbohydrates (μg/embryo) in embryos of seeds from buckwheat explants fed 100 mM myo-inositol in 1% sucrose solution - feeding 5 days before slow drying (micrograms/embryo)

| Soluble Carbohydrate | After 1 day feeding | After 5 days feeding | 2 days slow drying | 4 days slow drying | 7 days slow drying |
|---|---|---|---|---|---|
| D-Pinitol | 0 | 0 | 0 | tr | tr |
|  |  | tr | 0 | tr | tr |
| D-chiro-inositol | 6.45 | 15.19 | 6.42 | 3.54 | 14.01 |
|  |  | 126.48 | 1.07 | 6.67 | 9.90 |
| myo-Inositol | 4.56 | 4.93 | 1.67 | 3.66 | 2.37 |
|  |  | 4.72 | 0 | 2.27 | 2.11 |
| Sucrose | 306.16 | 225.64 | 313.35 | 180.43 | 163.04 |
|  |  | 74.48 | 66.92 | 161.20 | 121.70 |
| Galactopinitol A | 0 | 0 | 0 | 0 | 0 |
|  |  | 0 | 0 | 0 | 0 |
| Galactopinitol B | 0 | 0 | 0 | 0 | 0 |
|  |  | 0 | 0 | 0 | 0 |
| Fagopyritol A1 | 0 | 18.90 | 62.19 | 19.72 | 14.49 |
|  |  | 10.94 | 29.81 | 41.42 | 34.61 |
| Fagopyritol B1 | 0 | 95.33 | 300.84 | 111.78 | 79.17 |
|  |  | 44.47 | 129.87 | 183.36 | 188.73 |
| Galactinol | 0 | 19.19 | 10.36 | 8.41 | 2.09 |
|  |  | 3.71 | 3.46 | 4.79 | 0 |
| Fagopyritol A2 | 0 | 2.60 | 38.72 | 11.49 | 2.54 |
|  |  | 0 | 10.89 | 4.52 | 2.64 |
| Fagopyritol B2 | 0 | 1.62 | 35.81 | 13.37 | 3.53 |
|  |  | 0 | 3.22 | 3.31 | 2.57 |
| Digalactosyl myo-inositol | 0 | 0.85 | 6.63 | 2.13 | 0.35 |
|  |  | 0 | 8.61 | 0 | 0 |

TABLE 22

Soluble carbohydrates (μg/embryo) in embryos of seeds from buckwheat explants fed 1% sucrose (without cyclitols) solution - feeding 5 days before slow drying (micrograms/embryo)

| Soluble Carbohydrate | After 1 day feeding | After 5 days feeding | 2 days slow drying | 4 days slow drying | 7 days slow drying |
|---|---|---|---|---|---|
| D-Pinitol |  | 0 | 0 | 0 | 0 |
|  |  | tr | tr | 0 | tr |
|  |  |  | tr |  |  |
| D-chiro-Inositol |  | 3.22 | 5.57 | 1.94 | 14.09 |
|  |  | 24.47 | 8.02 | 2.09 | 5.09 |
|  |  |  | 26.74 |  |  |
| myo-Inositol |  | 1.50 | 3.63 | 6.44 | 2.46 |
|  |  | 17.80 | 2.71 | 2.94 | 4.07 |
|  |  |  | 2.30 |  |  |
| Sucrose |  | 211.90 | 111.20 | 189.33 | 177.61 |
|  |  | 524.20 | 141.36 | 105.55 | 246.49 |
|  |  |  | 151.69 |  |  |
| Galactopinitol A |  | 0 | 0 | 0 | 0 |
|  |  | tr | 0 | 0 | 0 |
|  |  |  | tr |  |  |
| Galactopinitol B |  | 0 | 0 | 0 | 0 |
|  |  | tr | 0 | 0 | 0 |
|  |  |  | 0 |  |  |
| Fagopyritol A1 |  | 0.70 | 12.27 | 16.02 | 23.01 |
|  |  | 27.67 | 51.20 | 14.64 | 15.97 |
|  |  |  | 76.65 |  |  |
| Fagopyritol B1 |  | 0.87 | 55.08 | 89.92 | 138.32 |
|  |  | 151.69 | 237.27 | 72.98 | 111.37 |
|  |  |  | 476.65 |  |  |
| Galactinol |  | 1.47 | 15.87 | 26.38 | 0 |
|  |  | 19.03 | 10.02 | 8.45 | 5.93 |
|  |  |  | 5.03 |  |  |
| Fagopyritol A2 |  | 0 | 0.58 | 10.60 | 7.35 |
|  |  | 8.12 | 12.29 | 6.87 | 6.34 |
|  |  |  | 8.09 |  |  |
| Fagopyritol B2 |  | 0 | 0.66 | 11.05 | 7.65 |
|  |  | 6.72 | 10.83 | 5.72 | 6.34 |
|  |  |  | 4.39 |  |  |
| Digalactosyl myo-inositol |  | 0 | 0 | 2.98 | 0.82 |
|  |  | 3.02 | 0.60 | 0.74 | 1.48 |
|  |  |  | 0 |  |  |

TABLE 23

Soluble carbohydrates (μg/10 mg leaf disk) in leaves from buckwheat explants fed 100 mM D-chiro-inositol in 1% sucrose solution - leaf composition, micrograms in 10 mg disc

| Soluble Carbohydrate | After 1 hour feeding | After 24 hours feeding | After 72 hours feeding |
|---|---|---|---|
| Fructose | 2.05 | 19.96 | 115.25 |
| Glucose | 3.90 | 16.53 | 77.78 |
| D-Pinitol | 0 | 0 | 0 |
| D-chiro-inositol | 2.06 | 21.16 | 72.91 |
| myo-Inositol | 3.76 | 1.88 | 3.91 |
| Sucrose | 16.50 | 15.13 | 16.15 |

TABLE 24

Soluble carbohydrates (μg/10 mg leaf disk) in leaves from buckwheat explants fed 100 mM D-pinitol in 1% sucrose solution - leaf composition, micrograms in 10 mg disc

| Soluble Carbohydrate | After 1 hour feeding | After 24 hours feeding | After 72 hours feeding |
|---|---|---|---|
| Fructose | 53.82 | 60.78 | 42.84 |
| Glucose | 35.78 | 48.92 | 35.53 |
| D-Pinitol | 2.45 | 121.45 | 64.73 |
| D-chiro-Inositol | 3.42 | 4.82 | 3.71 |
| myo-Inositol | 4.46 | 3.05 | 4.23 |
| Sucrose | 84.83 | 2.18 | 9.04 |

TABLE 25

Soluble carbohydrates (µg/10 mg leaf disk) in
leaves from buckwheat explants fed 1% sucrose
(without cyclitols) solution - leaf composition,
micrograms in 10 mg disc

| Soluble Carbohydrate | After 1 hour feeding | After 24 hours feeding | After 72 hours feeding |
|---|---|---|---|
| Fructose | 4.05 | 20.25 | 23.35 |
| Glucose | 4.63 | 10.35 | 8.01 |
| D-Pinitol | 0 | 0 | 0 |
| D-chiro-Inositol | 3.51 | 3.81 | 6.26 |
| myo-Inositol | 4.21 | 5.58 | 8.45 |
| Sucrose | 39.23 | 14.29 | 17.40 |

Based on the above data it was determined that feeding D-chiro-inositol to buckwheat explants increased free D-chiro-inositol 40 fold in leaves demonstrating the transport of cyclitols to leaves via the transpiration stream. Feeding D-pinitol to buckwheat explants increased free D-pinitol dramatically in leaves. D-Pinitol does not accumulate in buckwheat leaves or seeds of explants fed D-chiro-inositol, myo-inositol, or sucrose without cyclitols. Galactosyl cyclitols, raffinose, and sucrose do not accumulate in leaf tissues. Feeding D-chiro-inositol to buckwheat explants increased free D-chiro-inositol 3 to 10 fold and fagopyritol B1 2 fold in embryos of buckwheat seeds demonstrating the transport of D-chiro-inositol to buckwheat seeds and its incorporation into fagopyritols. Feeding D-pinitol to buckwheat explants increased free D-pinitol in buckwheat embryos demonstrating the transport of D-pinitol to seeds and embryos; these embryos did not accumulate galactopinitols, indicating that buckwheat does not have the enzymes for accumulation of galactopinitols. Signals corresponding to galactopinitol retention times were similar to background signals. Presence of galactopinitols could not be verified. If present, galactopinitols were present only in trace amounts. Results of these experiments further demonstrate that fagopyritols and galactopinitols are biosynthesized by different pathways.

Example 8

Biosynthesis of an Insulin Mediator

Growth of Recombinant *E. coli* and Isolation of Recombinant Proteins cDNAs corresponding to the FeGolS-1, FeGolS-2, and GmGolS genes were inserted into pET-14B expression vectors. The vector also contained a gene for ampicillin resistance and a sequence that codes for six histidines on the N-terminal end of the expressed protein. The vectors containing the gene inserts were used to transform *E. coli* strain BL21, containing the bacteriophage lysogen DE3. The bacteria were then streaked on ampicillin-containing plates and incubated overnight (8-12 hours) at 37° C. One colony from each plate was then transferred to 2 mL of Luria Broth (LB) containing 0.05 mM ampicillin in 10 mL screw-capped Pyrex tubes. The tubes were then placed in an incubator at 37° C. with shaking at 175 rpm overnight (8-12 hours). One mL of the starter cultures was then transferred to 250 mL of the LB-Amp solution and grown under the same conditions for three hours. After three hours, IPTG was added to induce expression of the genes in the pET-14B vector. The bacteria were then grown for another three hours and harvested via centrifugation at 6,000 rpm. Bacteria from 500 mL of LB-Amp were lysed using 5 mL of BugBuster™ solution. Nucleic acids and non-soluble cellular matter were removed from the crude extract by centrifugation and filtration and the soluble extract was then loaded onto a $Ni^{2+}$-NTA column. The target proteins with the N-terminal histidine tag bound to the column while all other soluble proteins were washed away. These enzymes were eluted from the column by the addition of imidazole containing extraction buffer. The protein solution was dialyzed against 5 mM $Mn^{2+}$ solution and then used for enzyme assays.

Enzyme Assays

Assays were completed under varying conditions to begin to characterize the purified galactinol synthase enzymes. Assays were first designed to determine if the enzymes could synthesize galactinol and fagopyritols (A). The optimal concentration of $Mn^{2+}$ for enzyme action was then determined (B). The enzymes were next used in assays to determine their substrate specificity (C). Finally, assays were completed to determine the reaction kinetics of the enzymes (D).

(A) Initial Assays of purified recombinant FeGolS-1, FeGolS-2, and GmGolS enzymes:

It was first determined that the purified recombinant FeGolS-1, FeGolS-2, and GmGolS enzymes could synthesize fagopyritols and galactinol. To determine galactinol synthase activity, assays were completed using myo-inositol as the galactosyl acceptor and UDP-galactose as the galactosyl donor. Approximately 1-2 µg of each enzyme was added to a 50 µL solution containing 20 mM myo-inositol, 20 mM UDP-galactose, 50 mM HEPES, pH 7.0, 2 mM DTT, and 3 mM $Mn^{2+}$ ($MnCl_2$) at 30° C. The reactions were stopped after 3 hours with the addition of 50 µL of 100% EtOH. To determine fagopyritol synthase activity, the same reaction conditions were used, except D-chiro-inositol was used as the galactosyl acceptor instead of myo-inositol.

(B) Optimal Concentration of $Mn^{2+}$:

To determine the concentration of $Mn^{2+}$ in which the enzymes had the greatest activity, multiple assays were completed varying the amount of $Mn^{2+}$. Earlier studies of galactinol synthase enzymes from other plants reported optimal $Mn^{2+}$ concentrations ranging from 1 mM to 15 mM. Two different sets of assays were completed, one using myo-inositol as the galactosyl acceptor, and the other using D-chiro-inositol. In both sets, 1-2 µg of each enzyme was added to a 50 µL solution containing 20 mM galactosyl acceptor, 20 mM UDP-galactose, 50 mM HEPES, pH 7.0, 2 mM DTT, and varying $Mn^{2+}$ concentrations of 0, 1, 3, 5, 10 and 15 mM, at 30° C. After 3 hours, the reactions were stopped with the addition of 50 µL of 100% EtOH.

(C) Substrate Specificity Assays:

The substrate specificity of the three galactinol synthase enzymes was characterized through assays varying the galactosyl acceptor. myo-inositol, D-chiro-inositol, pinitol, L-chiro-inositol, ononitol, bornesitol, sequoyitol, quebrachitol, epi-inositol and scyllo-inositol were used as substrates in reactions with all three enzymes. The reactions were completed using 1-2 µg of enzyme in a 50 µL solution containing 20 mM galactosyl acceptor, 20 mM UDP-galactose, 50 mM HEPES, pH 7.0, 2 mM DTT, 5 mM $Mn^{2+}$ at 30° C. After 3 hours, the reactions were stopped with the addition of 50 µL of 100% EtOH.

(D) Reaction Kinetics:

The assays to determine the $K_m$ and $V_{max}$ of the enzymes in the synthesis of galactinol from myo-inositol and UDP-galactose were set up as follows:

Reaction A: 5 mM myo-inositol
    20 mM UDP-Galactose
    1 mM DTT 50 mM Hepes, pH 7.0
5 mM $MnCl_2$
Reaction B: 10 mM myo-inositol
  20 mM UDP-Galactose
  1 mM DTT
  50 mM Hepes, pH 7.0
  5 mM $MnCl_2$
Reaction C: 15 mM myo-inositol
  20 mM UDP-Galactose
  1 mM DTT
  50 mM Hepes, pH 7.0
  5 mM $MnCl_2$
Reaction D: 20 mM myo-inositol
  20 mM UDP-Galactose
  1 mM DTT
  50 mM Hepes, pH 7.0
  5 mM $MnCl_2$
Reaction E: 25 mM myo-inositol
  20 mM UDP-Galactose
  1 mM DTT
  50 mM Hepes, pH 7.0
  5 mM $MnCl_2$ The assays to determine the $K_m$ and $V_{max}$ of the enzymes in the synthesis of fagopyritol A1 and fagopyritol B1 from D-chiro-inositol and UDP-galactose were set up as follows:
Reaction A: 5 mM D-chiro-inositol
  20 mM UDP-Galactose
  1 mM DTT
  50 mM Hepes, pH 7.0
  5 mM $MnCl_2$
Reaction B: 10 mM D-chiro-inositol
  20 mM UDP-Galactose
  1 mM DTT
  50 mM Hepes, pH 7.0
  5 mM $MnCl_2$
Reaction C: 15 mM D-chiro-inositol
  20 mM UDP-Galactose
  1 mM DTT
  50 mM Hepes, pH 7.0
  5 mM $MnCl_2$
Reaction D: 20 mM D-chiro-inositol
  20 mM UDP-Galactose
  1 mM DTT
  50 mM Hepes, pH 7.0
  5 mM $MnCl_2$
Reaction E: 25 mM D-chiro-inositol
  20 mM UDP-Galactose
  1 mM DTT
  50 mM Hepes, pH 7.0
  5 mM $MnCl_2$ To each reaction, ~4-5 μg of enzyme were added. Each reaction was run for 0, 3, 6, 9, and 12 minutes at 30° C. The reactions were stopped with the addition of 50 μL of 100% EtOH and 25 μL of internal standard. The reactions were then filtered through Nanosep tubes and 100 μL of each reaction added to silyation vials. Samples were dried under nitrogen and stored over $P_2O_5$ overnight. Dry residues were derivatized with 100 μL of trimethylsilylsylimadazole:pyridine (1:1, v/v) at 80° C. for 45 minutes, and 1 μL was injected for GC analysis of products as previously described (Horbowicz et al., *Planta* 205:1-11 (1998), which is hereby incorporated by reference in its entirety) using an HP1-MS capillary column.

All five reactions were plotted on a product concentration vs. time plot. The concentration of the enzyme had to be small enough so that the reaction was still linear after six minutes. The $V_o$ for each reaction was determined by finding the slope of this linear portion of the curve (i.e. if its linear, use the zero point and the concentration of product after three minutes to calculate the slope of that portion of the reaction). Once this was completed, $V_o$ (Rate) versus myo-inositol concentration was plotted. Finally, a Lineweaver-Burke Plot was made by plotting $1/V_o$ vs. 1/[substrate]. If the line was linear, then its slope was the $K_m/V_{max}$. The y-intercept was $1/V_{max}$, the x-intercept was $-1/K_m$.

All samples from the assays were analyzed by gas chromatography. All were prepared for analysis in the same way. After addition of 50 μL of 100% EtOH, 25 μL of Internal Standard (25 μg of phenyl α-D-glucoside) was added to the reaction mixture. The solution was then filtered using NanoSep tubes and 100 μL was transferred to a silation vial. The samples were then dried under nitrogen and desiccated over $P_2O_5$ overnight. The dried samples were then derivitized with 100 μL of TMSI:pyridine (1:1, v/v) and then analyzed by gas chromatography.

Synthesis of the Putative Insulin Mediator

Figure 27:
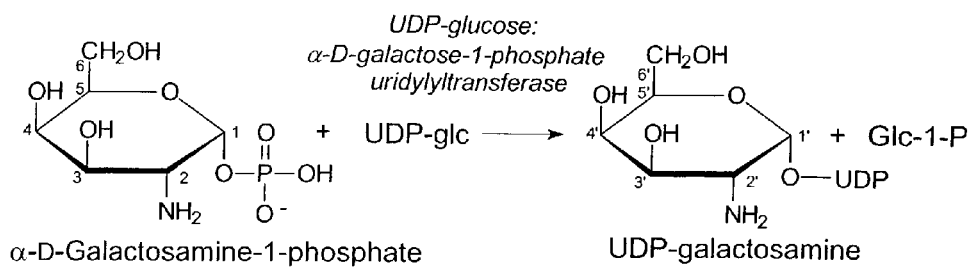
FIG. 27 shows the biosynthesis UDP-galactosamine from α-D-galactose-1-phosphate and UDP-glucose using UDP-glucose:α-D-galactose-1-phosphate uridylyltransferase (EC 2.7.7.9).
Figure 28:
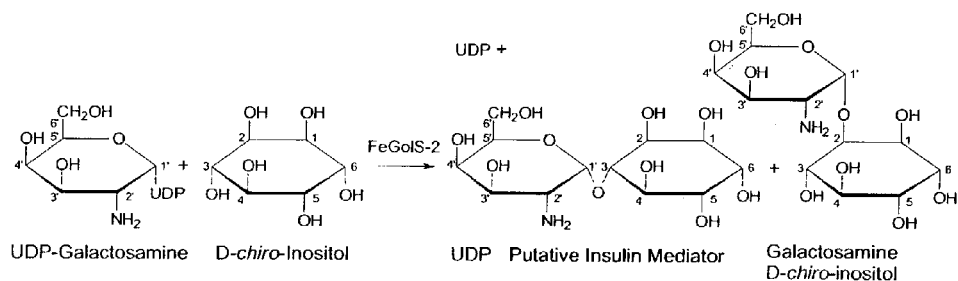
FIG. 28 shows biosynthesis of the putative insulin mediator (2-amino-2-deoxy-α-D-galactosamine-(1-3)-1D-chiro-inositol) and an isomer (2-amino-2-deoxy-α-D-galactosamine-(1-2)-1D-chiro-inositol) plus UDP, using UDP-galactosamine and D-chiro-inositol as substrates. The reaction is catalyzed by the enzyme FeGolS-2.

In order to synthesize the putative insulin mediator, it is necessary to first synthesize UDP-galactosamine. Work was completed developing a protocol for the synthesis of the compound and its purification for use in further assays. UDP-galactosamine was synthesized from galactosamine-1-phosphate (from Sigma). The synthesis was done using the procedure outlined in Heidlas et al., *J. Org. Chem.* 57:152-157 (1992), which is hereby incorporated by reference in its entirety. The procedure uses an uridyltransferase (EC 2.7.7.9) to transfer a UDP moiety from UDP-glucose to galactosamine-1-phosphate to make UDP-galactosamine on a gram scale (FIG. 27). The UDP-galactosamine synthesized in the reaction was purified and desalted using a Bio-Rad P-2 Gel column. The fractions containing UDP-galactosamine were analyzed by HPLC using an Alltech Econosil C18 10U column (250 mm length, 4.6 mm I.D.) and a variable-wavelength detector at 254 nm. The mobile buffer was 20 mM TEAA (triethyl ammonium acetate buffer, pH 7.0) with an increasing gradient of acetonitrile (0-4% acetonitrile) after 30 minutes to clean the column (Rabina et al., *Glycoconjugate J.* 18:799-805 (2001), which is hereby incorporated by reference in its entirety). Identification was based upon retention times determined earlier with known substrates and the developed separation method. Fractions containing UDP-galactosamine were concentrated by freeze drying, and the lyophilized powder containing UDP-galactosamine was resuspended in 1 mL of water. The purified UDP-galactosamine and D-chiro-inositol can now be used as substrates for the recombinant *Fe*GolS-2 enzyme to biosynthesize the insulin mediator galactosamine D-chiro-inositol (FIG. 28). Two products are expected: 2-amino-2-deoxy-α-D-galactosamine-(1-3)-1D-chiro-inositol (a putative insulin mediator) and 2-amino-2-deoxy-α-D-galactosamine-(1-2)-1D-chiro-inositol (isomer of the putative insulin mediator) in addition to UDP. Initial determination of successful synthesis can be assayed by gas chromatography. The peaks corresponding to fagopyritol A1, fagopyritol B1, D-chiro-inositol, and many other soluble carbohydrates are known, and the two galactosamine D-chiro-inositol products should correspond to fagopyritol A1 and fagopyritol B1 with one less hydroxyl for TMS-derivatization resulting in shorter retention times. Synthesis of the insulin mediator can then be optimized in order to obtain appreciable amounts of the compound. Depending on efficiency, carbon-Celite columns, TLC, HPLC, or Dowex ion exchange columns can be used to purify the insulin mediator (and its isomeric form) from the reaction mixture. The purified insulin mediator can then be lyophilized to a white powder. The structure of the purified insulin mediator can be determined by $^1$H-NMR and $^{13}$C-NMR (Obendorf et al., *Carbohydrate Research* 328:623-627 (2000); Steadman et al., *Carbohydrate Research* 331:19-25 (2001), which are incorporated herein by reference in their entirety), to confirm the successful biosynthesis of the insulin mediator. Similarly, substituting L-chiro-inositol, scyllo-inositol, or bornesitol (or other cyclitols reactive with the FeGolS-2 enzyme) in the reaction (FIG. 28) would form products that may be used as inhibitors of the galactosamine D-chiro-inositol insulin mediator.

Discussion

A protocol has been developed that resulted in purification of the target enzymes from the bacterial preparation without loss of activity. Dialysis was used to remove the enzymes from the extraction buffer and into a solution of $Mn^{2+}$ ions. This change retained enzyme activity throughout the purification procedure. Also, adjusting bacterial growth times and preparation methods further maximized the expression system.

Manganese concentration assays were used to determine that optimal enzyme action occurred in 5 mM $Mn^{2+}$ solution.

Results from the substrate specificity assays helped to identify the inositols the enzymes could use as galactosyl acceptors. myo-inositol, D-chiro-inositol, L-chiro-inositol, bornesitol and scyllo-inositol all can be used as galactosyl acceptors by all three enzymes. The $V_{max}$ and $K_m$ has been difficult to determine due to the sensitivity of the reaction. However, initial estimates of the $K_m$ for the enzyme FeGolS-2 using myo-inositol as a substrate was 7.53 mM and the $V_{max}$ 0.0817 µM/min. Determination of the $V_{max}$ and $K_m$ has proven difficult for the synthesis of fagopyritols because there are multiple products produced in the reaction.

Reactions to synthesize UDP-galactosamine and purification of the compound have been completed (FIG. 27). UDP-galactosamine can then be used as the galactosyl donor in the reaction synthesizing the putative insulin mediator (FIG. 28).

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method for producing a fagopyritol, an insulin mediator, an insulin mediator analogue, an insulin mediator homologue, or an insulin mediator inhibitor comprising:

expressing a nucleic acid encoding a fagopyritol synthase comprising the amino acid sequence of SEQ ID NO:4;

providing a galactosyl donor and a galactosyl acceptor; and combining the fagopyritol synthase with the galactosyl donor and the galactosyl acceptor under conditions effective to produce a fagopyritol, an insulin mediator, an insulin mediator analogue, or an insulin mediator homologue.

2. The method according to claim 1, wherein the galactosyl donor is UDP-galactose.

3. The method according to claim 1, wherein the galactosyl donor is UDP-galactosamine.

4. The method according to claim 1, wherein the galactosyl acceptor is selected from the group consisting of D-chiro-inositol, L-chiro-inositol, myo-inositol, bornesitol, and scyllo-inositol.

5. The method according to claim 4, wherein the galactosyl acceptor is D-chiro-inositol.

6. The method according to claim 1, wherein the fagopyritol synthase is purified.

* * * * *

SEQUENCE LISTING

<160> NUMBER OF SEQ ID NOS: 30

<210> SEQ ID NO 1
<211> LENGTH: 1269
<212> TYPE: DNA
<213> ORGANISM: Fagopyrum esculentum

<400> SEQUENCE: 1

```
gagcacccaa agctctgcta gcaccatatt caaatcctca agaatcatca aatcttccaa      60
ccaatcctca agttccaacc aaatggcacc agaactcatc acaatcggag ccgatcactc     120
gattttgcca gcggaatcgt tgattccggt tgaccgagct tacgtgacgt ttctcgccgg     180
gaacggagac tatgtcaagg gagttgtcgg attagcaaag ggactgagga aagtgaaggc     240
tgcttatcct cttgttgtag cggttttacc ggacgttccg ctagagcatc gccgactcct     300
ggaggcgcag ggttgtatcg taagggaaat cgagccgata tacccgccgg aaaacaattg     360
cgagttcgct cacgcatact atgtcatcaa ctactccaag cttcgcatct gggagtttgt     420
ggagtacagt aagatgatat acttggacgg ggacatacag gtgtaccaga acattgacca     480
cctgtttgac cagccggacg gctacttta cgcggtgatg gactgttttt gtgagccatc     540
atggagcaag acgattcagt acaagatcgg atactgccaa cagtgcccgg agaaggtagc     600
gtggccgttg gaggctggcc cgaagccttc tctgtacttc aatgccggat tctttgttta     660
cgagccgagc cttgagactt acaaggatct cattgacact ctcaaagtca cgactcctac     720
ctcctttgcc gagcaggact tcttgaacat gtacttcaag gacaagttca agccactccc     780
catagactac aacttagtct tagccttcct gtggaggcat ccggagaaag ttgaccttaa     840
ccgagtgaag gtagttcact actgtgcggc ggggtctaag ccatggaggt acacgggcaa     900
ggaagagaac atggacagag aagacatcaa attgcttgtg aaaaaatggt gggatatcta     960
caacgacgag tcattggacc tcaagaaacc ggtccattta gtgcagcagc ccacggaggt    1020
gctcaaggcg gcgctctcgg aggctaggcc tgttaaatat gtggctgctc cttccgcagc    1080
ttaagtatcg gcttgtattt ggtaatggtt tttgttttg cgaatgtaaa gtagaaagaa    1140
```

```
ggggcgagag tttgtgatat tggggcaatg gggaatggtg cgtataaatg tgtgttgtaa    1200
tggcaactgt ttttacttgg aattatatgt aagaagtaag aatatatgta taaaaaaaaa    1260
aaaaaaaaa                                                            1269
```

<210> SEQ ID NO 2
<211> LENGTH: 333
<212> TYPE: PRT
<213> ORGANISM: Fagopyrum esculentum

<400> SEQUENCE: 2

```
Met Ala Pro Glu Leu Ile Thr Ile Gly Ala Asp His Ser Ile Leu Pro
 1               5                  10                  15

Ala Glu Ser Leu Ile Pro Val Asp Arg Ala Tyr Val Thr Phe Leu Ala
            20                  25                  30

Gly Asn Gly Asp Tyr Val Lys Gly Val Val Gly Leu Ala Lys Gly Leu
        35                  40                  45

Arg Lys Val Lys Ala Ala Tyr Pro Leu Val Val Ala Val Leu Pro Asp
    50                  55                  60

Val Pro Leu Glu His Arg Arg Leu Leu Glu Ala Gln Gly Cys Ile Val
65                  70                  75                  80

Arg Glu Ile Glu Pro Ile Tyr Pro Pro Glu Asn Asn Cys Glu Phe Ala
                85                  90                  95

His Ala Tyr Tyr Val Ile Asn Tyr Ser Lys Leu Arg Ile Trp Glu Phe
            100                 105                 110

Val Glu Tyr Ser Lys Met Ile Tyr Leu Asp Gly Asp Ile Gln Val Tyr
        115                 120                 125

Gln Asn Ile Asp His Leu Phe Asp Gln Pro Asp Gly Tyr Phe Tyr Ala
    130                 135                 140

Val Met Asp Cys Phe Cys Glu Pro Ser Trp Ser Lys Thr Ile Gln Tyr
145                 150                 155                 160

Lys Ile Gly Tyr Cys Gln Gln Cys Pro Glu Lys Val Ala Trp Pro Leu
                165                 170                 175

Glu Ala Gly Pro Lys Pro Ser Leu Tyr Phe Asn Ala Gly Phe Phe Val
            180                 185                 190

Tyr Glu Pro Ser Leu Glu Thr Tyr Lys Asp Leu Ile Asp Thr Leu Lys
        195                 200                 205

Val Thr Thr Pro Thr Ser Phe Ala Glu Gln Asp Phe Leu Asn Met Tyr
    210                 215                 220

Phe Lys Asp Lys Phe Lys Pro Leu Pro Ile Asp Tyr Asn Leu Val Leu
225                 230                 235                 240

Ala Phe Leu Trp Arg His Pro Glu Lys Val Asp Leu Asn Arg Val Lys
                245                 250                 255

Val Val His Tyr Cys Ala Ala Gly Ser Lys Pro Trp Arg Tyr Thr Gly
            260                 265                 270

Lys Glu Glu Asn Met Asp Arg Glu Asp Ile Lys Leu Leu Val Lys Lys
        275                 280                 285

Trp Trp Asp Ile Tyr Asn Asp Glu Ser Leu Asp Leu Lys Lys Pro Val
    290                 295                 300

His Leu Val Gln Gln Pro Thr Glu Val Leu Lys Ala Ala Leu Ser Glu
305                 310                 315                 320

Ala Arg Pro Val Lys Tyr Val Ala Ala Pro Ser Ala Ala
                325                 330
```

<210> SEQ ID NO 3

<211> LENGTH: 1326
<212> TYPE: DNA
<213> ORGANISM: Fagopyrum esculentum

<400> SEQUENCE: 3

| | | |
|---|---|---|
| ttggtttcga acttgatcaa aacctcacaa aaacacgtaa gcaaaatgac ttccgagatg | 60 |
| gcgccacaga acataacgaa tgcagaaaga ggagccgagc aagtgaagcc gtcgagccag | 120 |
| ccaagccgag cctacgtgac attcttagcc gggaacggtg actacgtgaa gggagttata | 180 |
| gggctcgcca aaggcctgag gaaaactcag agcggttacc cgcttgtggt ggcggttctc | 240 |
| cctgacgttc cgcaggagca ccgccgtatg ctggtggcgc aaggctgtat aataaaggaa | 300 |
| atccagcccg ttaacccgcc cgataaccag actcagtttg ccatggctta ttacgtcatc | 360 |
| aactactcca agctccgtat atgggagttt atcgagtata gtaagatgat atatcttgat | 420 |
| ggagacatcc aagtttacga caacatcgac cacctcttcg acctaccaga cgggtacttg | 480 |
| tacggtgcca tggattgctt tgcgagaag acttggagtc attcgcttcc atataagatt | 540 |
| gggtattgcc aacagtgccc ggacagggtc cagtggcccg aaaggctcgg cccaaaacca | 600 |
| acactctact tcaatgcagg gatgttcatc ttcgagccta gcgtttctac ttataatgat | 660 |
| ctccttcata cactcgagat cacccctcct acaccttttg ctgagcagga cttttttgaat | 720 |
| atgtacttca aggatgtgta cagaccaatt ccgaacgttt acaacttggt attggctttg | 780 |
| ttgtggtatc atcctgggtt aatgaagctt gatgaggtta aagtcgttca ctattgtgcc | 840 |
| gatggttcaa accatggcg gtatacaggg aaggggata acatggacag gaagacgtt | 900 |
| aggatgctag tgaagaagtg gtgggagatt tacgatgatc agtctctcga ccctcagcct | 960 |
| aagatggtcg agggcaagaa gttcgacaaa ttagaggagt acagcgagtc cctcgaccac | 1020 |
| ccgcccaagg tggcagagga agataagcta gagaagccca tggcagcgat gacaggcttc | 1080 |
| agctacgtac acgccccgtc tgctgcctga tttgttgaaa caaggccaag gttccacaaa | 1140 |
| tgagggaatc aaaaacctcc tatagtatta tagatcgtat atttctgtta ttgctttcca | 1200 |
| attaagcaac taagatgttc atatagtagt tctggaaaat gaatacgggc atagttgtga | 1260 |
| acttgtaatc tcattttgtt tttcggaatg ttcaagtatt tcttctaaaa aaaaaaaaaa | 1320 |
| aaaaaa | 1326 |

<210> SEQ ID NO 4
<211> LENGTH: 354
<212> TYPE: PRT
<213> ORGANISM: Fagopyrum esculentum

<400> SEQUENCE: 4

Met Thr Ser Glu Met Ala Pro Gln Asn Ile Thr Asn Ala Glu Arg Gly
1               5                  10                  15

Ala Glu Gln Val Lys Pro Ser Ser Gln Pro Ser Arg Ala Tyr Val Thr
            20                  25                  30

Phe Leu Ala Gly Asn Gly Asp Tyr Val Lys Gly Val Ile Gly Leu Ala
        35                  40                  45

Lys Gly Leu Arg Lys Thr Gln Ser Gly Tyr Pro Leu Val Val Ala Val
    50                  55                  60

Leu Pro Asp Val Pro Gln Glu His Arg Arg Met Leu Val Ala Gln Gly
65                  70                  75                  80

Cys Ile Ile Lys Glu Ile Gln Pro Val Asn Pro Pro Asp Asn Gln Thr
                85                  90                  95

Gln Phe Ala Met Ala Tyr Tyr Val Ile Asn Tyr Ser Lys Leu Arg Ile

```
              100                 105                 110
Trp Glu Phe Ile Glu Tyr Ser Lys Met Ile Tyr Leu Asp Gly Asp Ile
        115                 120                 125
Gln Val Tyr Asp Asn Ile Asp His Leu Phe Asp Leu Pro Asp Gly Tyr
    130                 135                 140
Leu Tyr Gly Ala Met Asp Cys Phe Cys Glu Lys Thr Trp Ser His Ser
145                 150                 155                 160
Leu Pro Tyr Lys Ile Gly Tyr Cys Gln Gln Cys Pro Asp Arg Val Gln
                165                 170                 175
Trp Pro Glu Arg Leu Gly Pro Lys Pro Thr Leu Tyr Phe Asn Ala Gly
            180                 185                 190
Met Phe Ile Phe Glu Pro Ser Val Ser Thr Tyr Asn Asp Leu Leu His
        195                 200                 205
Thr Leu Glu Ile Thr Pro Pro Thr Pro Phe Ala Glu Gln Asp Phe Leu
    210                 215                 220
Asn Met Tyr Phe Lys Asp Val Tyr Arg Pro Ile Pro Asn Val Tyr Asn
225                 230                 235                 240
Leu Val Leu Ala Leu Leu Trp Tyr His Pro Gly Leu Met Lys Leu Asp
                245                 250                 255
Glu Val Lys Val Val His Tyr Cys Ala Asp Gly Ser Lys Pro Trp Arg
            260                 265                 270
Tyr Thr Gly Lys Gly Asp Asn Met Asp Arg Glu Asp Val Arg Met Leu
        275                 280                 285
Val Lys Lys Trp Trp Glu Ile Tyr Asp Asp Gln Ser Leu Asp Pro Gln
    290                 295                 300
Pro Lys Met Val Glu Gly Lys Lys Phe Asp Lys Leu Glu Glu Tyr Ser
305                 310                 315                 320
Glu Ser Leu Asp His Pro Pro Lys Val Ala Glu Glu Asp Lys Leu Glu
                325                 330                 335
Lys Pro Met Ala Ala Met Thr Gly Phe Ser Tyr Val His Ala Pro Ser
            340                 345                 350
Ala Ala

<210> SEQ ID NO 5
<211> LENGTH: 986
<212> TYPE: DNA
<213> ORGANISM: Fagopyrum esculentum

<400> SEQUENCE: 5
gctcacgcat actatgtcat caactactcc aagctccgta tatgggagtt tatcgagtat      60
agtaagatga tatatcttga tggagacatc caagtttacg acaacatcga ccacctcttc     120
gacctaccag acgggtactt gtacggtgcc atggattgct tttgcgagaa gacttggagt     180
cattcgcttc catataagat tgggtattgc caacagtgcc cggacagggt ccagtggccc     240
gaaaggctcg gcccaaaacc aacactctac ttcaatgcag ggatgttcat cttcgagcct     300
agcgtttcta cttataatga tctccttcat acactcgaga tcaccccctcc tacacctttt     360 gctgagcagg acttttttgaa tatgtacttc aaggatgtgt acagaccaat tccgaacgtg     420
tacaacttgg tattggcttt gttgtggtat catcctgggt taatgaatct tgatgaggtt     480
aaagtcgttc actattgtgc cgatggttca aaaccatggc ggtatacagg gaaggggggat     540 aacatggaca gggaagacgt taggatgcta gtgaagaagt ggtgggagat ctacgatgat     600
cagtctctcg accctcagcc taaggtggtc gagggcaaga agttcgacaa attagagtac     660
```

```
agcgagtccc tcgaccaccc gcctaaggtg gcagaggaag ataagttaga gaagcccatg      720
gcggcgatga cagggttcag ctacgtacac gccccgtctg ctgcctgact tgttgaaaca      780
aggccaaggt tccacaaatg agggaatcaa aaacctccta tagtattata gatcgtatat      840
ttctgttatt gctttccaat taagcaacta agatgttcat atagtagttc tggaaaatga      900
aaacgggcat agttgtgaac ttgtaatctc attttgtttt tcggaatgtg caagtatttc      960
ttctaaataa aaaaaaaaaa aaaaaa                                           986
```

```
<210> SEQ ID NO 6
<211> LENGTH: 255
<212> TYPE: PRT
<213> ORGANISM: Fagopyrum esculentum

<400> SEQUENCE: 6
```

```
Ala His Ala Tyr Tyr Val Ile Asn Tyr Ser Lys Leu Arg Ile Trp Glu
  1               5                  10                  15

Phe Ile Glu Tyr Ser Lys Met Ile Tyr Leu Asp Gly Asp Ile Gln Val
             20                  25                  30

Tyr Asp Asn Ile Asp His Leu Phe Asp Leu Pro Asp Gly Tyr Leu Tyr
         35                  40                  45

Gly Ala Met Asp Cys Phe Cys Glu Lys Thr Trp Ser His Ser Leu Pro
     50                  55                  60

Tyr Lys Ile Gly Tyr Cys Gln Gln Cys Pro Asp Arg Val Gln Trp Pro
 65                  70                  75                  80

Glu Arg Leu Gly Pro Lys Pro Thr Leu Tyr Phe Asn Ala Gly Met Phe
                 85                  90                  95

Ile Phe Glu Pro Ser Val Ser Thr Tyr Asn Asp Leu Leu His Thr Leu
            100                 105                 110

Glu Ile Thr Pro Pro Thr Pro Phe Ala Glu Gln Asp Phe Leu Asn Met
        115                 120                 125

Tyr Phe Lys Asp Val Tyr Arg Pro Ile Pro Asn Val Tyr Asn Leu Val
    130                 135                 140

Leu Ala Leu Leu Trp Tyr His Pro Gly Leu Met Asn Leu Asp Glu Val
145                 150                 155                 160

Lys Val Val His Tyr Cys Ala Asp Gly Ser Lys Pro Trp Arg Tyr Thr
                165                 170                 175

Gly Lys Gly Asp Asn Met Asp Arg Glu Asp Val Arg Met Leu Val Lys
            180                 185                 190

Lys Trp Trp Glu Ile Tyr Asp Asp Gln Ser Leu Asp Pro Gln Pro Lys
        195                 200                 205

Val Val Glu Gly Lys Lys Phe Asp Lys Leu Glu Tyr Ser Glu Ser Leu
    210                 215                 220

Asp His Pro Pro Lys Val Ala Glu Glu Asp Lys Leu Glu Lys Pro Met
225                 230                 235                 240

Ala Ala Met Thr Gly Phe Ser Tyr Val His Ala Pro Ser Ala Ala
                245                 250                 255
```

```
<210> SEQ ID NO 7
<211> LENGTH: 1406
<212> TYPE: DNA
<213> ORGANISM: Glycine max

<400> SEQUENCE: 7
```

```
agccaaaagt tgttttcat agtgtgtttt gtttcccaaa tcctactctt gtgaccacaa       60
cccttcctcc tctttctttt gaaacctctt tttttctatt cccaaccaa acaagcaaac      120
```

```
gctactcact catcatcact gagatcatgg ctcctaatat caccactgtc aaaaccacca      180
tcaccgacgc tcaagccaag gtcgccaccg atcatggtcg tgcctacgtc accttcctcg      240
ccggaaacgg tgactatgtg aaaggtgtcg ttggcttggc aaaaggtctg agaaaagtga      300
agagcatgta ccctctggtg gttgcagtgc tacccgatgt tccccaagat caccgcaaca      360
ttctcacctc ccaaggttgc attgttagag agattgagcc cgtgtacccc ccagagaatc      420
aaacccagtt tgccatggca tattacgtca tcaactattc aagctacgt atttgggagt      480 tgtggagta cagcaagatg atatacctag acggtgatat ccaagttttt gacaacattg       540
accacttgtt tgacttgcct gataactact tctatgcggt gatggactgt ttctgtgagc      600
caacttgggg ccacactaaa caatatcaga tcggttactg ccagcagtgc ccccataagg      660
ttcagtggcc cactcacttt gggcccaaac ctcctctcta tttcaatgct ggcatgtttg      720
tgtatgagcc caatttggct acttaccgtg acctccttca aacagtccaa gtcacccagc      780
ccacttcctt tgctgaacag gattttttga acatttactt caaggacaaa tataggccaa      840
ttcctaatgt ctacaatctt gtgctggcca tgctgtggcg tcaccctgag aacgttgagc      900
ttgacaaagt taaagtggtt cactactgtg ctgctgggtc taagccttgg aggtacactg      960
ggaaggagga gaatatggag agagaagata tcaagatgtt agtgaaaaag tggtgggata     1020
tatatgagga tgagactttg gactacaaca atccactcaa tgtggataag ttcactgcgg     1080
cacttatgga ggttggtgaa gtcaagttcg tccgtgcccc atctgctgct taagagtgtc     1140
tttggaaatc aagtgtgatc caagtacatg tacaaagtca tacatcatta cattaacttt     1200
tatgtatttc taaagtcat acatcattac attaagtttt atgtatttct aaagtcttaa     1260
gacttaagag gacctttttt atgtgtcccg gcttttcttt ttttcttttt ccaattctgt     1320
cattgtaaag caggtgaata ccggtatcct taattttata aatggatatg aattttattt     1380
tgcaaaaaaa aaaaaaaaaa aaaaaa                                          1406
```

<210> SEQ ID NO 8
<211> LENGTH: 328
<212> TYPE: PRT
<213> ORGANISM: Glycine max

<400> SEQUENCE: 8

```
Met Ala Pro Asn Ile Thr Thr Val Lys Thr Thr Ile Thr Asp Ala Gln
 1               5                  10                  15

Ala Lys Val Ala Thr Asp His Gly Arg Ala Tyr Val Thr Phe Leu Ala
            20                  25                  30

Gly Asn Gly Asp Tyr Val Lys Gly Val Val Gly Leu Ala Lys Gly Leu
        35                  40                  45

Arg Lys Val Lys Ser Met Tyr Pro Leu Val Val Ala Val Leu Pro Asp
    50                  55                  60

Val Pro Gln Asp His Arg Asn Ile Leu Thr Ser Gln Gly Cys Ile Val
65                  70                  75                  80

Arg Glu Ile Glu Pro Val Tyr Pro Pro Glu Asn Gln Thr Gln Phe Ala
                85                  90                  95

Met Ala Tyr Tyr Val Ile Asn Tyr Ser Lys Leu Arg Ile Trp Glu Phe
            100                 105                 110

Val Glu Tyr Ser Lys Met Ile Tyr Leu Asp Gly Asp Ile Gln Val Phe
        115                 120                 125

Asp Asn Ile Asp His Leu Phe Asp Leu Pro Asp Asn Tyr Phe Tyr Ala
    130                 135                 140
```

```
Val Met Asp Cys Phe Cys Glu Pro Thr Trp Gly His Thr Lys Gln Tyr
145                 150                 155                 160

Gln Ile Gly Tyr Cys Gln Gln Cys Pro His Lys Val Gln Trp Pro Thr
                165                 170                 175

His Phe Gly Pro Lys Pro Leu Tyr Phe Asn Ala Gly Met Phe Val
            180                 185                 190

Tyr Glu Pro Asn Leu Ala Thr Tyr Arg Asp Leu Leu Gln Thr Val Gln
                195                 200                 205

Val Thr Gln Pro Thr Ser Phe Ala Glu Gln Asp Phe Leu Asn Ile Tyr
210                 215                 220

Phe Lys Asp Lys Tyr Arg Pro Ile Pro Asn Val Tyr Asn Leu Val Leu
225                 230                 235                 240

Ala Met Leu Trp Arg His Pro Glu Asn Val Glu Leu Asp Lys Val Lys
                245                 250                 255

Val Val His Tyr Cys Ala Ala Gly Ser Lys Pro Trp Arg Tyr Thr Gly
                260                 265                 270

Lys Glu Glu Asn Met Glu Arg Glu Asp Ile Lys Met Leu Val Lys Lys
                275                 280                 285

Trp Trp Asp Ile Tyr Glu Asp Glu Thr Leu Asp Tyr Asn Asn Pro Leu
290                 295                 300

Asn Val Asp Lys Phe Thr Ala Ala Leu Met Glu Val Gly Glu Val Lys
305                 310                 315                 320

Phe Val Arg Ala Pro Ser Ala Ala
                325

<210> SEQ ID NO 9
<211> LENGTH: 344
<212> TYPE: PRT
<213> ORGANISM: Arabidopsis thaliana

<400> SEQUENCE: 9

Met Ala Pro Gly Leu Thr Gln Thr Ala Asp Ala Met Ser Thr Val Thr
1               5                   10                  15

Ile Thr Lys Pro Ser Leu Pro Ser Val Gln Asp Ser Asp Arg Ala Tyr
                20                  25                  30

Val Thr Phe Leu Ala Gly Asn Gly Asp Tyr Val Lys Gly Val Val Gly
                35                  40                  45

Leu Ala Lys Gly Leu Arg Lys Val Lys Ser Ala Tyr Pro Leu Val Val
            50                  55                  60

Ala Met Leu Pro Asp Val Pro Glu Glu His Arg Arg Ile Leu Val Asp
65                  70                  75                  80

Gln Gly Cys Ile Val Arg Glu Ile Glu Pro Val Tyr Pro Pro Glu Asn
                85                  90                  95

Gln Thr Gln Phe Ala Met Ala Tyr Tyr Val Ile Asn Tyr Ser Lys Leu
            100                 105                 110

Arg Ile Trp Lys Phe Val Glu Tyr Ser Lys Met Ile Tyr Leu Asp Gly
        115                 120                 125

Asp Ile Gln Val Tyr Glu Asn Ile Asp His Leu Phe Asp Leu Pro Asp
    130                 135                 140

Gly Tyr Leu Tyr Ala Val Met Asp Cys Phe Cys Glu Lys Thr Trp Ser
145                 150                 155                 160

His Thr Pro Gln Tyr Lys Ile Arg Tyr Cys Gln Gln Cys Pro Asp Lys
                165                 170                 175

Val Gln Trp Pro Lys Ala Glu Leu Gly Glu Pro Pro Ala Leu Tyr Phe
```

-continued

```
            180                 185                 190
Asn Ala Gly Met Phe Leu Tyr Glu Pro Asn Leu Glu Thr Tyr Glu Asp
            195                 200                 205

Leu Leu Arg Thr Leu Lys Ile Thr Pro Thr Pro Phe Ala Glu Gln
210                 215                 220

Asp Phe Leu Asn Met Tyr Phe Lys Lys Ile Tyr Lys Pro Ile Pro Leu
225                 230                 235                 240

Val Tyr Asn Leu Val Leu Ala Met Leu Trp Arg His Pro Glu Asn Val
                245                 250                 255

Glu Leu Gly Lys Val Lys Val Val His Tyr Cys Ala Ala Gly Ser Lys
                260                 265                 270

Pro Trp Arg Tyr Thr Gly Lys Glu Ala Asn Met Glu Arg Glu Asp Ile
            275                 280                 285

Lys Met Leu Val Lys Lys Trp Trp Asp Ile Tyr Asp Asp Glu Ser Leu
            290                 295                 300

Asp Tyr Lys Lys Pro Val Thr Val Val Asp Thr Glu Val Asp Leu Val
305                 310                 315                 320

Asn Leu Lys Pro Phe Ile Thr Ala Leu Thr Glu Ala Gly Arg Leu Asn
                325                 330                 335

Tyr Val Thr Ala Pro Ser Ala Ala
                340

<210> SEQ ID NO 10
<211> LENGTH: 335
<212> TYPE: PRT
<213> ORGANISM: Arabidopsis thaliana

<400> SEQUENCE: 10

Met Ala Pro Glu Ile Asn Thr Lys Leu Thr Val Pro Val His Ser Ala
  1               5                  10                  15

Thr Gly Gly Glu Lys Arg Ala Tyr Val Thr Phe Leu Ala Gly Thr Gly
                20                  25                  30

Asp Tyr Val Lys Gly Val Val Gly Leu Ala Lys Gly Leu Arg Lys Ala
            35                  40                  45

Lys Ser Lys Tyr Pro Leu Val Val Ala Val Leu Pro Asp Val Pro Glu
        50                  55                  60

Asp His Arg Lys Gln Leu Val Asp Gln Gly Cys Val Val Lys Glu Ile
65                  70                  75                  80

Glu Pro Val Tyr Pro Pro Glu Asn Gln Thr Glu Phe Ala Met Ala Tyr
                85                  90                  95

Tyr Val Ile Asn Tyr Ser Lys Leu Arg Ile Trp Glu Phe Val Glu Tyr
            100                 105                 110

Asn Lys Met Ile Tyr Leu Asp Gly Asp Ile Gln Val Phe Asp Asn Ile
        115                 120                 125

Asp His Leu Phe Asp Leu Pro Asn Gly Gln Phe Tyr Ala Val Met Asp
    130                 135                 140

Cys Phe Cys Glu Lys Thr Trp Ser His Ser Pro Gln Tyr Lys Ile Gly
145                 150                 155                 160

Tyr Cys Gln Gln Cys Pro Asp Lys Val Thr Trp Pro Glu Ala Lys Leu
                165                 170                 175

Gly Pro Lys Pro Pro Leu Tyr Phe Asn Ala Gly Met Phe Val Tyr Glu
            180                 185                 190

Pro Asn Leu Ser Thr Tyr His Asn Leu Leu Glu Thr Val Lys Ile Val
        195                 200                 205
```

```
Pro Pro Thr Leu Phe Ala Glu Gln Asp Phe Leu Asn Met Tyr Phe Lys
    210                 215                 220

Asp Ile Tyr Lys Pro Ile Pro Pro Val Tyr Asn Leu Val Leu Ala Met
225                 230                 235                 240

Leu Trp Arg His Pro Glu Asn Ile Glu Leu Asp Gln Val Lys Val Val
                245                 250                 255

His Tyr Cys Ala Ala Gly Ala Lys Pro Trp Arg Phe Thr Gly Glu Glu
            260                 265                 270

Glu Asn Met Asp Arg Glu Asp Ile Lys Met Leu Val Lys Lys Trp Trp
        275                 280                 285

Asp Ile Tyr Asn Asp Glu Ser Leu Asp Tyr Lys Asn Val Val Ile Gly
    290                 295                 300

Asp Ser His Lys Gln Gln Thr Leu Gln Gln Phe Ile Glu Ala Leu
305                 310                 315                 320

Ser Glu Ala Gly Ala Leu Gln Tyr Val Lys Ala Pro Ser Ala Ala
                325                 330                 335

<210> SEQ ID NO 11
<211> LENGTH: 341
<212> TYPE: PRT
<213> ORGANISM: Brassica napus

<400> SEQUENCE: 11

Ala Pro Gly Leu Thr Gln Thr Thr Val Lys Ser Ala Val Thr Ile
 1               5                  10                  15

Thr Lys Pro Ser Pro Val His Gly Asp Arg Ala Tyr Val Thr Phe
                20                  25                  30

Leu Ala Gly Asn Gly Asp Tyr Val Lys Gly Val Val Gly Leu Ala Lys
            35                  40                  45

Gly Leu Arg Lys Val Lys Ser Ala Tyr Pro Leu Val Val Ala Ile Leu
        50                  55                  60

Pro Asp Val Pro Glu Glu His Arg Arg Val Leu Val Glu Gln Gly Cys
65                  70                  75                  80

Ile Val Arg Glu Ile Glu Pro Val Tyr Pro Pro Glu Asn Gln Thr Gln
                85                  90                  95

Phe Ala Met Ala Tyr Tyr Val Ile Asn Tyr Ser Lys Leu Arg Ile Trp
            100                 105                 110

Lys Phe Val Glu Tyr Ser Lys Met Leu Tyr Leu Asp Gly Asp Ile Gln
        115                 120                 125

Val Tyr Glu Asn Ile Asp His Leu Phe Asp Leu Pro Asp Gly Tyr Phe
    130                 135                 140

Tyr Ala Val Met Asp Cys Phe Cys Glu Lys Thr Trp Ser His Thr Pro
145                 150                 155                 160

Gln Tyr Lys Ile Gly Tyr Cys Gln Gln Cys Pro Glu Lys Val Gln Trp
                165                 170                 175

Pro Lys Glu Glu Leu Gly Glu Pro Pro Ser Leu Tyr Phe Asn Ala Gly
            180                 185                 190

Met Phe Val Phe Glu Pro Gly Leu Asp Thr Tyr Glu Asp Leu Leu Arg
        195                 200                 205

Thr Leu Lys Ile Thr Pro Pro Thr Pro Phe Ala Glu Gln Asp Phe Leu
    210                 215                 220

Asn Met Tyr Phe Glu Lys Ile Tyr Lys Pro Ile Pro Leu Val Tyr Asn
225                 230                 235                 240

Leu Val Leu Ala Met Leu Trp Arg His Pro Glu Asn Val Glu Leu Asp
                245                 250                 255
```

Lys Val Lys Val His Tyr Cys Ala Ala Gly Ser Lys Pro Trp Arg
            260                 265                 270

Tyr Thr Gly Lys Glu Ala Asn Met Glu Arg Glu Asp Ile Lys Met Leu
        275                 280                 285

Val Asn Lys Trp Trp Asp Ile Tyr Asn Asp Asp Ser Leu Asp Tyr Lys
        290                 295                 300

Lys Ser Val Gly Asp Leu Val Glu Glu Ser Asp Val Val Asn Leu Lys
305                 310                 315                 320

Pro Phe Ile Ser Ala Leu Thr Glu Ala Gly Pro Val Lys Tyr Val Thr
                325                 330                 335

Ala Pro Ser Ala Ala
            340

<210> SEQ ID NO 12
<211> LENGTH: 334
<212> TYPE: PRT
<213> ORGANISM: Pisum sativum

<400> SEQUENCE: 12

Met Ala Pro Glu Ile Val Gln Thr Ser Thr Lys Pro Val Thr Gly Phe
1               5                   10                  15

Thr Lys Leu Lys Arg Ala Tyr Val Thr Phe Leu Ala Gly Asn Gly Asp
            20                  25                  30

Tyr Val Lys Gly Val Ile Gly Leu Ala Lys Gly Leu Arg Lys Val Lys
        35                  40                  45

Thr Ala Tyr Pro Leu Val Val Ala Val Leu Pro Asp Val Pro Glu Glu
    50                  55                  60

His Arg Glu Met Leu Glu Ser Gln Gly Cys Ile Val Arg Glu Ile Gln
65                  70                  75                  80

Pro Val Tyr Pro Pro Glu Asn Gln Thr Gln Phe Ala Met Ala Tyr Tyr
                85                  90                  95

Val Ile Asn Tyr Ser Lys Leu Arg Ile Trp Glu Phe Val Glu Tyr Ser
            100                 105                 110

Lys Met Ile Tyr Leu Asp Gly Asp Ile Gln Val Tyr Glu Asn Ile Asp
        115                 120                 125

His Leu Phe Asp Leu Pro Asp Gly Tyr Phe Tyr Ala Val Met Asp Cys
    130                 135                 140

Phe Cys Glu Lys Thr Trp Ser His Thr Pro Gln Tyr Lys Ile Gly Tyr
145                 150                 155                 160

Cys Gln Gln Cys Pro Glu Lys Val Gln Trp Pro Lys Glu Met Gly Glu
                165                 170                 175

Pro Pro Ser Leu Tyr Phe Asn Ala Gly Met Phe Leu Phe Glu Pro Ser
            180                 185                 190

Val Glu Thr Tyr Asp Asp Leu Leu Lys Thr Cys Gln Val Thr Ala Pro
        195                 200                 205

Thr Pro Phe Ala Asp Gln Asp Phe Leu Asn Met Tyr Phe Lys Asp Ile
    210                 215                 220

Tyr Arg Pro Ile Pro Leu Val Tyr Asn Leu Val Leu Ala Met Leu Trp
225                 230                 235                 240

Arg His Pro Glu Asn Val Glu Leu Arg Lys Val Lys Val His Tyr
                245                 250                 255

Cys Ala Ala Gly Ser Lys Pro Trp Arg Tyr Thr Gly Lys Glu Glu Asn
            260                 265                 270

Met Gln Arg Glu Asp Ile Lys Met Leu Val Gln Lys Trp Leu Asp Ile

```
                275                 280                 285
Tyr Ser Asp Ser Ser Leu Asp Tyr Lys Lys Asn Leu Ser Gly Asn Cys
    290                 295                 300

Glu Thr Gln Arg Asn Asp Val Glu Glu Pro Phe Val Gln Ala Leu Ser
305                 310                 315                 320

Glu Val Gly Arg Val Arg Tyr Val Thr Ala Pro Ser Ala Ala
                325                 330

<210> SEQ ID NO 13
<211> LENGTH: 328
<212> TYPE: PRT
<213> ORGANISM: Oryza sativa

<400> SEQUENCE: 13

Met Met Gly Pro Asn Val Ser Ser Glu Lys Lys Ala Leu Ala Ala Ala
  1               5                  10                  15

Lys Arg Arg Ala Tyr Val Thr Phe Leu Ala Gly Asp Gly Asp Tyr Trp
                 20                  25                  30

Lys Gly Val Val Gly Leu Ala Lys Gly Leu Arg Arg Val Arg Ser Ala
             35                  40                  45

Tyr Pro Leu Val Val Ala Val Leu Pro Asp Val Pro Gly Glu His Arg
         50                  55                  60

Arg Lys Leu Val Glu Gln Gly Cys Val Val Arg Glu Ile Gln Pro Val
 65                  70                  75                  80

Tyr Pro Pro Glu Ser Gln Thr Gln Phe Ala Met Ala Tyr Tyr Val Ile
                 85                  90                  95

Asn Tyr Ser Lys Leu Arg Ile Trp Glu Phe Val Glu Tyr Glu Arg Met
            100                 105                 110

Val Tyr Leu Asp Ala Asp Ile Gln Val Phe Asp Asn Ile Asp His Leu
        115                 120                 125

Phe Asp Leu Asp Lys Gly Ala Phe Tyr Ala Val Lys Asp Cys Phe Cys
130                 135                 140

Glu Lys Thr Trp Ser His Thr Pro Gln Tyr Asp Ile Gly Tyr Cys Gln
145                 150                 155                 160

Gln Arg Pro Asp Glu Val Ala Trp Pro Glu Arg Glu Leu Gly Pro Pro
                165                 170                 175

Pro Pro Leu Tyr Phe Asn Ala Gly Met Phe Val His Glu Pro Gly Leu
            180                 185                 190

Gly Thr Ala Lys Asp Leu Leu Asp Ala Leu Val Val Thr Pro Pro Thr
        195                 200                 205

Pro Phe Ala Glu Gln Asp Phe Leu Asn Met Phe Phe Arg Glu Gln Tyr
210                 215                 220

Lys Pro Ile Pro Asn Val Tyr Asn Leu Val Leu Ala Met Leu Trp Arg
225                 230                 235                 240

His Pro Glu Asn Val Asp Leu Asp Gln Val Lys Val Val His Tyr Cys
                245                 250                 255

Ala Ala Gly Ser Lys Pro Trp Arg Phe Thr Gly Lys Glu Glu Asn Met
            260                 265                 270

Asn Arg Glu Asp Ile Lys Met Leu Val Lys Arg Trp Trp Asp Ile Tyr
        275                 280                 285

Asn Asp Glu Ser Leu Asp Tyr Lys Glu Glu Asp Asn Ala Asp Glu
        290                 295                 300

Ala Ser Gln Pro Met Arg Thr Ala Leu Ala Glu Ala Gly Ala Val Lys
305                 310                 315                 320
```

Tyr Phe Pro Ala Pro Ser Ala Ala
            325

<210> SEQ ID NO 14
<211> LENGTH: 333
<212> TYPE: PRT
<213> ORGANISM: Ajuga reptans

<400> SEQUENCE: 14

Met Gly Pro Val Val Pro Val Glu Ala Phe Arg Ser Ala Gly Lys Ile
 1               5                  10                  15

Ser Ala Leu Gly Ala Lys Lys Gly Tyr Val Thr Phe Leu Ala Gly Asn
            20                  25                  30

Gly Asp Tyr Val Lys Gly Val Val Gly Leu Ala Lys Gly Leu Arg Lys
         35                 40                  45

Val Lys Ser Ala Tyr Pro Leu Val Val Ala Ile Leu Pro Asp Val Pro
 50                  55                  60

Glu Glu His Arg Glu Leu Leu Arg Ser Gln Gly Cys Ile Val Lys Glu
 65                  70                  75                  80

Ile Glu Pro Ile Tyr Pro Pro Ala Asn Gln Ile Gln Phe Ala Met Ala
             85                  90                  95

Tyr Tyr Val Ile Asn Tyr Ser Lys Leu Arg Ile Trp Asn Phe Glu Glu
            100                 105                 110

Tyr Ser Lys Met Val Tyr Leu Asp Ala Asp Ile Gln Val Tyr Glu Asn
        115                 120                 125

Ile Asp His Leu Leu Asp Thr Pro Asp Gly Tyr Phe Tyr Ala Val Met
130                 135                 140

Asp Cys Phe Cys Glu Lys Thr Trp Ser His Ser Arg Gln Phe Ser Ile
145                 150                 155                 160

Gly Tyr Cys Gln Gln Cys Pro Asn Lys Val Thr Trp Pro Ala Gln Met
                165                 170                 175

Gly Ser Pro Pro Pro Leu Tyr Phe Asn Ala Gly Met Phe Val Phe Glu
            180                 185                 190

Pro Ser Lys Thr Thr Tyr Gln Thr Leu Leu His Thr Leu Arg Ile Thr
        195                 200                 205

Pro Pro Thr Pro Phe Ala Glu Gln Asp Phe Leu Asn Met Phe Phe Glu
    210                 215                 220

Pro Ile Tyr Lys Pro Ile Pro Leu Val Tyr Asn Leu Val Leu Ala Met
225                 230                 235                 240

Leu Trp Arg His Pro Glu Asn Val Glu Leu Lys Val Gln Val Val
                245                 250                 255

His Tyr Cys Ala Ala Gly Ser Lys Pro Trp Arg Tyr Thr Gly Gln Glu
            260                 265                 270

Ala Asn Met Asp Arg Glu Asp Ile Lys Met Leu Val Lys Lys Trp Trp
        275                 280                 285

Asp Val Tyr Asn Asp Glu Ser Leu Asp Phe Lys Ala Glu Asp Ser Ile
    290                 295                 300

Ala Gly Glu Glu Thr Phe Ser Met Pro Ser Phe Ile Ala Ser Leu Pro
305                 310                 315                 320

Glu Pro Ala Val Ser Tyr Ile Pro Ala Pro Ser Ala Ala
                325                 330

<210> SEQ ID NO 15
<211> LENGTH: 292
<212> TYPE: PRT
<213> ORGANISM: Ajuga reptans

<400> SEQUENCE: 15

```
Val Gly Leu Ala Lys Gly Leu Arg Lys Val Gly Thr Ile Tyr Pro Leu
 1               5                  10                  15
Val Val Ala Val Leu Pro Asp Val Pro Pro Glu His Arg Arg Ile Leu
             20                  25                  30
Val Glu Gln Gly Cys Val Val Arg Glu Ile Glu Pro Val Tyr Pro Pro
         35                  40                  45
Glu Asn His Thr Glu Phe Ala Met Ala Tyr Tyr Val Ile Asn Tyr Ser
     50                  55                  60
Lys Leu Arg Ile Trp Glu Phe Val Glu Tyr Ser Lys Met Ile Tyr Leu
 65                  70                  75                  80
Asp Gly Asp Ile Gln Val Phe Glu Asn Ile Asp His Leu Phe Asp Leu
                 85                  90                  95
Glu Asn Gly Tyr Phe Tyr Ala Val Met Asp Cys Phe Cys Glu Lys Thr
            100                 105                 110
Trp Ser His Thr Pro Gln Tyr Gln Ile Gly Tyr Cys Gln Gln Ser Pro
        115                 120                 125
Lys Arg Val His Trp Pro Lys Gln Leu Gly Pro Lys Pro Pro Leu Tyr
    130                 135                 140
Phe Asn Ala Gly Met Phe Val Tyr Glu Pro Ser Leu Pro Thr Tyr His
145                 150                 155                 160
Asp Leu Leu His Thr Leu Lys Ile Thr Pro Thr Pro Phe Ala Glu
                165                 170                 175
Gln Asp Phe Leu Asn Met Phe Leu Arg Asp Val Tyr Arg Pro Ile Pro
            180                 185                 190
Asn Val Tyr Asn Leu Val Leu Ala Met Leu Trp Arg His Pro Glu Asn
        195                 200                 205
Val Asn Leu Glu Ala Val Lys Val Val His Tyr Cys Ala Ala Gly Ser
    210                 215                 220
Lys Pro Trp Arg Tyr Thr Gly Glu Glu Glu Asn Met Asp Arg Asn Asp
225                 230                 235                 240
Ile Lys Met Leu Val Asn Lys Trp Arg Asp Ile Tyr Asp Asp Glu Met
                245                 250                 255
Leu Asp Tyr Asn Ala Val Ala Asp Pro Ala Ala Asp Gly Leu Gln Leu
            260                 265                 270
Thr Ala Val Leu Thr Glu Ala Ala Gly Val Val Arg Phe Ile Pro Ala
        275                 280                 285
Pro Ser Ala Ala
    290
```

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 16
gcggccgctt tttttttttt ttttt                                     25

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 17
gggccactga accttatggg ggcactgctg gc					32

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 18
aaggaattcc cccccccccc cc					22

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 19
gctccatgat ggctcacaga aacagtcc					28

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 20
gctcacgcat actatgtcat caactactcc					30

<210> SEQ ID NO 21
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 21
gaacttcttg ccctcgacca tcttaggctg ag					32

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 22
gttccaacca tatggcacca gaactc					26

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 23
ggatccgata cttaagctgc ggaaggagc					29

<210> SEQ ID NO 24

```
<211> LENGTH: 27
<212> TYPE: DNA
<213> ORGANISM: Artificial Sequence
<220> FEATURE:
<223> OTHER INFORMATION: Description of Artificial Sequence:  Primer

<400> SEQUENCE: 24
catatgactt ccgagatggc gccacag                                        27

<210> SEQ ID NO 25
<211> LENGTH: 31
<212> TYPE: DNA
<213> ORGANISM: Artificial Sequence
<220> FEATURE:
<223> OTHER INFORMATION: Description of Artificial Sequence:  Primer

<400> SEQUENCE: 25
ggatcctcag gcagcagacg gggcgtgtac g                                   31

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence:  Primer

<400> SEQUENCE: 26
catcactgag catatggctg g                                              21

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence:  Primer

<400> SEQUENCE: 27
ggatccaaag acactcttaa gcagcagatg ggg                                 33

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence:  carboxy
      terminal pentapeptide

<400> SEQUENCE: 28

Ala Pro Ser Ala Ala
 1               5

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence:  Primer

<400> SEQUENCE: 29
catcactgag catatggctg g                                              21

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence:  Primer
```

```
<400> SEQUENCE: 30
ggatccaaag acactcttaa gcagcagatg ggg                    33
```